(12) United States Patent
Orwar et al.

(10) Patent No.: US 7,563,614 B2
(45) Date of Patent: Jul. 21, 2009

(54) SYSTEMS AND METHODS FOR RAPIDLY CHANGING THE SOLUTION ENVIRONMENT AROUND SENSORS

(75) Inventors: Owe Orwar, Hovås (SE); Daniel Chiu, Seattle, WA (US); Johan Pihl, Göteborg (SE); Jon Sinclair, Göteborg (SE); Jessica Olofsson, Göteborg (SE); Mattias Karlsson, Göteborg (SE); Kent Jardemark, Tyreso (SE)

(73) Assignee: Cellectricon AB, Gothenborg (SE)

( * ) Notice: Subject to any disclaimer, the term of this patent is extended or adjusted under 35 U.S.C. 154(b) by 620 days.

(21) Appl. No.: 10/345,107

(22) Filed: Jan. 15, 2003

(65) Prior Publication Data

US 2006/0223164 A1 Oct. 5, 2006

Related U.S. Application Data

(60) Provisional application No. 60/356,377, filed on Feb. 12, 2002.

(51) Int. Cl.
*C12M 1/34* (2006.01)
*G01N 35/00* (2006.01)

(52) U.S. Cl. ............... 435/286.2; 435/287.3; 435/288.5; 422/63; 422/100; 422/130

(58) Field of Classification Search ............. 435/286.4, 435/286.5, 287.3, 288.5, 287.1, 288.4, 286.3
See application file for complete search history.

(56) References Cited

U.S. PATENT DOCUMENTS 5,137,817 A    8/1992   Busta et al. ................. 435/173
5,208,145 A    5/1993   Rogers
5,449,492 A    9/1995   Krishtal ..................... 422/64
5,501,662 A    3/1996   Hofmann .................... 604/20
5,597,699 A    1/1997   Lanzara ..................... 435/7.21
6,193,647 B1   2/2001   Beebe et al. ................. 600/33
6,470,226 B1  10/2002   Olesen et al. ................. 700/56
7,018,819 B2 * 3/2006   Orwar et al. ............. 435/173.6
2001/0029320 A1 10/2001 Trumbull et al. ........... 600/300
2002/0063067 A1 * 5/2002 Bech et al. ................. 205/775

(Continued)

FOREIGN PATENT DOCUMENTS

WO   WO 90/04645   5/1990

(Continued)

OTHER PUBLICATIONS

Sinclair, et al. "A Cell-Based Bar Code Reader for High-Throughput Screening of Ion Channel-Ligand Interactions", Anal. Chem. 2002, 74, 6133-6138.

(Continued)

*Primary Examiner*—William H Beisner
(74) *Attorney, Agent, or Firm*—Edwards Angell Palmer & Dodge LLP; David G. Conlin; Jeffrey L. Kopacz

(57) ABSTRACT

The invention provides microfluidic systems for altering the solution environment around a nanoscopic or microscopic object, such as a sensor, and methods for using the same. The invention can be applied in any sensor technology in which the sensing element needs to be exposed rapidly, sequentially, and controllably, to a large number of different solution environments whose characteristics may be known or unknown.

77 Claims, 33 Drawing Sheets

U.S. PATENT DOCUMENTS

| | | |
|---|---|---|
| 2002/0074227 A1 | 6/2002 | Nisch et al. .................. 204/450 |
| 2002/0076689 A1 | 6/2002 | Farb et al. ....................... 435/4 |
| 2002/0146822 A1 | 10/2002 | Takayama et al. ........... 435/375 |
| 2003/0009112 A1 | 1/2003 | Hammerle et al. ........... 600/547 |
| 2003/0022268 A1 | 1/2003 | Lepple-Wienhues ......... 435/29 |
| 2005/0048651 A1 | 3/2005 | Ryttsen et al. |
| 2006/0078961 A1 | 4/2006 | Chiu et al. |
| 2006/0234298 A1 | 10/2006 | Chiu et al. |

FOREIGN PATENT DOCUMENTS

| | | |
|---|---|---|
| WO | WO 94/20841 | 9/1994 |
| WO | WO 96/10170 | 4/1996 |
| WO | WO 97/05922 | 2/1997 |
| WO | WO 9855870 A1 * | 12/1998 |
| WO | WO 99/24110 | 5/1999 |
| WO | WO 0194939 A1 * | 12/2001 |
| WO | WO-03/068906 A1 | 8/2003 |
| WO | WO-2006/074350 | 7/2006 |

OTHER PUBLICATIONS

Farre, et al., "Screening of Ion Channel Receptor Agonists Using Capillary Electrophoresis-Patch Clamp Detection with Resensitized Detector Cells", Anal. Chem. 2001, 73, 1228-1233.

Stromberg, et al., "Microfluidic Device for Combinatorial Fusion of Liposomes and Cells", Anal Chem. 2001, 73, 126-130.

Jardemark, et al., "Screening of Receptor Antagonists Using Agonist-Activated Patch Clamp Detection in Chemical Separations", Anal. Chem. 1998, 70, 2468-2474.

Fishman, et al., "Cell-to-Cell Scanning in Capillary Electrophoresis", Analytical Chemistry, vol. 68 No. 7, Apr. 1, 1996, 1181-1186.

Orwar, et al., "Patch-Clamp Detection of Neurotransmitters in Capillary Electrophoresis", Science, vol. 272, Jun. 21, 1996, 1779-1782.

Fishman, et al., "Identification of receptor ligands and receptor subtypes using antagonists in a capillary electrophoresis single-cell biosensor separation system", Proc. Natl. Acad. Sci. USA, vol. 92, pp. 7877-7881, Aug. 1995.

Klemic, et al., "Micromolded PDMS planar electrode allows patch clamp electrical recordings from cells", Biosensors and Bioelectronics 17 (2002) 597-604.

Fertig, et al., "Whole Cell Patch Clamp Recording Performed on Plana Glass Chip", Biophysical Journal, vol. 82, Jun. 2002, 3056-3062.

Hamill, et al., "Improved Patch-Clamp Techniques for High-Resolution Current Recording from Cells and Cell-Free Membrane Patches", Pflugers Archiv (1981) 391:85, pp. 100-104.

* cited by examiner

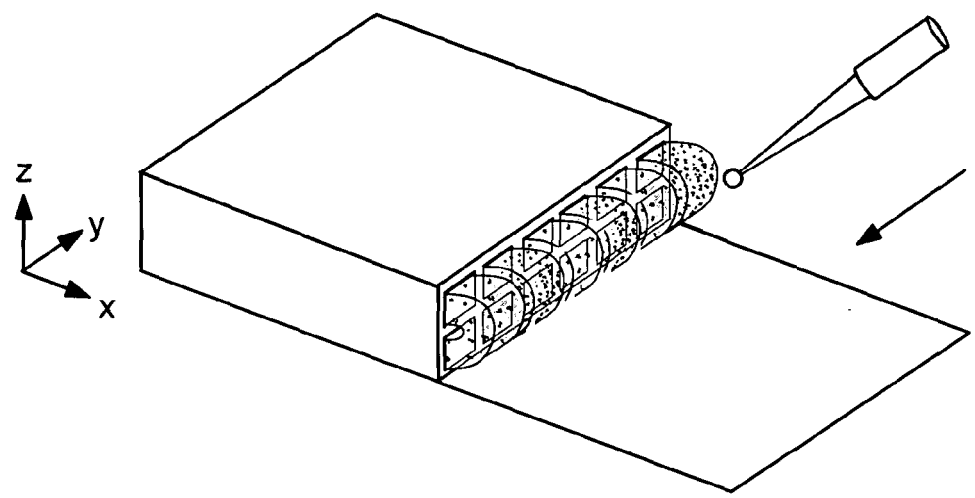
FIG. 5D
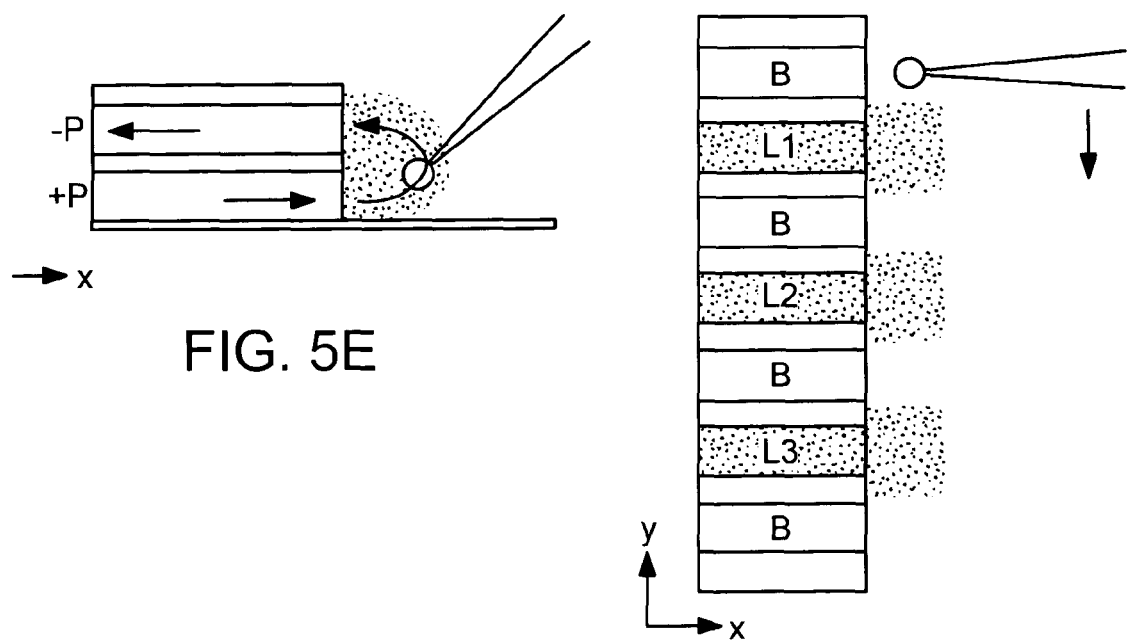
FIG. 5E
FIG. 5F

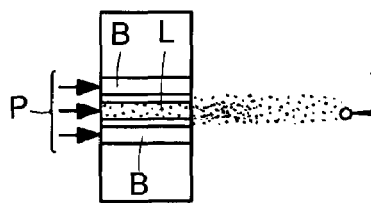
FIG. 18A
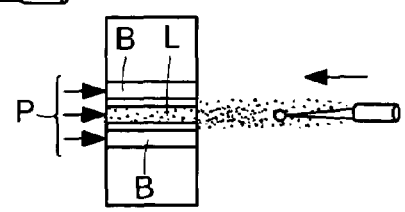
FIG. 18B
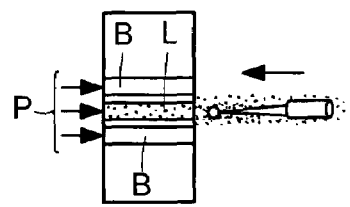
FIG. 18C
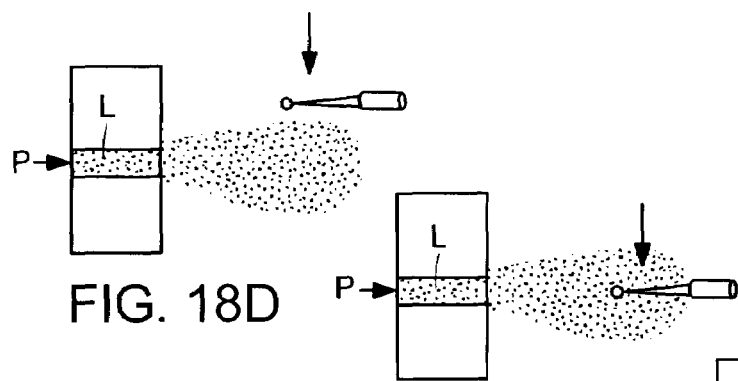
FIG. 18D
FIG. 18E
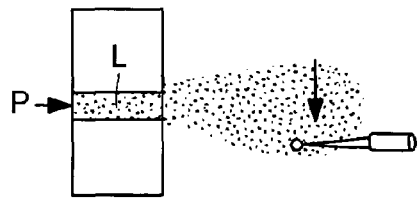
FIG. 18F
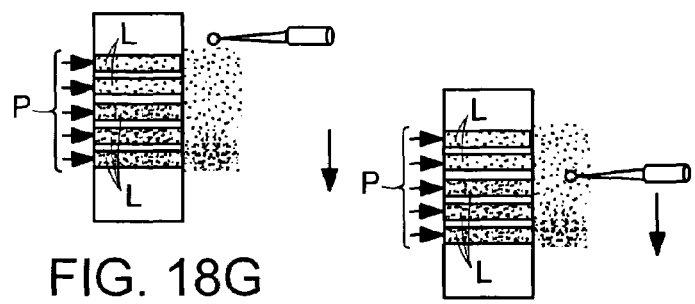
FIG. 18G
FIG. 18H
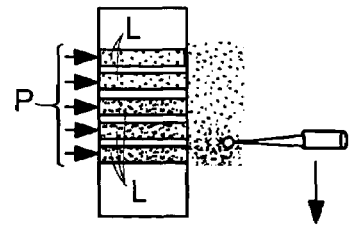
FIG. 18I

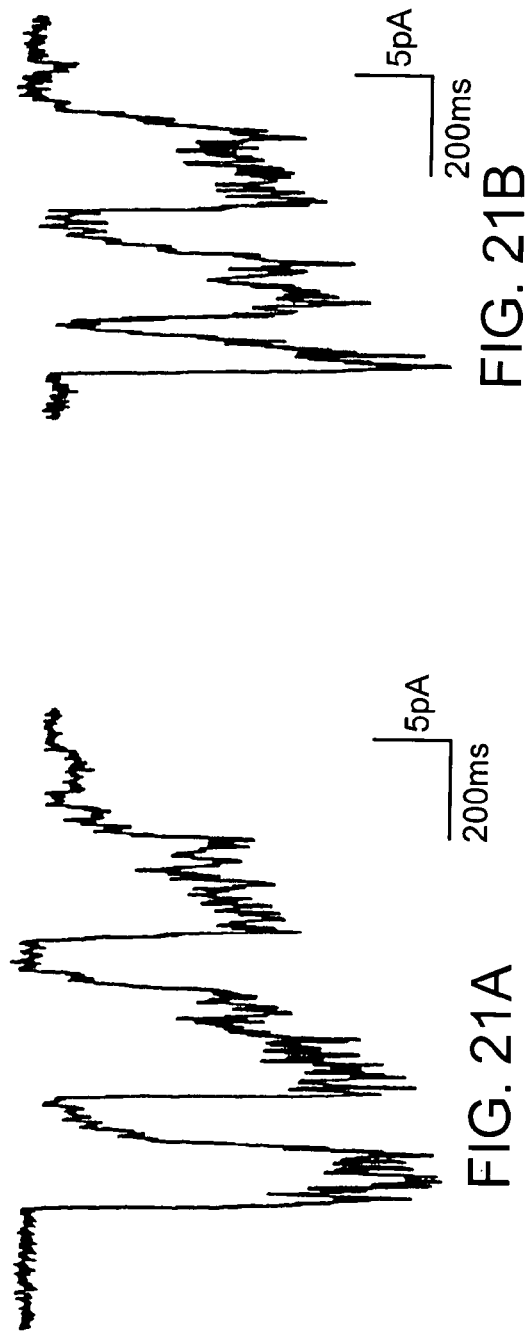
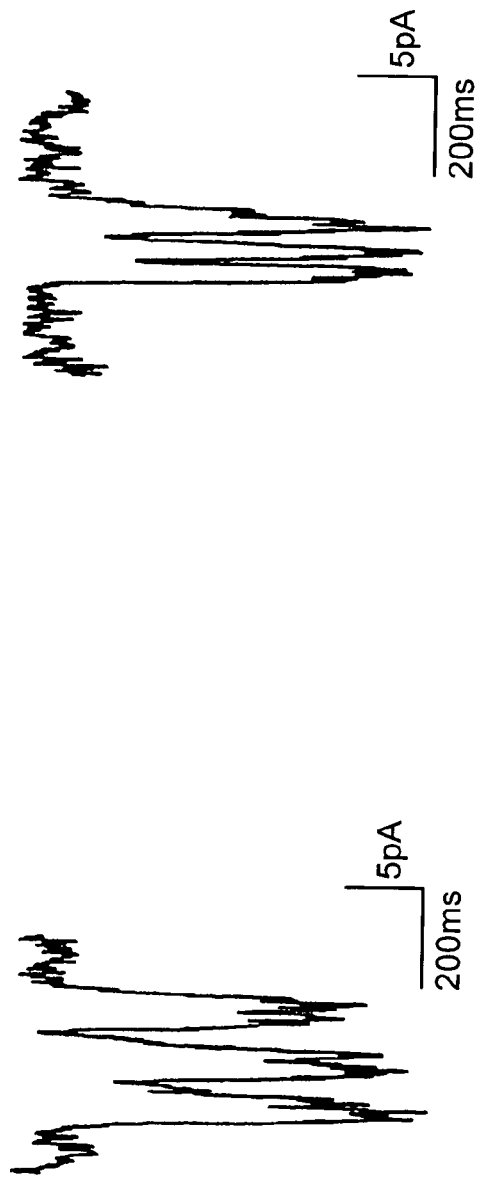
FIG. 21A
FIG. 21B
FIG. 21C
FIG. 21D

Score sheet (mean peak current amplitude of 6 scans)

| Receptor response | 0 | 1 | 5 | 10 | 0 | 0 | 0 | 12 | 0 | 0 | 0 | 0 | 5 | 0 | 0 | 0 | 37 | 0 | 0 | 0 | 0 | 0 | 0 | 1 | 5 | 10 |
|---|---|---|---|---|---|---|---|---|---|---|---|---|---|---|---|---|---|---|---|---|---|---|---|---|---|---|
| Channel # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |

B=Buffer solution
T1= Test compound with known efficacy (agonist) at low concentration
T2= Test compound with known efficacy (agonist) at medium concentration (close to $EC_{50}$-value)
T3= Test compound with known efficacy (agonist) at high concentration (saturating concentration)
α=agonist with unknown efficacy

FIG. 24C

Simulated trace for a single forward scan across microfluidic channel outlets:

Score sheet (mean peak current amplitude of 6 scans)

| Receptor response | 20 | 10 | 5 | 1 | 20 | 20 | 20 | 20 | 1 | 20 | 20 | 20 | 5 | 20 | 15 | 20 | 20 | 20 | 20 | 20 | 20 | 20 | 20 | 10 | 5 | 1 |
|---|---|---|---|---|---|---|---|---|---|---|---|---|---|---|---|---|---|---|---|---|---|---|---|---|---|---|
| Channel # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |

B= Buffer solution
T1= Test compound with known efficacy (antagonist) at low concentration
T2= Test compound with known efficacy (antagonist) at medium concentration (close to $EC_{50}$-value)
T3= Test compound with known efficacy (antagonist) at high concentration (saturating concentration)
A= agonist with known efficacy
ζ= antagonist with unknown efficacy

FIG. 25C

Score sheet (mean peak current amplitude of 6 scans)

| Receptor response | 0 | 1 | 5 | 10 | 0 | 0 | 0 | 0 | 0 | 0 | 0 | 0 | 0 | 0 | 0 | 5 | 0 | 0 | 0 | 0 | 0 | 0 | 0 | 1 | 5 | 10 | 0 | 1 |
|---|---|---|---|---|---|---|---|---|---|---|---|---|---|---|---|---|---|---|---|---|---|---|---|---|---|---|---|---|
| Channel # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 |
| Receptor response | 0 | 1 | 5 | 10 | 36 | 0 | 35 | 0 | 32 | 0 | 27 | 0 | 24 | 0 | 15 | 0 | 5 | 0 | 12 | 0 | 8 | 0 | 6 | 0 | 3 | 0 | 2 | 0 |
| Channel # | 56 | 55 | 54 | 53 | 52 | 51 | 50 | 49 | 48 | 47 | 46 | 45 | 44 | 43 | 42 | 41 | 40 | 39 | 38 | 37 | 36 | 35 | 34 | 33 | 32 | 31 | 30 | 29 |

B = Buffer solution
T1 = Test compound with known efficacy (antagonist or agonist) at low concentration
T2 = Test compound with known efficacy (antagonist or agonist) at medium concentration (close to $EC_{50}$-value)
T3 = Test compound with known efficacy (antagonist or agonist) at high concentration (saturating concentration)
α1-to-α28 agonist with unknown efficacy at different concentration progressively diluted (each step 10 times) to α1

FIG. 26C

| Channel content | B | T1 | T2 | T3 | α1 | α2 | α3 | α4 | α5 | α6 | α7 | T1 | T2 | T3 |
|---|---|---|---|---|---|---|---|---|---|---|---|---|---|---|
| Channel # | 1 | 2 | 3 | 4 | 5 | 6 | 7 | 8 | 9 | 10 | 11 | 12 | 13 | 14 |

Simulated trace for a single forward scan across microfluidic channel outlets.

Score sheet (mean peak current amplitude of 6 scans)

| Receptor response | 0 | 5 | 10 | 20 | 0 | 0 | 34 | 0 | 4 | 0 | 0 | 5 | 10 | 20 |
|---|---|---|---|---|---|---|---|---|---|---|---|---|---|---|
| Channel # | 1 | 2 | 3 | 4 | 5 | 6 | 7 | 8 | 9 | 10 | 11 | 12 | 13 | 14 |

B = Buffer solution
T1 = Test compound with known efficacy (agonist) at low concentration
T2 = Test compound with known efficacy (agonist) at medium concentration (close to $EC_{50}$-value)
T3 = Test compound with known efficacy (agonist) at high concentration (saturating concentration).
α = agonist with unknown efficacy

SYSTEMS AND METHODS FOR RAPIDLY CHANGING THE SOLUTION ENVIRONMENT AROUND SENSORS

RELATED APPLICATIONS

This application claims priority under 35 U.S.C. § 119(e) to U.S. Provisional Application No. 60/356,377, filed Feb. 12, 2002, the entirety of which is incorporated by reference herein.

FIELD OF THE INVENTION

The invention relates to systems and methods for rapid and programmable delivery of aqueous streams to a sensor, such as a cell-based biosensor. In particular, the invention provides methods and systems for high throughput patch clamp analysis.

BACKGROUND OF THE INVENTION

Ion-channels are important therapeutic targets. Neuronal communication, heart function, and memory all critically rely upon the function of ligand-gated and voltage-gated ion-channels. In addition, a broad range of chronic and acute pathophysiological states in many organs such as the heart, gastrointestinal tract, and brain involve ion channels. Indeed, many existing drugs bind receptors directly or indirectly connected to ion-channels. For example, anti-psychotic drugs interact with receptors involved in dopaminergic, serotonergic, cholinergic and glutamatergic neurotransmission.

Because of the importance of ion-channels as drug targets, there is a need for methods which enable high throughput screening (HTS) of compounds acting on ligand-gated and voltage-gated channels (see e.g., Sinclair et al., 2002, *Anal. Chem.* 74: 6133-6138). However, existing HTS drug discovery systems targeting ion channels generally miss significant drug activity because they employ indirect methods, such as raw binding assays or fluorescence-based readouts. Although as many as ten thousand drug leads can be identified from a screen of a million compounds, identification of false positives and false negatives can still result in a potential highly therapeutic blockbuster drug being ignored, and in unnecessary and costly investments in false drug leads.

Patch clamp methods are superior to any other technology for measuring ion channel activity in cells, and can measure currents across cell membranes in ranges as low as picoAmps (see, e.g., Neher and Sakmann, 1976, *Nature* 260: 799-802; Hamill, et al., 1981, *Pflugers Arch* 391: 85-100; Sakmann and Neher, 1983, In *Single-Channel Recording* pp. 37-52, Eds. B. Sakmann and E. Neher. New York and London, Plenum Press, 1983). However, patch clamp methods generally have not been the methods of choice for developing HTS platforms.

SUMMARY OF THE INVENTION

The invention provides microfluidic systems for altering the solution environment around a nanoscopic or microscopic object, such as a sensor, and methods for using the same. The invention can be applied in any sensor technology in which the sensing element needs to be exposed rapidly, sequentially, and controllably, to a large number of different solution environments (e.g., greater than 10 and preferably, greater than about 96 different environments) whose characteristics may be known or unknown. In contrast to prior art microfluidic systems, the interval between sample deliveries is minimized, e.g., on the order of microseconds and seconds, permitting rapid analysis of compounds (e.g., drugs).

In one aspect, the invention provides a system comprising a substrate for changing the solution environment around a nanoscopic or microscopic object, such as a sensor. The substrate comprises an open-volume chamber for the sensor, and a plurality of channels. Each channel comprises an outlet for delivering a substantially separate aqueous stream into the chamber. In one aspect, the outlets are substantially parallel, i.e., arrayed linearly in a single plane. The dimensions of the outlets can vary; however, in one aspect, where the sensor is a biological cell, the diameter of each of the outlets is, preferably, at least about the diameter of the cell. Preferably, a plurality, if not all, of the channels programmably deliver a fluid stream into the chamber.

In a preferred aspect, each channel of the substrate comprises at least one inlet for receiving solution from a reservoir, conforming in geometry and placement on the substrate to the geometry and placement of wells in a multi-well plate. For example, the substrate can comprise 96-1024 reservoirs, each connected to an independent channel on the substrate. Preferably, the center-to-center distance of each reservoir corresponds to the center-to-center distance of wells in an industry standard microtiter or multi-well plate.

In a further aspect, the substrate comprises one or more treatment chambers or microchambers for delivering a treatment to a cell placed within the treatment chamber. The treatment can comprise exposing the cell to a chemical or compound, (e.g. drugs or dyes, such as calcium ion chelating fluorogenic dyes), exposing the cell to an electrical current (e.g., electroporation, electrofusion, and the like), or exposing the cell to light (e.g., exposure to a particular wavelength of light). A treatment chamber can be used for multiple types of treatments which may be delivered sequentially or simultaneously. For example, an electrically treated cell also can be exposed to a chemical or compound and/or exposed to light. Treatment can be continuous over a period of time or intermittent (e.g., spaced over regular or irregular intervals). The cell treatment chamber can comprise a channel with an outlet for delivering a treated cell to the sensor chamber or directly to a mechanism for holding the cell connected to a positioner (e.g., a micropositioner or nanopositioner) for positioning the cell within the chamber.

Preferably, the base of the sensor chamber is optically transmissive and in one aspect, the system further comprises a light source (e.g., such as a laser) in optical communication with the open volume chamber. The light source can be used to continuously or intermittently expose the sensor to light of the same or different wavelengths. The sensor chamber and/or channels additionally can be equipped with control devices. For example, the sensor chamber and/or channels can comprise temperature sensors, pH sensors, and the like, for providing signals relating to chamber and/or channel conditions to a system processor.

The sensor chamber can be adapted for receiving a variety of different sensors. In one aspect, the sensor comprises a cell or a portion of a cell (e.g., a cell membrane fraction). In another aspect, the cell or cell membrane fraction comprises an ion channel, including, but not limited to, a presynaptically-expressed ion channel, a ligand-gated channel, a voltage-gated channel, and the like. In a further aspect, the cell comprises a receptor, such as a G-Protein-Coupled Receptor (GPCR), or an orphan receptor for which no ligand is known, or a receptor comprising a known ligand.

A cultured cell can be used as a sensor and can be selected from the group consisting of CHO cells, NIH-3T3 cells, and HEK-293 cells, and can be recombinantly engineered to express a sensing molecule such as an ion channel or receptor. Many other different cell types also can be used, which can be selected from the group consisting of mammalian cells (e.g., including, but not limited to human cells, primate cells, bovine cells, swine cells, other domestic animals, and the like); bacterial cells; protist cells; yeast cells; plant cells; invertebrate cells, including insect cells; amphibian cells; avian cells; fish; and the like.

A cell membrane fraction can be isolated from any of the cells described above, or can be generated by aggregating a liposome or other lipid-based particle with a sensing molecule, such as an ion channel or receptor, using methods routine in the art.

The cell or portion of the cell can be positioned in the chamber using a mechanism for holding the cell or cell portion, such as a pipette (e.g., a patch clamp pipette) or a capillary connected to a positioner (e.g., such as a micropositioner or nanopositioner or micromanipulator), or an optical tweezer. Preferably, the positioner moves the pipette at least in an x-, y-, z-, direction. Alternatively or additionally, the positioner may rotate the pipette. Also, preferably, the positioner is coupled to a drive unit which communicates with a processor, allowing movement of the pipette to be controlled by the processor.

In one aspect, the base of the chamber comprises one or more depressions and the cell or portion of the cell is placed in a depression which can be in communication with one or more electrodes (e.g., the sensor can comprise a planar patch clamp chip).

Non-cell-based sensors also can be used in the system. Suitable non-cell based sensors include, but are not limited to: a surface plasmon energy sensor; an FET sensor; an ISFET; an electrochemical sensor; an optical sensor; an acoustic wave sensor; a sensor comprising a sensing element associated with a Quantum Dot particle; a polymer-based sensor; a single molecule or an array of molecules (e.g., nucleic acids, peptides, polypeptides, small molecules, and the like) immobilized on a substrate. The sensor chamber also can comprise a plurality of different types of sensors, non-cell based and/or cell-based. A sensor substrate can be affixed to the base of the chamber or the substrate can simply be placed on the base of the chamber. Alternatively, the base of the chamber itself also can serve as the sensor substrate and one or more sensing elements can be stably associated with the base using methods routine in the art. In one aspect, sensing elements are associated at known locations on a substrate or on the base of the sensor chamber.

However, an object placed within a chamber need not be a sensor. For example, the object can be a colloidal particle, beads, nanotube, a non-sensing molecule, silicon wafer, or other small elements.

The invention also provides a system comprising a substrate which comprises at least one chamber for receiving a cell-based biosensor, a plurality of channels, at least one cell storage chamber and at least one cell treatment chamber. Preferably, each channel comprises an outlet for delivering a fluid stream into the chamber, and the cell treatment chamber is adapted for delivering an electrical current to a cell placed within the cell treatment chamber. In one aspect, the cell treatment chamber further comprises a channel with an outlet for delivering a cell to the sensor chamber for receiving the cell-based biosensor. The system can be used to rapidly and programmably change the solution environment around a cell which has been electroporated and/or electrofused, and/or otherwise treated within the cell treatment chamber. Alternatively, or additionally, the sensor chamber also can be used as a treatment chamber and in one aspect, the sensor chamber is in electrical communication with one or more electrodes for continuously or intermittently exposing a sensor to an electric field.

In one aspect, a system according to the invention further comprises a scanning mechanism for scanning the position of a sensor relative to the outlets of the channels. The scanning mechanism can translate the substrate relative to a stationary sensor, or can translate the sensor relative to a stationary substrate, or can move both sensor and substrate at varying rates and directions relative to each other. In one aspect, the sensor is positioned relative to an outlet using a mechanism for holding the sensor (e.g., such as a pipette or capillary) coupled to a positioner (e.g., a micropositioner or nanopositioner or micromanipulator). Thus, the positioner can be used to move the sensor across a plurality of fluid streams exiting the outlets of the channels by moving the mechanism for holding the sensor. Alternatively, or additionally, scanning also can be regulated by producing pressure drops sequentially across adjacent microchannels.

Preferably, the scanning mechanism is in communication with a processor and translation occurs in response to instructions from the processor (e.g., programmed instructions or instructions generated as a result of a feedback signal). In one aspect, the processor controls one or more of: the rate of scanning, the direction of scanning, acceleration of scanning, and number of scans. Thus, the system can be used to move nanoscopic and microscopic objects in a chamber to user-selected, or system-selected coordinates, for specified (e.g., programmable) lengths of time. Preferably, the system processor also can be used to locate the position of one or more objects in the chamber, e.g., in response to previous scanning actions and/or in response to optical signals from the objects detected by the system detector. In one aspect, the system further comprises a user device in communication with the processor which comprises a graphical user display for interfacing with a user. For example, the display can be used to display coordinates of object(s) within the chamber, or optical data or other data obtained from the chamber.

The invention additionally provides a substrate comprising a chamber for receiving a cell-based biosensor which comprises a receptor or ion channel. In one aspect, the system sequentially exposes a cell-based biosensor for short periods of time to one or several ligands which binds to the receptor/ion channel and to buffer without ligand for short periods of time through interdigitated channels of the substrate. For example, selective exposure of a cell biosensor to these different solution conditions for short periods of time can be achieved by scanning the cell-based biosensor across interdigitated channels which alternate delivery of one or several ligands and buffer. The flow of buffer and sample solution in each microfluidic channel is preferably a steady state flow at constant velocity.

However, in another aspect, the system delivers pulses (e.g., pulsatile on/off flow) of buffer to a receptor through a superfusion capillary positioned in proximity to both the cell-based biosensor or other type of sensor and to an outlet through which a fluid is streaming. For example, the system can comprise a mechanism for holding the sensor which is coupled to a positioner (e.g., a micropositioner, nanopositioner, micromanipulator, etc.) for positioning the c sensor in proximity to the outlet and a capillary comprising an outlet in sufficient proximity to the mechanism for holding the sensor to deliver a buffer from the capillary to the sensor. A scanning mechanism can be used to move both the capillary and sensor simultaneously, to maintain the appropriate proximity of the capillary to the sensor. The capillary also can be coupled to a pumping mechanism to provide pulsatile delivery of buffer to the sensor. In another aspect, the flow rate of buffer from the one or more superfusion capillaries in proximity to one or more sensors can be higher or lower than the flow rate of fluid from the channels.

The invention further provides a substrate which comprises a circular chamber for receiving a sensor, comprising a cylindrical wall and a base. In one aspect, the substrate comprises a plurality of channels comprising outlets whose openings are radially disposed about the circumference of the wall of the chamber (e.g., in a spokes-wheel configuration), for delivering samples into the chamber. Preferably, the substrate also comprises at least one output channel for draining waste from the chamber. In one aspect, at least one additional channel delivers buffer to the chamber. Preferably, the angle between the at least one additional channel for delivering buffer and the output channel is greater than 10°. More preferably, the angle is greater than 90°. The channel "spokes" may all lie in the same plane, or at least two of the spokes may lie in different planes.

Rapid, programmed exchange of solutions in the chamber is used to alter the solution environment around a sensor placed in the chamber and multiple output channels can be provided in this configuration. For example, there may be an output channel for each channel for delivering sample/buffer. The number of channels for delivering also can be varied, e.g., to render the substrate suitable for interfacing with an industry standard microtiter plate. For example, there may be 96 to 1024 channels for delivering samples. In another aspect, there may be an additional, equal number of channels for delivering buffer (e.g., to provide interdigitating fluid streams of sample and buffer).

The invention also provides a multi-layered substrate for changing the solution environment around a sensor, comprising: a first substrate comprising channels for delivering fluid to a sensor; a filter layer for retaining one or more sensors which is in proximity to the first substrate; and a second substrate comprising a waste reservoir for receiving fluid from the filter layer. One or more sensors can be provided between the first substrate and the filter layer. In one aspect, at least one of the sensors is a cell. Preferably, the system further comprises a mechanism for creating a pressure differential between the first and second substrate to force fluid flowing from channels in the first substrate through the filter and into the waste reservoir, i.e., providing rapid fluid exchange through the filter (i.e., sensor) layer.

The invention additionally provides a substrate which comprises a chamber for receiving a sensor, a first channel comprising an outlet intersecting with the chamber, and a plurality of sample delivery channels intersecting with the first channel. The first channel also is connected to a buffer reservoir (e.g., through a connecting channel). In one aspect, the longitudinal axes of the sample delivery channels are parallel with respect to each other, but are angled with respect to the longitudinal axis of the first channel (e.g., providing a "fish bone" shape). Rapid flow of solution through the first channel and/or sample channels can be achieved through a positive pressure mechanism in communication with the buffer reservoir and/or sample channels. Passive one-way valves can be provided at the junction between sample delivery channels and the first channel to further regulate flow rates. In one aspect, at least one of the sample reservoirs is sealed by a septum which can comprise a needle or tube inserted therein.

The invention further provides a substrate which comprises a chamber for receiving a sensor, a plurality of delivery channels comprising outlets for feeding sample or buffer into the chamber, and a plurality of drain channels comprising inlets opposite the outlets of the delivery channels. The longitudinal axes of the delivery channels can be in the same, or a different plane, from the longitudinal axes of the drain channels. In one aspect, the plurality of drain channels is on top of the plurality of inlet channels (i.e., the substrate is three-dimensional).

Any of the systems described above can further comprise a pressure control device for controlling positive and negative pressure applied to at least one microchannel of the substrate. In systems where substrates comprise both delivery channels as well as output channel(s), the system preferably further comprises a mechanism for applying a positive pressure to at least one delivery channel while applying a negative pressure to at least one output channel. Preferably, hydrostatic pressure at at least one of the channels can be changed in response to a feedback signal received by the processor.

The system can thus regulate when, and through which channel, a fluid stream is withdrawn from the chamber. For example, after a defined period of time, a fluid stream can be withdrawn from the chamber through the same channel through which it entered the system or through a different channel. When a drain channel is adjacent to a delivery channel, the system can generate a U-shaped fluid stream which can efficiently recycle compounds delivered through delivery channels.

As described above, multiple delivery channel configurations can be provided: straight, angled, branched, fish-bone shaped, and the like. In one aspect, each delivery channel comprises one or more intersecting channels whose longitudinal axes are perpendicular to the longitudinal axis of the delivery channels. In another aspect, each delivery channel comprises one or more intersecting channels whose longitudinal axes are at an angle with respect to the delivery channel.

In general, any of the channel configurations described above are interfaceable with containers for delivering samples to the reservoirs or sample inlets (e.g., through capillaries or tubings connecting the containers with the reservoirs/inlets). In one aspect, at least one channel is branched, comprising multiple inlets. Preferably, the multiple inlets interface with a single container. However, multiple inlets also may interface with several different containers.

Further, any of the substrates described above can be interfaced to a multi-well plate (e.g., a microtiter plate) through one or more external tubings or capillaries. The one or more tubings or capillaries can comprise one or more external valves to control fluid flow through the tubings or capillaries. In one aspect, a plurality of the wells of the multi-well plates comprise known solutions. The system also can be interfaced with a plurality of microtiter plates; e.g., the plates can be stacked, one on top of the other. Preferably, the system further comprises a micropump for pumping fluids from the wells of a microtiter plate or other suitable container(s) into the reservoirs of the substrate. More preferably, the system programmably delivers fluids to selected channels of the substrate through the reservoirs.

In one aspect, a system according to the invention further comprises a detector in communication with a sensor chamber for detecting sensor responses. For example, the detector can be used to detect a change in one or more of: an electrical, optical, or chemical property of the sensor. In one aspect, in response to a signal from the detector, the processor alters one or more of: the rate of scanning, the direction of scanning, acceleration of scanning, number of scans, and pressure on one or more channels.

The invention also provides a method for changing an aqueous solution environment locally around a nanoscopic or microscopic object (e.g., such as a sensor). The method comprises providing a substrate which comprises an open volume chamber comprising a nanoscopic or microscopic object and an aqueous fluid. The substrate further comprises a plurality of channels, each channel comprising an outlet intersecting with the open volume chamber. Substantially separate aqueous streams of fluid are delivered into the open volume chamber, at least two of which comprise different fluids.

Preferably, fluid streams exiting from the at least two adjacent channels are collimated and laminar within the open volume. However, the system can comprise sets of channels (at least two adjacent channels) wherein at least one set delivers collimated laminar streams, while at least one other set delivers non-collimated, non-laminar streams. In one aspect, the streams flow at different velocities. Fluid can be delivered from the channels to the chamber by a number of different methods, including by electrophoresis and/or by electroosmosis and/or by pumping.

In one aspect, the longitudinal axes of the channels are substantially parallel. The channels can be arranged in a linear array, in a two-dimensional array, or in a three-dimensional array, can comprise treatment chambers, sensor chambers, reservoirs, and/or waste channels, and can be interfaced with container(s) or multi-well plate(s) as described above. In one aspect, output channels can overly input channels (i.e., in a three-dimensional configuration). Preferably, the longitudinal axis of at least one output or drain channel is parallel, but lying in a different plane, relative to the longitudinal axis of at least one input channel. By applying a positive pressure to an input channel at the same time that a negative pressure is applied to an adjacent output or drain channel, a U-shaped fluid stream can be generated within the chamber. In this way, an object within the chamber can be exposed to a compound in a fluid stream from an inlet channel which can, for example, be recycled by being withdrawn from the chamber through the adjacent output or drain channel. The U-shaped fluid streams can, preferably, be used to create local well-defined regions of fluid streams with specific composition in a large-volume reservoir or open volume.

Preferably, the object is scanned sequentially across the at least two aqueous fluid streams, thereby altering the aqueous solution environment around the object. Scanning can be performed by moving the substrate and/or the object, or, can be mediated by pressure drops applied to the channels.

The open volume chamber can comprise a plurality of objects; preferably, each object is scanned across at least two streams. Scanning can be performed by a scanning mechanism controlled by a processor as described above. The open volume can, additionally have inlets and outlets for adding and withdrawal of solution. For example, fresh buffer solution can be added to the recording chamber by using a peristaltic pump.

In one aspect, the method further comprises modifying one or more scanning parameters, such as the rate of scanning, the direction of scanning, acceleration of scanning, number of scans, and pressure across one or more channels. Scanning parameters can be modified in response to a feedback signal, such as a signal relating to the response of an object to one or more of aqueous streams. Scanning also can be coordinated with other system operations. For example, in a system comprising a cell-based biosensor, scanning can be coordinated with exposure of the biosensor to an electrical current, i.e., inducing pore formation in a cell membrane of the biosensor, as the biosensor is scanned past one or more sample outlets.

Hydrostatic pressure at one or more channels also can be varied by the processor according to programmed instructions and/or in response to a feedback signal. In one aspect, hydrostatic pressure at each of the plurality of channels is different.

In another aspect, the viscosity of fluids in at least two of the channels is different. In yet another aspect, fluid within at least two of the channels are at a different temperature. In a further aspect, the osmolarity of fluid within at least two of the channels is different. In a still further aspect, the ionic strength of fluid within at least two of the channels is different. Fluid in at least one of the channels also can comprise an organic solvent. By changing these parameters at different outlets, sensor responses can be optimized to maximize sensitivity of detection and minimize background. In some aspects, parameters also can be varied to optimize certain cell treatments being provided (e.g., such as electroporation or electrofusion).

The invention also provides a method for rapidly changing the solution environment around a nanoscopic or microscopic object which comprises rapidly exchanging fluid in a sensor chamber comprising the nanoscopic or microscopic object. In one aspect, fluid exchange in the chamber occurs within less than about 1 minute, preferably, with less than about 30 seconds, less than about 20 seconds, less than about 10 seconds, less than about 5 seconds, or less than about 1 second. In another aspect, fluid exchange occurs within milliseconds. In another aspect fluid exchange occurs within nanoseconds.

In one aspect, the method comprises providing a chamber comprising the object (which may be a sensor or even a single molecule), wherein the chamber comprises a plurality of inlet channels for delivering a fluid into the chamber and a plurality of outlet channels for draining fluid from the chamber. Preferably, the longitudinal axes of the drain channels are at an angle with respect to the longitudinal axes of the delivery channels. In one aspect, the longitudinal axis of at least one drain channel is $\geqq 90°$ with respect to the longitudinal axis of a delivery channel. Preferably, the angle is about 180°. Fluid entering the chamber is withdrawn from the chamber after a predetermined period of time or in response to a feedback signal. By controlling the velocity of fluid flow through the inlet channels and the output or drain channels, complete exchange of fluid in the chamber can occur in less than about 30 seconds, and preferably, in milliseconds.

Preferably, the velocity of fluids in the channels at an angle with respect to each other is different. In one aspect, the hydrostatic pressure of fluids in the channels at an angle with respect to each other is different. In another aspect, the viscosity of fluids in the channels at an angle with respect to each other is different. In still another aspect, the osmolarity of fluids in the channels at an angle with respect to each other is different. In a further aspect, the ionic strength of fluids in the channels at an angle with respect to each other is different. In yet a further aspect, the channels at an angle with respect to each other comprise different organic solvents.

The chamber can be circular, comprising a cylindrical wall and a base and the outlets can be radially disposed around the circumference of the wall, i.e., in a two-dimensional or three-dimensional spokes-wheel configuration. Other configurations are also possible. For example, each delivery channel can comprise an intersecting inlet channel whose longitudinal axis is perpendicular to the delivery channel.

The method can generally be used to measure responses of a cell or portion thereof to a condition in an aqueous environment, by providing a cell or portion thereof in the chamber of any of the substrates described above, exposing the cell or portion thereof to one or more aqueous streams for creating the condition, and detecting and/or measuring the response of the cell or portion thereof to the condition. For example, the condition may be a chemical or a compound to which the cell or portion thereof is exposed and/or can be the osmolarity and/or ionic strength and/or temperature and/or viscosity of a solution in which the cell or portion thereof is bathed.

The composition of the bulk solution in the sensor chamber in any of the substrates described above can be controlled, e.g., to vary the ionic composition of the sensor chamber or to provide chemicals or compounds to the solution. For example, by providing a superfusion system in proximity to the sensor chamber, a chemical or a compound, such as a drug, can be added to the sensor chamber during the course of an experiment.

In one aspect, exposure of the cell or portion thereof to the condition occurs in the sensor chamber. However, alternatively, or additionally, exposure of the cell or portion thereof to the condition can occur in a microchamber which connects to the sensor chamber via one or more channels. The cell or portion thereof can be transferred to the sensor chamber in order to measure a response induced by changing the conditions around the cell.

In one aspect, the invention also provides a method for generating an activated receptor or ion channel in order to detect or screen for antagonists. The method comprises delivering a constant stream of an agonist to a cell-based biosensor in a sensor chamber through a plurality of microchannels feeding into the sensor chamber (e.g., using any of the substrates described above). Preferably, the cell-based biosensor expresses receptor/ion channel complexes which do not desensitize or which desensitize very slowly. Exposure of the biosensor to the agonist produces a measurable response, such that the receptor is activated each time it passes a microchannel delivering agonist. Preferably, a plurality of the agonist delivering microchannels also comprise antagonist whose presence can be correlated with a decrease in the measurable response (e.g., antagonism) when the cell-based biosensor passes by these microchannels. In one aspect, a plurality of microchannels comprises equal amounts of agonist but different concentrations of antagonist. Inhibition of the measurable response can thus be correlated with the presence of a particular dose of antagonist. In another aspect, a plurality of microchannels comprise equal amounts of agonist, but one or more, and preferably all of the plurality of microchannels, comprises different kinds of antagonists. In this way the activity of particular types of antagonists (or compounds suspected of being antagonists) can be monitored.

In one aspect, a periodically resensitized receptor is provided using the superfusion system described above to deliver pulses of buffer to the cell-based biosensor, to thereby remove any bound agonist or modulator desensitizing the receptor, before the receptor is exposed to the next channel outlet containing agonists or receptor modulators. In detection of antagonists, the pulsated superfusion system can also periodically remove the constantly applied agonist. A transient peak response (which is desensitized to a steady state response) is generated when the resensitized biosensor is exposed to the agonist. The generation of this peak response can provide a better signal-to-noise ratio in detection of antagonists.

In another aspect, ion-channels in a cell-based biosensor are continuously activated or periodically activated by changing the potential across the cell-membrane. This provides a sensor for detection of compounds or drugs modulating voltage-dependent ion-channels.

Responses measured by the systems or methods will vary with the type of sensor used. When a cell-based biosensor is used, the agonist-, antagonist-, or modulator-induced changes of the following parameters or cell properties can be measured: cell surface area, cell membrane stretching, ion-channel permeability, release of internal vesicles from a cell, retrieval of vesicles from a cell membrane, levels of intracellular calcium, ion-channel induced electrical properties (e.g., current, voltage, membrane capacitance, and the like), optical properties, or viability.

In one aspect, the sensor comprises at least one patch-clamped cell. For example, the method can be performed by combining the system with a traditional patch clamp set-up. Thus, a cell or cell membrane fraction can be positioned appropriately relative to channel outlets using a patch clamp pipette connected to a positioner such as a micropositioner or nanopositioner.

Alternatively, a patch-clamped cell or patch-clamped cell membrane fraction can be positioned in a depression in the base of the chamber which is in communication with one or more electrodes (e.g., providing a patch clamp chip).

The systems and methods according to the invention can be used to perform high throughput screening for ion channel ligands and for drugs or ligands which act directly or indirectly on ion channels. However, more generally, the systems and methods can be used to screen for compounds/conditions which affect any extracellular, intracellular, or membrane-bound target(s). Thus, the systems and methods can be used to characterize, for example, the effects of drugs on cell. Examples of data that can be obtained for such purposes according to the present invention includes but is not limited to: dose response curves, $IC_{50}$ and $EC_{50}$ values, voltage-current curves, on/off rates, kinetic information, thermodynamic information, etc.

Thus, the system can, for example, be used to characterize if an ion channel or receptor antagonists is a competitive or non-competetive inhibitor. The systems and methods according to the invention also can be used for toxicology screens, e.g., by monitoring cell viability in response to varying kinds or doses of compound, or in diagnostic screens. The method can also be used to internalize drugs, in the cell cytoplasm, for example, using electroporation to see if a drug effect is from interaction with a cell membrane bound outer surface receptor or target or through an intracellular receptor or target. It should be obvious to those of skill in the art that the systems according to the invention can be used in any method in which an object would benefit from a change in solution environment, and that such methods are encompassed within the scope of the instant invention.

BRIEF DESCRIPTION OF THE FIGURES

The objects and features of the invention can be better understood with reference to the following detailed description and accompanying drawings. The Figures are not to scale.

FIG. 1A is a perspective view of a microfluidic chip in which a cell is positioned in proximity to microchannel outlets of the chip using a patch clamp micropipette connected to a positioner. FIG. 1B is a side view, partially in section, of FIG. 1A.

FIG. 2A shows a chip comprising ligand reservoirs (e.g., the reservoirs receive samples of ligands from a 96-well plate). FIG. 2B shows a chip comprising alternating or interdigitating ligand and buffer reservoirs (e.g., every other reservoir receives samples of ligands from one 96-well plate, while the remaining reservoirs receive samples of buffer from another 96-well plate). As shown in FIG. 2C, additional reservoirs can be placed on chip for the storage and transfer of cells or other samples of interest.

FIG. 4A depicts the overall chip structure for both a 2D and 3D microfluidic system. FIG. 4B shows an enlarged view of the reservoirs of the chip and their individual connecting channels. FIG. 4C shows an enlarged view of interdigitating microchannel whose outlets intersect with the sensor chamber of the chip.

FIGS. 5B and 5C are side views showing a 2D and 3D microfluidic chip design, respectively. FIG. 5D is a perspective view of a 3D chip design according to one aspect of the invention, in which the chip comprises a bottom set and top set of channels. FIG. 5E is a side view of FIG. 5D, showing fluid flow can be controlled through pressure differentials so that fluid flowing out of a channel in the bottom set will make a "U-turn" into an overlying channel. FIG. 5F is a top view of FIG. 5D and shows cell scanning across the "U-turn" fluid streams.

FIG. 7A is a perspective view of the overall chip design and microfluidic system. FIGS. 7H-7N show a different embodiment for superfusing cells. As shown in the perspective view in FIG. 7H, instead of providing capillaries for delivering buffer, a number of small microchannels placed at each of the outlets of the ligand delivery channels are used for buffer delivery. As a patch-clamped cell is moved to a ligand channel and the system detects a response, a pulse of buffer can be delivered via the small microchannels onto the cell for superfusion. The advantage to using this system is that the exposure time of the patch-clamped cell to a ligand can be precisely controlled by varying the delay time between signal detection and buffer superfusion. FIG. 7I is a cross-section through the side of a microfluidic system used in this way showing proximity of a patch-clamped cell to both ligand and buffer outlets. FIG. 7J is a cross section, front view of the system, showing flow of buffer streams. FIG. 7K is a cross-section through a top view of the device showing flow of ligand streams and placement of the buffer microchannels. FIGS. 7L-7M show use of pressure applied to a ligand and/or buffer channel to expose a patch clamped cell to ligand and then buffer.

FIGS. 8A-C show mechanical scanning of the patched cell across stationary microchannel outlets. FIGS. 8D-F show mechanical scanning of microchannel outlets relative to a stationary patch-clamped cell. FIGS. 8G-I show a method for sweeping fluid streams across an immobilized patched cell by controlled variation of the pressure across, and flow rates through, each individual microchannel.

FIG. 9A shows the overall arrangements of the microchannels feeding the cell chamber. FIG. 9B is an expanded view of reservoirs and the individual channels through which they are accessed. FIG. 9C shows an enlarged view of microchannel outlets which feed into the cell chamber.

FIG. 11A shows the overall arrangement of channels feeding into, and draining from, a cell chamber. The drain channels feed into a plurality of reservoirs such that the pressure drops across each channel can be independently controlled. FIG. 11B shows an enlarged view of reservoirs and their connecting channels. FIG. 11C shows an enlarged view of microchannel outlets which feed into the cell chamber.

FIG. 14B shows an enlarged view of reservoirs for providing sample to the microchannels. FIG. 14C shows an enlarged view of a plurality of inlet channels intersecting with a central "spine" channel which feeds sample into the sensor chamber. In this enlarged view, intersecting channels are perpendicular to the spine channel rather than slanted; either configuration is possible.

FIGS. 18A-I show schematics of systems for obtaining dose-response measurements based on high-frequency superfusion and re-sensitization of a patch-clamped cell. Superfusion can be achieved through a capillary co-axially placed with respect to a patch-clamp pipette, or through any capillary placed adjacent to the patch pipette which is suitable for superfusion, while translating the patch-clamped cell across a concentration gradient created by streams exiting microchannel outlets. FIGS. 18A-C show a concentration gradient generated by diffusion broadening of a ligand plug in a microchannel. FIGS. 18D-F show lateral diffusion spreading of a ligand stream as it exits a microchannel. FIG. 18G-H show the use of networks of microchannels. "P" indicates a source of pressure applied at one or more microchannels of the systems.

FIG. 19A shows simple microchannel arrangements in which the patch-clampled cell or cells can be scanned across interdigitated ligand and buffer streams. FIG. 19B shows a simple planar radial spokes-wheel structure for carrying out cycles of rapid delivery and withdrawal of compounds into and from a cell chamber housing a patch-clamped cell. FIG. 19C shows a simple fishbone arrangement of microchannel outlets for carrying out rapid and sequential exchange of fluids around a patch-clamped cell.

FIGS. 21A-D show patch clamp current responses of a whole cell to 1 mM acetylcholine as the patch-clamped cell is scanned across the outlets of a parallel 7-channel structure (same structure as that shown in FIG. 16B). Channels 1, 3, 5 and 7 were filled with PBS buffer, while channels 2, 4 and 6 were filled with acetylcholine. The channel flow rate was 6.8 mm/s and the cell scanning speeds in the Figures were A) 0.61 mm/s, B) 1.22 mm/s, C) 2 mm/s and in D) 4 mm/s

FIGS. 24A-C show agonist screening according to one method of the invention using a microfluidic chip comprising 26 outlets feeding into a sensor chamber. As shown in FIG. 24A, the screen is performed linearly from channel outlet position 1 to 26. The scans can be repeated until a sufficient number of scans are performed. A simulated trace and score sheet are shown in FIGS. 24B and C for a single forward scan across microfluidic channel outlets. From this analysis, α6 is the agonist with highest potency, followed by α2.

FIGS. 25A-C show a method for antagonist screening according to one aspect of the invention using a microfluidic chip comprising 26 outlets feeding into a sensor chamber. As shown in FIG. 25A, the screen is performed linearly from position 1-to-26. The scans can be repeated until a sufficient number of scans are performed. As shown in the simulated trace and score sheet, FIGS. 25B and C, respectively, for a single forward scan across microfluidic channel outlets, ζ3 is the antagonist with highest potency followed by ζ 5.

FIGS. 26A-C show a method for dose-response screening using a microfluidic chip comprising 28 outlets feeding into a sensor chamber. As shown in FIG. 24A, the screen is performed linearly from channel outlet position 1 to 28. The scans can be repeated until a sufficient number of scans are performed. A simulated trace and score sheet are shown in FIGS. 26B and C for a single forward scan across microfluidic channel outlets. From these data, a dose-response curve can be created for the unknown agonist α.

FIGS. 27A-C show a method for agonist screening using a microfluidic chip comprising 14 outlets feeding into a sensor chamber and high repetition rate buffer superfusion using a fluidic channel placed close to a patch-clamped cell. As shown in FIG. 27A, the screen is performed linearly from channel outlet position 1 to-14. The scans can be repeated until a sufficient number of scans are performed. A simulated trace for a single forward scan across microfluidic channel outlets and score sheet are shown in FIGS. 27B-C. A plurality of peak responses are obtained per single microchannel outlet. From this analysis, α3 is the agonist with highest potency, followed by α5.

DETAILED DESCRIPTION OF THE INVENTION

Figure 1A:
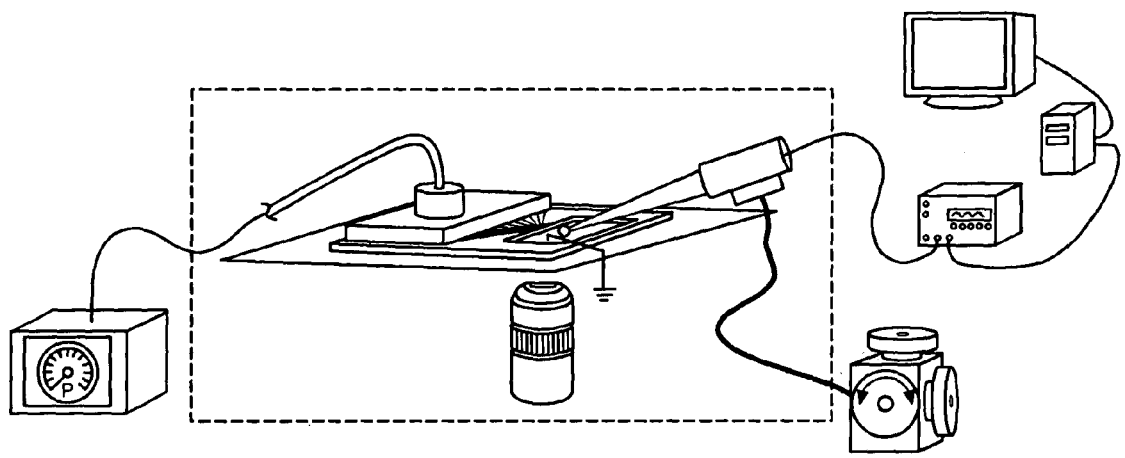
FIGS. 1A and 1B show a schematic of a system according to one aspect of the invention showing integration of a microfluidic chip with patch clamp recordings of ion channel activity.
Figure 1B:
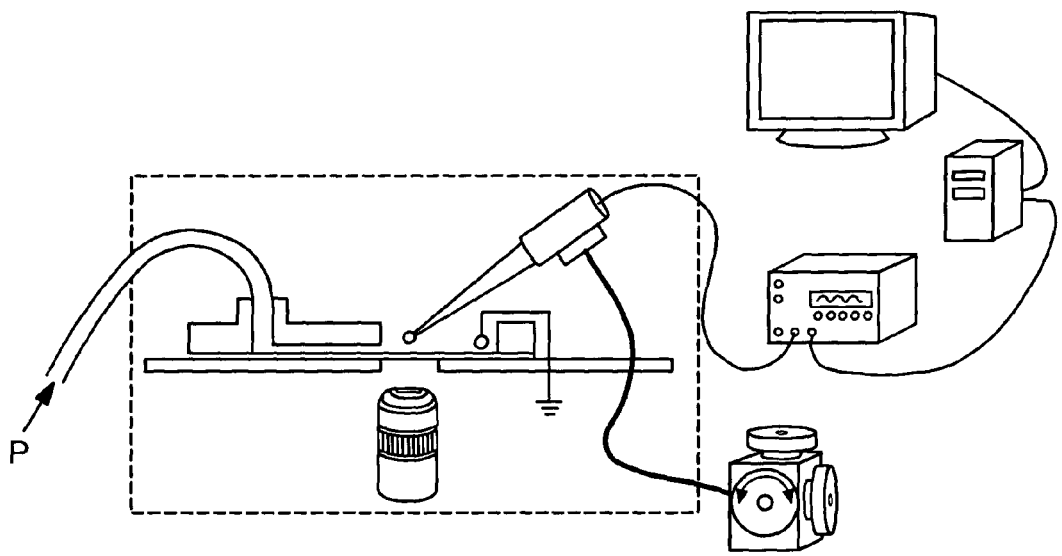

The invention provides a system and method for rapidly and programmably altering the local solution environment around a sensor, such as a cell-based biosensor. The invention further provides a system and method for interfacing microfluidics with patch-clamp detection.

Definitions

The following definitions are provided for specific terms which are used in the following written description.

As used herein, a "microchannel" refers to a groove in a substrate comprising two walls, a base, at least one inlet and at least one outlet. In one aspect, a microchannel also has a roof. The term "micro" does not imply a lower limit on size, and the term "microchannel" is generally used interchangeably with "channel". Preferably, a microchannel ranges in size from about 0.1 μm to about 500 μm, and more preferably ranges from, 1 μm to about 150 μm.

As used herein, a "positioner" refers to a mechanism or instrument that is capable of moving an object or device (e.g., a substrate, a sensor, a cell, a mechanism for holding a sensor, etc.) to which it is coupled. Preferably, the positioner can control movement of an object over distances such as nanometers (e.g., the petitioner is a nanopositioner), micrometers (e.g., the positioner is a micropositioner) and/or millimeters. Suitable positioners move at least in an x-, y-, or z-direction. In one aspect, positioners according to the invention also rotate about any pivot point defined by a user. In a preferred aspect, the positioner is coupled to a drive unit that communicates with a processor, allowing movement of the object to be controlled by the processor through programmed instructions, use of joysticks or other similar instruments, or a combination thereof.

As used herein, "a mechanism for holding a sensor" refers to a device for receiving at least a portion of a sensor to keep the sensor in a relatively stationary position relative to the mechanism. In one aspect, the mechanism comprises an opening for receiving at least a portion of a sensor. For example, such mechanisms include, but are not limited to: a patch clamp pipette, a capillary, a hollow electrode, and the like.

As used herein, the term "moving a sensor" refers to moving the sensor directly or through the use of a mechanism for holding the sensor which is itself moved.

As used herein, a "chamber" refers to an area formed by walls (which may or may not have openings) surrounding a base. A chamber may be "open volume" (e.g., uncovered) or "closed volume" (e.g., covered by a coverslip, for example). A "sensor chamber" is one which receives one or more sensors and comprises outlets in one or more walls from at least two microchannels. However, a sensor chamber according to the invention generally can receive one or more nanoscopic or microscopic objects, without limitation as to their purpose. A sensor chamber can comprise multiple walls in different, not necessarily parallel planes, or can comprise a single wall which is generally cylindrical (e.g., when the chamber is "disc-shaped"). It is not intended that the geometry of the sensor chamber be a limiting aspect of the invention. One or more of the wall(s) and/or base can be optically transmissive. Generally, a sensor chamber ranges in size but is at least about 1 µm. In one aspect, the dimensions of the chamber are at least large enough to receive at least a single cell, such as a mammalian cell. The sensor chamber also can be a separate entity from the substrate comprising the microchannels. For example, in one aspect, the sensor chamber is a petrie dish and the microchannels extend to a surface of the substrate opening into the petrie dish so as to enable fluid communication between the microchannels and the petrie dish.

As used herein, a "sensor" refers to a device comprising one or more molecules capable of producing a measurable response upon interacting with a condition in an aqueous environment to which the molecule is exposed (e.g., such as the presence of a compound which binds to the one or more molecules). In one aspect, the molecule(s) are immobilized on a substrate, while in another aspect, the molecule(s) are part of a cell (e.g., the sensor is a "cell-based biosensor").

As used herein, "a nanoscopic or microscopic object" is an object whose dimensions are in the nm to mm range.

As used herein, the term, "a cell-based biosensor" refers to an intact cell or a part of an intact cell (e.g., such as a membrane patch) which is capable of providing a detectable physiological response upon sensing a condition in an aqueous environment in which the cell (or part thereof) is placed. In one aspect, a cell-based biosensor is a whole cell or part of a cell membrane in electrical communication with an electrically conductive element, such as a patch clamp electrode or an electrolyte solution.

As used herein, the term "receptor" refers to a macromolecule capable of specifically interacting with a ligand molecule. Receptors may be associated with lipid bilayer membranes, such as cellular, golgi, or nuclear membranes, or may be present as free or associated molecules in a cell's cytoplasm or may be immobilized on a substrate. A cell-based biosensor comprising a receptor can comprise a receptor normally expressed by the cell or can comprise a receptor which is non-native or recombinantly expressed (e.g., such as in transfected cells or oocytes).

As used herein, "periodically resensitized" or "periodically responsive" refers to an ion-channel which is maintained in a closed (i.e., ligand responsive) position when it is scanned across microchannel outlets providing samples suspected or known to comprise a ligand. For example, in one aspect, an receptor or ion-channel is periodically resensitized by scanning it across a plurality of interdigitating channels providing alternating streams of sample and buffer. The rate at which the receptor/ion channel is scanned across the interdigitating channels is used to maintain the receptor/ion-channel in a ligand-responsive state when it is exposed to a fluid stream comprising sample. Additionally, or alternatively, the receptor/ion channel can be maintained in a periodically resensitized state by providing pulses of buffer, e.g., using one or more superfusion capillaries, to the ion channel, or by providing rapid exchange of solutions in a sensor chamber comprising the ion channel.

As used herein, a "substantially separate fluid stream" refers to a flowing fluid in a volume of fluid (e.g., such as within a chamber) that is physically continuous with fluid outside the stream within the volume, or other streams within the volume, but which has at least one bulk property which differs from and is in non-equilibrium from a bulk property of the fluid outside of the stream or other streams within the volume of fluid. A "bulk property" as used herein refers to the average value of a particular property of a component (e.g., such as an agent, solute, substance, or a buffer molecule) in the stream over a cross-section of the stream, taken perpendicular to the direction of flow of the stream. A "property" can be a chemical or physical property such as a concentration of the component, temperature, pH, ionic strength, or velocity, for example.

As used herein, the term "in communication with" refers to the ability of a system or component of a system to receive input data from another system or component of a system and to provide an output response in response to the input data. "Output" may be in the form of data, or may be in the form of an action taken by the system or component of the system. For example, a processor "in communication with a scanning mechanism" sends program instructions in the form of signals to the scanning mechanism to control various scanning parameters as described above. A "detector in communication with a sensor chamber" refers to a detector in sufficient optical proximity to the sensor chamber to receive optical signals (e.g., light) from the sensor chamber. A "light source in optical communication" with a chamber refers to a light source in sufficient proximity to the chamber to create a light path from the chamber to a system detector so that optical properties of the chamber or objects contained therein can be detected by the detector.

As used herein, "a measurable response" refers to a response which differs significantly from background as determined using controls appropriate for a given technique.

As used herein, an outlet "intersecting with" a chamber or microchamber refers to an outlet that opens or feeds into a wall or base or top of the chamber or microchamber or into a fluid volume contained by the chamber or microchamber.

As used herein, "superfuse" refers to washing the external surface of an object or sensor (e.g., such as a cell).

The System

In one aspect, the system provides a substrate comprising a plurality of microchannels fabricated thereon whose outlets intersect with, or feed into, a sensor chamber comprising one or more sensors. The system further comprises a scanning mechanism for programmably altering the position of the microchannels relative to the one or more sensors and a detector for monitoring the response of the sensor to exposure to solutions from the different channels. In a preferred aspect, the sensor chamber comprises a cell-based biosensor in electrical communication with an electrode and the detector detects changes in electrical properties of the cell-based biosensor.

The system preferably also comprises a processor for implementing system operations including, but not limited to: controlling the rate of scanning by the scanning mechanism (e.g., mechanically or through programmable pressure drops across microchannels), controlling fluid flow through one or more channels of the substrate, controlling the operation of valves and switches that are present for directing fluid flow, recording sensor responses detected by the detector, and evaluating and displaying data relating to sensor responses. Preferably, the system also comprises a user device in communication with the system processor which comprises a graphical interface for displaying operations of the system and for altering system parameters.

The Substrate

In a preferred aspect, the system comprises a substrate that delivers solutions to one or more sensors at least partially contained within a sensor chamber. The substrate can be configured as a two-dimensional (2D) or three-dimensional (3D) structure, as described further below. The substrate, whether 2D or 3D, generally comprises a plurality of microchannels whose outlets intersect with a sensor chamber that receives the one or more sensors. The base of the sensor chamber can be optically transmissive to enable collection of optical data from the one or more sensors placed in the sensor chamber. When the top of the sensor chamber is covered, e.g., by a coverslip or overlying substrate, the top of the chamber is preferably optically transmissive.

Each microchannel comprises at least one inlet (e.g., for receiving a sample or a buffer). Preferably, the inlets receive solution from reservoirs (e.g., shown as circles in FIGS. 2A and B) that conform in geometry and placement on the substrate to the geometry and placement of wells in an industry-standard microtiter plate. The substrate is a removable component of the system and therefore, in one aspect, the invention provides kits comprising one or more substrates for use in the system, providing a user with the option of choosing among different channel geometries.

Non-limiting examples of different substrate materials include crystalline semiconductor materials (e.g., silicon, silicon nitride, Ge, GaAs), metals (e.g., Al, Ni), glass, quartz, crystalline insulators, ceramics, plastics or elastomeric materials (e.g., silicone, EPDM and Hostaflon), other polymers (e.g., a fluoropolymer, such as Teflon®, polymethylmethacrylate, polydimethylsiloxane, polyethylene, polypropylene, polybutylene, polymethylpentene, polystyrene, polyurethane, polyvinyl chloride, polyarylate, polyarylsulfone, polycaprolactone, polyestercarbonate, polyimide, polyketone, polyphenylsulfone, polyphthalamide, polysulfone, polyamide, polyester, epoxy polymers, thermoplastics, and the like), other organic and inorganic materials, and combinations thereof.

Microchannels can be fabricated on these substrates using methods routine in the art, such as deep reactive ion etching (described further below in Example 1). Channel width can vary depending upon the application, as described further below, and generally ranges from about 0.1 µm to about 10 mm, preferably, from about 1 µm to about 150 µm, while the dimensions of the sensor chamber generally will vary depending on the arrangement of channel outlets feeding into the chamber. For example, where the outlets are substantially parallel to one another (e.g., as in FIGS. 2A-C), the length of the longitudinal axis of the chamber is at least the sum of the widths of the outlets which feed into the chamber. In one aspect, where a whole cell biosensor is used as a sensor in the sensor chamber, the width of one or more outlets of the microchannels is at least about the diameter of the cell. Preferably, the width of each of the outlets is at least about the diameter of the cell.

In one aspect, a cover layer of an optically transmissive material, such as glass, can be bonded to a substrate, using methods routine in the art, preferably leaving openings over the reservoirs and over the sensor chamber when interfaced with a traditional micropipette-based patch clamp detection system. Preferably, the base of the sensor chamber also is optically transmissive, to facilitate the collection of optical data from the sensor.

The Sensor

Cell-Based Biosensors

The system can be used in conjunction with a cell-based biosensor to monitor a variety of cellular responses. The biosensor can comprise a whole cell or a portion thereof (e.g., a cell membrane patch) which is positioned in the sensor chamber using a mechanism for holding a sensor (which may be stationary or movable) such as a pipette, capillary, or column connected to a positioner, such as a micropositioner, a nanopositioner or a micromanipulator, or an optical tweezer, or by controlling flow or surface tension, thereby exposing the cell-based biosensor to solution in the chamber. The biosensor can be scanned across the various channels of the substrate by moving the substrate, i.e., changing the position of the channels relative to the biosensor, or by moving the cell (e.g., by scanning the micropositioner or by changing flow and/or surface tension).

In one aspect, the cell-based biosensor comprises an ion channel and the system is used to monitor ion channel activity. Suitable ion channels include ion channels gated by voltage, ligands, internal calcium, other proteins, membrane stretching (e.g., lateral membrane tension) and phosphorylation (see e.g., as described in Hille B., In *Ion Channels of Excitable Membranes* 1992, Sinauer, Sunderland, Mass., USA). In another aspect, the ion-gated channel is a voltage-gated channel. Voltage-gated channels open in response to a threshold transmembrane voltage. Voltage-gated sodium, potassium, and calcium channels are all essential for conducting an action potential (or a nerve pulse) down an axon and to another nerve cell (or neuron). These ion channels typically comprise a transmembrane sequence with a lysine and/or arginine-rich S4 consensus sequence. The positive amino acids within the S4 sequence are thought to "sense" voltage across a cell membrane, causing an ion channel containing the sequence to either open or close under different voltage conditions.

In another aspect, the ion channel in the cell-based biosensor is a ligand-gated channel. Ligand-gated channels gate (open or close) in response to ligand binding. There are two types of ligand-gated channels, those gated when bound by ligands inside the cell and those gated by ligands outside the cell. Ion channels gated by ligands from outside of the cell are very important in chemical synaptic transmission. These types of ion channels are gated by neurotransmitters, which are the small molecules that actually carry the signal between two nerve cells. Ion channels gated from the inside of the cell are generally controlled by second messengers, which are small signaling molecules inside the cell. Intracellular calcium ions, cAMP and cGMP are examples of second messengers. The most common calcium-gated channel is the calcium-gated potassium channel. This ion channel can generate oscillatory behavior (e.g., for frequency tuning of hair cells in the ear) upon changes in membrane voltage when placed in a positive feedback environment.

In yet another aspect, the ion channel is gated by another protein. Certain signaling proteins have been found to directly gate ion channels. One example of this is a potassium channel gated by the beta-gamma subunit of the G protein, which is a common signaling protein activated by certain membrane receptors.

In a further aspect, the ion channel is gated by phosphorylation. Phosphorylation can be mediated by a protein kinase (e.g., a serine, threonine, or tyrosine kinase), e.g., as part of a signal transduction cascade.

In still a further aspect, the cell-based biosensor comprises a mechanotransduction channel that can be directly gated by a mechanical trigger. For example, the cell-based biosensor can comprise the cation channel of an inner ear hair cell, which is directly gated by a mechanical vibration such as sound. Bending of the hair bundle in a particular direction will affect the probability of channel gating, and therefore, the amplitude of a depolarizing receptor current.

In another aspect, the cell-based biosensor comprises a receptor, preferably, a receptor involved in a signal transduction pathway. For example, the cell-based biosensor can comprise a G Protein Coupled Receptor or GPCR, glutamate receptor, a metabotropic receptor, a hematopoietic receptor, or a tyrosine kinase receptor. Biosensors expressing recombinant receptors also can be designed to be sensitive to drugs which may inhibit or modulate the development of a disease.

Suitable cells which comprise biosensors include, but are not limited to: neurons; lymphocytes; macrophages; microglia; cardiac cells; liver cells; smooth muscle cells; and skeletal muscle cells. In one aspect, mammalian cells are used; these can include cultured cells such as Chinese Hamster Ovary Cells (CHO) cells, NIH-3T3, and HEK-293 cells and can express recombinant molecules (e.g., recombinant receptors and/or ion channels). However, bacterial cells (*E. coli, Bacillus* sp., *Staphylococcus aureus*, and the like), protist cells, yeast cells, plant cells, insect and other invertebrate cells, avian cells, amphibian cells, and oocytes, also can be used, as these are well suited to the expression of recombinant molecules. Cells generally are prepared using cell culture techniques as are know in the art, from cell culture lines, or from dissected tissues after one or more rounds of purification (e.g., by flow cytometry, panning, magnetic sorting, and the like).

Non-Cellular Sensors

In one aspect, the sensor comprises a sensing element, preferably, a molecule which is cellular target (e.g., an intracellular receptor, enzyme, signalling protein, an extra cellular protein, a membrane protein, a nucleic acid, a lipid molecule, etc.), which is immobilized on a substrate. The substrate can be the base of the sensor chamber itself, or can be a substrate placed on the base of the chamber, or can be a substrate which is stably positioned in the chamber (e.g., via a microposi- tioner) and which is moveable or stationary.

The sensor may consist of one or several layers that can include any combination of: a solid substrate; one or more attachment layers that bind to the substrate, and a sensing molecule for sensing compounds introduced into the sensor chamber from one or more channel outlets. Suitable sensors according to the invention, include, but are not limited to, immunosensors, affinity sensors and ligand binding sensors, each of which can respond to the presence of binding partners by generating a measurable response, such as a specific mass change, an electrochemical reaction, or the generation of an optical signal (e.g., fluorescence, or a change in the optical spectrum of the sensing molecule). Such sensors are described in U.S. Pat. No. 6,331,244, for example, the entirety of which is incorporated by reference herein.

In one aspect, the sensor comprises a microelectrode which is modified with a molecule which transports electrons. In response to a chemical reaction caused by contact with one or more compounds in an aqueous stream from one of the microchannels, the molecule will produce a change in an electrical property at the electrode surface. For example, the molecule can comprise an electron-transporting enzyme or a molecule which transduces signals by reduction or oxidation of molecules with which it interacts (see, e.g., as described in, Gregg, et al., *J. Phys. Chem.* 95: 5970-5975, 1991; Heller, *Acc. Chem. Res.* 23(5): 128-134, 1990; In *Diagnostic Biosensor Polymers. ACS Symposium Series.* 556; Usmani, A M, Akmal, N; eds. American Chemical Society; Washington, D.C.; pp. 47-70, 1994; U.S. Pat. No. 5,262,035). Enzymatic reactions also can be performed using field-effect-transistors (FETs) or ion-sensitive field effect transistors (ISFETs).

In another aspect, the sensor comprises a sensing molecule immobilized on a solid substrate such as a quartz chip in communication with an electronic component. The electronic component can be selected to measure changes in any of: voltage, current, light, sound, temperature, or mass, as a measure of interaction between the sensing element and one or more compounds delivered to the sensor chamber (see, as described in, Hall, *Int. J. Biochem.* 20(4): 357-62, 1988; U.S. Pat. No. 4,721,677; U.S. Pat. No. 4,680,268; U.S. Pat. No. 4,614,714; U.S. Pat. No. 6,879,11). For example, in one aspect, the sensor comprises an acoustic wave biosensor or a quartz crystal microbalance, on which a sensor element is bound. In this embodiment, the system detects changes in the resonant properties of the sensor upon binding of compounds in aqueous streams delivered from the microchannels to the sensor element.

In another aspect, the sensor comprises an optical biosensor. Optical biosensors can rely on detection principles such as surface plasmon resonance, total internal reflection fluorescence (TIRF), critical angle refractometry, Brewster Angle microscopy, optical waveguide lightmode spectroscopy (OWLS), surface charge measurements, and evanescent wave ellipsometry, and are known in the art (see, for example, U.S. Pat. No. 5,313,264; EP-A1-0 067 921; EP-A1-0 278 577; Kronick, et al., 1975, *J. Immunol. Meth.* 8: 235-240).

For example, for a sensor employing evanescent wave ellipsometry, the optical response related to the binding of a compound to a sensing molecule is measured as a change in the state of polarization of elliptically polarized light upon reflection. The state of polarization is related to the refractive index, thickness, and surface concentration of a bound sample at the sensing surface (e.g., the substrate comprising the sensing element). In TIRF, the intensity and wavelength of radiation emitted from either natively fluorescent or fluorescence-labelled sample molecules at a sensor is measured. Evanescent wave excitation scattered light techniques rely on measuring the intensity of radiation scattered at a sensor surface due to the interaction of light with sensing molecules (with or without bound compounds). Surface plasmon resonance (SPR) measures changes in the refractive index of a layer of sensor molecules close to a thin metal film substrate (see, e.g., Liedberg, et al., 1983, *Sensors and Actuators* 4:

299; GB 2 197 068). Each of these sensing schemes can be used to provide useful sensors according to the invention.

In yet another aspect, the sensor comprises a sensing molecule associated with a fluorescent semiconductor nanocrystal or a Quantum Dot™ particle. The Quantum Dot particle has a characteristic spectral emission which relates to its composition and particle size. Binding of a compound to the sensing element can be detected by monitoring the emission of the Quantum Dot particle (e.g., spectroscopically) (see, e.g., U.S. Pat. No. 6,306,610).

The sensor further can comprise a polymer-based biosensor whose physical properties change when a compound binds to a sensing element on the polymer. For example, binding can be manifested as a change in volume (such as swelling or shrinkage), a change in electric properties (such as a change in voltage or current or resonance) or in optical properties (such as modulation of transmission efficiency or a change in fluorescence intensity).

It should be obvious to those of skill in the art that a variety of different types of sensors may be adapted for use in present invention, and the examples above are intended to be non-limiting.

In general, the measurement outputs of one or more sensors are connected to a control and evaluating device which is in electrical communication with a detection device and/or system processor. The control and evaluating device can be integrated with the substrate of the sensor and/or with the base of the sensing chamber. The control and evaluating device can comprise various electronic components such as microprocessors, multiplexers, IO units, etc. (see, e.g., as described in U.S. Pat. No. 6,280,586).

Microfluidics

In a preferred aspect, the substrates according to the invention are adapted for microfluidic transport of sample and/or buffer to a sensor chamber.

Interfacing Microfluidic Structures with Well Plates

Samples (i.e., drugs, etc.) contained in sample-well plates (e.g., industry-standard microtiter plates such as 96-well plates) are manipulated and transferred, preferably, using robotic automated array pipettors as are known in the art (see, e.g., Beckman's Biomek 1000 & 2000 automated workstations, available from Beckman Coulter, Inc., Fullerton, Calif.).

To be able to leverage the same sample transfer platform used to array a sample in a well plate, one important design parameter is to ensure the reservoir arrangements in the chip described above are compatible for use with such array pipettors. For example, preferably, the reservoirs in the microfluidic chip are arranged such that the center-to-center distance between each reservoir is identical to the center-to-center distance between each well of the well plate to which the chip interfaced. Preferably, each reservoir has a diameter suitable for receiving a fluid stream from an array pipetter without significantly impeding the flow of fluid from the array pipettor.

In addition to array pipettors, there are other suitable automated devices for transferring samples from well plates onto chips, such as robotic sequential pipettors. It is important to note that the use of these other devices may permit more flexible placement of reservoirs and microchannels on the chip, providing more flexibility in the design of channel parameters. Although a substrate suitable for interfacing between 96-well array pipettors is described in more detail below owing to the widespread use of these pipettors, it should be obvious to those of skill in the art that the general design of the chip and placement of reservoirs can be modified for interfacing with any desirable sample transfer platform, as such platforms evolve. In general, reference to 96-well plates is not intended to be limiting.

Figure 2A:
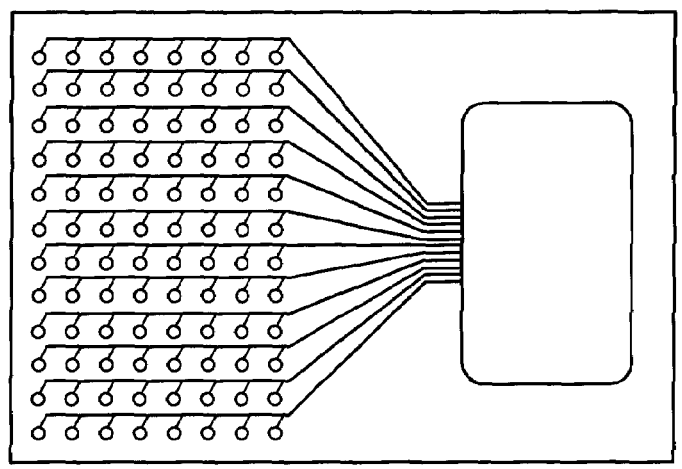
FIGS. 2A-C show top views of different embodiments of microfluidic chips according to aspects of the invention illustrating exemplary placements of reservoirs for interfacing with 96-well plates.
Figure 2B:
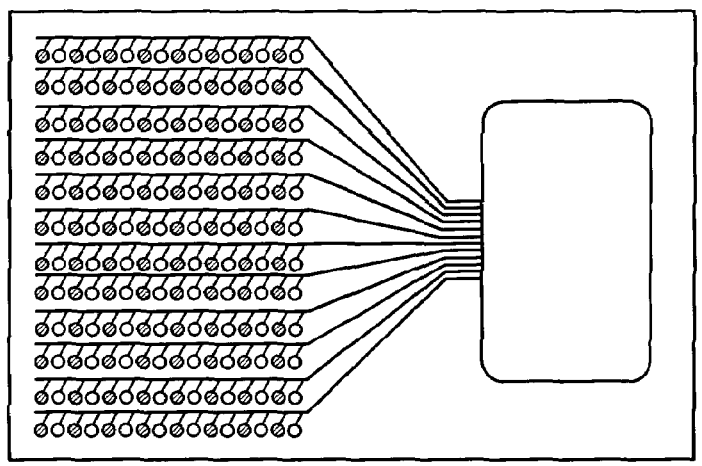

FIGS. 2A and 2B show examples of microfluidic chips according to the invention that are suitable for interfacing with a 96-well plate. FIG. 2A illustrates reservoir arrangements for which no buffer reservoirs are required. FIG. 2B illustrates reservoir arrangements for applications in which alternating (i.e., interdigitating) streams of buffer and sample are provided to a sensor. In this arrangement, the center-to-center distances for both the ligand and buffer reservoirs are identical to the center-to-center distance of the wells of a 96-well plate. To compensate for doubling the number of reservoirs on chip, the diameter of all reservoirs are decreased by half.

Figure 3:
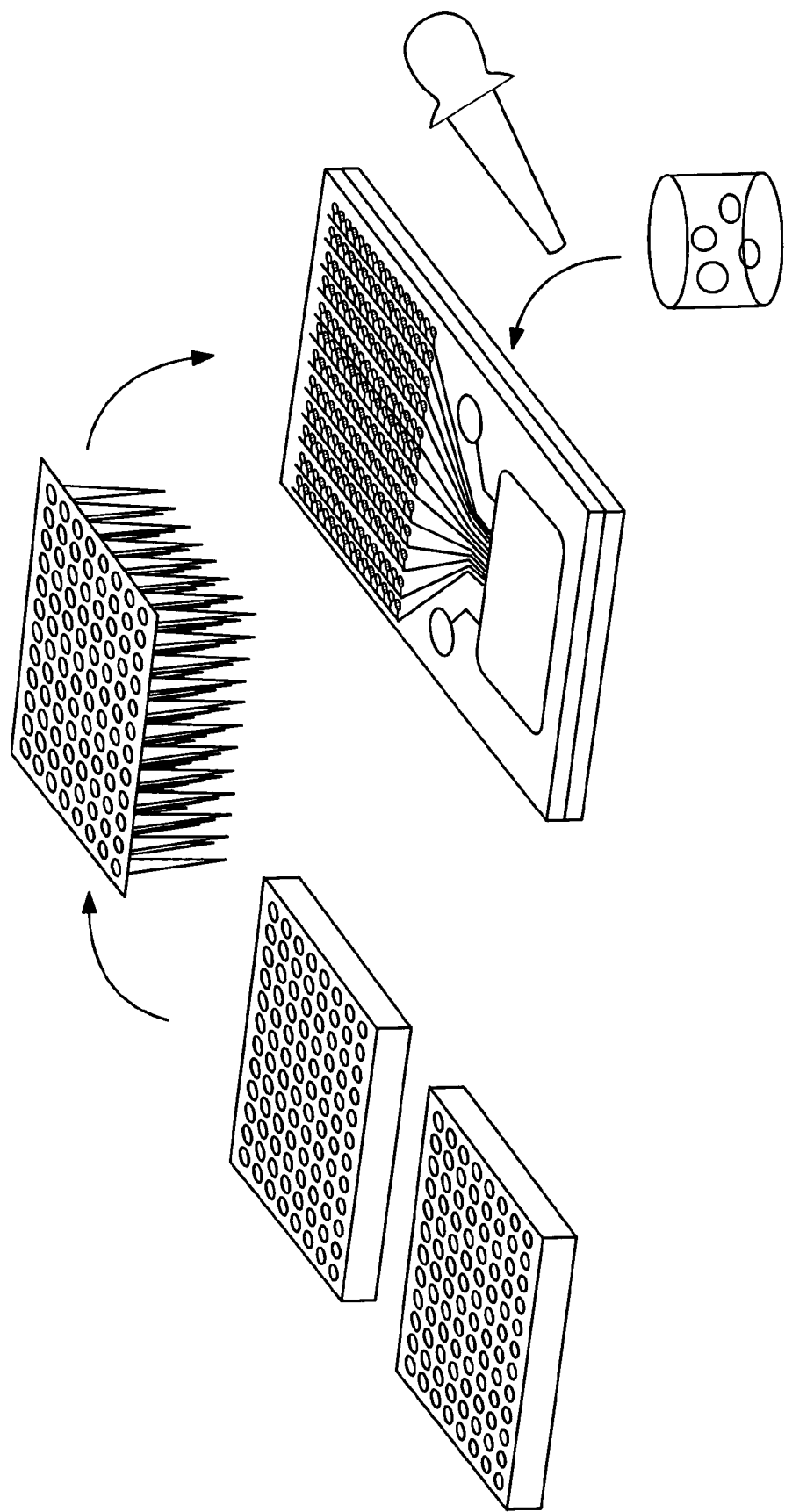
FIG. 3 is a perspective view of a kit in accordance with one aspect of the invention illustrating a process for dispensing fluids from 96-well plates onto a microfluidic chip comprising interdigitating reservoirs using automated array pipettors and cell delivery using a pipette.

FIG. 3 illustrates how sample solutions can be transferred from the wells of a 96-well plate into reservoirs on a chip according to one aspect of the invention using traditional robotic automated array pipettors. For a microchip with interdigitated ligand and buffer reservoirs (e.g., as shown in FIG. 2B), buffer solution can be transferred from a bath, where only one buffer is needed, or from a 96-well plate, with wells comprising the same or different buffers.

Figure 2C:
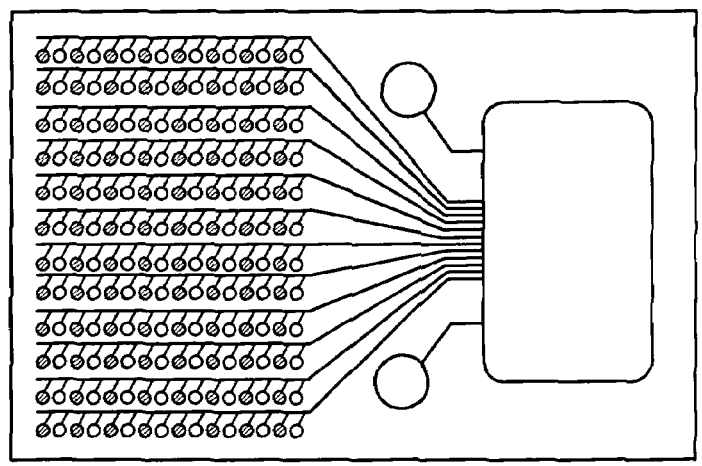

In addition to the reservoirs needed for interfacing with sources of sample and/or buffer (e.g., such as well plates), there may be additional reservoirs placed on the chip for storing and transferring cells or other samples of interest. FIG. 2C illustrates the possible placement of additional reservoirs and microchannels for storing and transporting cells into reservoirs or the sensor chamber of the chip, according to one aspect of the invention.

The cell chambers can be adapted for performing on-chip manipulation of cells. In one aspect, the chip provides one or more cell treatment chambers for performing one or more of: electroporation, electroinjection, and/or electrofusion. Chemicals and/or molecules can be introduced into a cell within a chamber which is in electrical communication with a source of current. For example, one or more electrodes may be placed in proximity to the chamber, or the chamber can be configured to receive an electrolyte solution through which current can be transmitted, for example, from an electrode/capillary array as described in WO 99/24110, the entirety of which is incorporated by reference herein.

Suitable molecules which can be introduced into a cell in the cell treatment chamber include, but are not limited to: nucleic acids (including gene fragments, cDNAs, antisense molecules, ribozymes, and aptamers); antibodies; proteins; polypeptides; peptides; analogs; drugs; and modified forms thereof. In a preferred aspect, the system processor controls both the delivery of molecules to the one or more cell treatment chambers (e.g., via capillary arrays as described above) and incubation conditions (e.g., time, temperature, etc.). For example, a cell can be incubated for suitable periods of times until a desired biological activity is manifested, such as transcription of an mRNA; expression of a protein; inactivation of a gene, mRNA, and/or protein; chemical tagging of a nucleic acid or protein; modification or processing of a nucleic acid or protein; inactivation of a pathway or toxin; and/or expression of a phenotype (e.g., such as a change in morphology).

The treated cells can be used to deliver molecules of interest to the sensor in the sensor chamber, e.g., exposing the sensor to secreted molecules or molecules expressed on the surface of the cells. In this aspect, the system can be programmed to release a cell from a cell treatment chamber into a channel of the system intersecting with the sensor chamber, thereby exposing a sensor in the sensor chamber to the molecule of interest.

Alternatively, or additionally, when the system is used in conjunction with a cell-based biosensor, the cell treatment chamber can be used to prepare the biosensor itself. In one aspect, a cell is delivered from the treatment chamber to a channel whose outlet intersects with the sensor chamber. In one aspect, the scanning mechanism of the system is used to place a micropositioner in proximity to the outlet so that the micropositioner can position the cell within the sensor chamber. In another aspect, fluid flow or surface tension is used to position a cell in a suitable position. For example, the system can be used to deliver the cell to the opening of a pipette which is part of a patch clamp system.

In another aspect, a cell can be delivered to the sensor chamber to periodically replace a cell-based biosensor in the sensor chamber. In this aspect, the cell can be untreated, e.g., providing a substantially genetically and pharmacologically identical cell (i.e., within the range of normal biological variance) as the previous sensor cell. Alternatively, the replacement cell can be biochemically or genetically manipulated to be different from the previous sensor cell, to enable the system to monitor and correlate differences in biochemical and/or genetic characteristics of the cells with differences in sensor responses. The biochemical or genetic difference can be known or unknown.

The system can be programmed to deliver cells from the cell treatment chamber at selected time periods based on control experiments monitoring uptake of chemicals and molecules by cells. Alternatively, the system can monitor the phenotype of cells and deliver cells when a certain phenotype is expressed. For example, in one aspect, the cell treatment chamber is in communication with an optical sensor which provides information relating to optical properties of the cell to the system processor, and in response to optical parameters indicating expression of a particular phenotype, the system can trigger release of the cell from the cell treatment chamber. Optical parameters can include the uptake of a fluorescent reporter molecule or optical parameters identified in control experiments.

The combination of on-chip electroporation with microfluidics and patch clamp (or other methods for monitoring cell responses) facilitates screening for molecules (e.g., ligands or drugs) which modulate the activity of intracellular targets. In one aspect, the system is used to deliver a cell-impermeant molecule into the interior of a cell by transiently electroporating the cell. In this way, the molecule can be introduced to intracellular receptors, intracellular proteins, transcriptional regulators, and other intracellular targets. The cell can be delivered to the sensor chamber and the response of the cell can be monitored (e.g., by patch clamp or by fluorescence, if the molecule is tagged with a fluorescent label). Alternatively, the sensor chamber can be modified to perform both treatment and response detection.

In a further aspect, the system can be modified to perform electroporation by scanning. For example, a cell can be repeatedly electroporated as it is being translated or scanned across a plurality of different fluid streams containing different compounds. In one aspect, pores are introduced into one or more cells as they come into contact with a sample stream, enabling compounds in the sample stream to be taken up by the cell.

Rapid Alterations of the Solution Environment Around a Sensor

Central to the present invention is the use of two-dimensional (2D) and three-dimensional (3D) networks of microfabricated channels for the complex manipulation of compounds or reagents contained in the fluid in a way that permits repeated and rapid delivery of different solutions to the sensor in the sensor chamber. For example, the microfluidics used with the system enables the system to programmably deliver a ligand to a cell-based biosensor comprising a receptor. This enables the system to be used for HTS screening of samples (e.g., such as compound libraries) to monitor the effects of compounds on the responses of the biosensor. In one aspect, electrical properties of a cell-based biosensor are monitored using voltage clamp or patch clamp techniques.

Because the system provides a scanning mechanism for changing the position of channels relative to a sensor, the system can be used to flush a cell-based biosensor with buffer after exposure to a sample compound, enabling a receptor or ion channel that is part of the biosensor to be resensitized prior to exposure to the next compound. Thus, the system can provide a periodically resensitized receptor for exposure to potential modulators of receptor function (e.g., such as agonists or antagonists). For receptors that do not desensitise, the system is still advantageous for providing pulsed delivery of buffer to a receptor, e.g., to remove unbound ligand from the receptor, to enhance the specificity and/or decrease background of a response.

The geometry of different network structures of microchannels is designed to exploit the unique characteristic of fluid behavior in micro-dimensions. Three exemplary designs are described below.

The first design relies on the system's ability to transport one or more sensors, rapidly across different streams of fluid flowing from channel outlets by translating the sensors across the channels or by translating the substrate comprising the channels relative to the one or more sensors. The system also can sweep different fluid streams across a stationary sensor by varying pressure drops across individual channels of the substrate. This design is derived from the discovery of a new and unique fluidic behavior; i.e., that lateral interactions and couplings between neighbouring fluid streams as they exit from a set of closely spaced microchannels into an open volume can extend dramatically the distance over which these streams remain collimated. The second design exploits the reversibility of fluid behavior at low Reynold's numbers while the third design is based on the ability to rapidly exchange fluids in microchannels and chambers.

The theme that runs through these designs is a microfluidic-based approach for rapidly and efficiently altering the local solution microenvironment in which one or more biosensors reside, providing complete or near-complete solution exchange. The system requires small sample volumes (nLs to µLs) and can be easily automated and programmed for HTS applications.

(1) The Rapid Transport of Sensors Across Different Streams of Fluids

Adjacent fluid streams exiting the plurality of microchannels of a substrate according to the invention have a low Reynold's number and undergo minimal mixing by diffusion. For example, a small molecule with a diffusion coefficient of about $5 \times 10^{-6}$ cm$^2$/s would take approximately 0.1 seconds to diffuse 10 µm, but 10 s to diffuse 100 µm, owing to the square dependence of distance on diffusion time ($x^2 = 2Dt$, where D is the diffusion coefficient). Similarly, for typical proteins having $D \sim 10^{-6}$ cm$^2$/s, it will take 0.5 second to diffuse 10 µm and 50 seconds for 100 µm.

However, flow rates in microchannels can vary dramatically from many meters per second to micrometers per second. The flow rate in the present system is limited to the maximum flow rate that can be used without disturbing the activity of the sensor. For example, when using a patch clamp sensor, flow rate is typically on the order of hundreds of µm/s to mm/s for a patch-clamped cell (see below for discussion), in order to prevent dislodgement of the patch-clamped cell from the pipette which positions it at a channel opening.

Flow Profiles of Multiple Fluid Streams Exiting into the Sensor Chamber

Figure 16A:
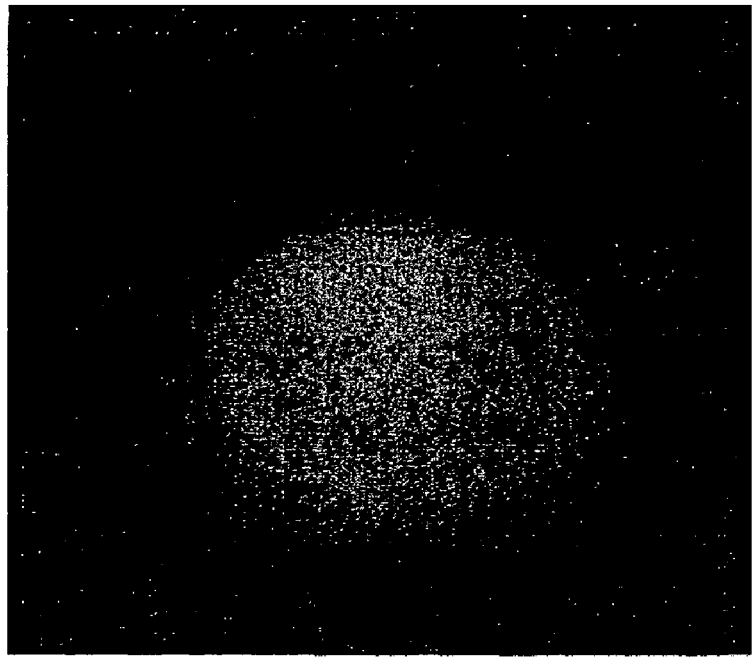
FIGS. 16A and B are microphotographs showing flow profiles at the outlet of a single microchannel (FIG. 16A) and an array of microchannels (FIG. 16B). Fluid flow was imaged under fluorescence using a fluorescent dye (fluorescein) as a flow tracer. The channels were 100-μm wide, 50 μm thick, with an inter-channel spacing of 25 μm; the flow rate was 4 mm/s.
Figure 16B:
Figure 17:
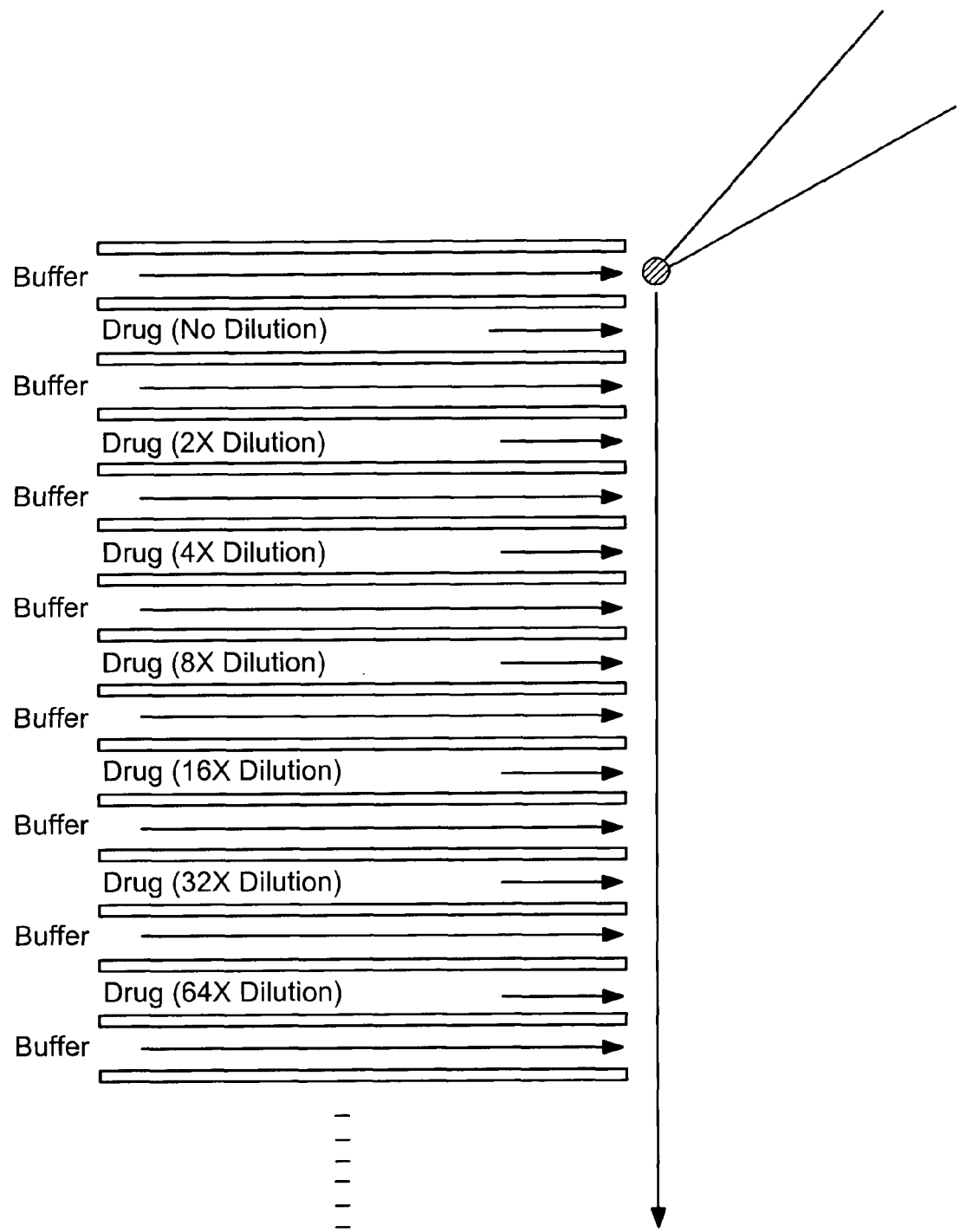
FIG. 17 is a schematic illustrating the arrangement of the outlets of an interdigitating array of microchannels in which varying dilutions of a sample (e.g., a drug) are provided in every other microchannel. By scanning a patch-clamped cell across the outlets of the channels, dose-response measurements can be obtained.

When a plurality of microchannels is used, an understanding of the flow profile of the multiple streams of fluid at the interface between the outlets of the microchannels and the open-volume reservoir is essential. FIGS. 16A and 16B show photomicrographs of flow profiles of a fluid comprising 500 µM of a fluorescent dye (fluorescein) from a single channel (FIG. 16A) and multiple channels (FIG. 16B). Excitation of the fluorescent tracer was carried out using the 488-nm line of an Argon Ion laser in an epi-illumination configuration and fluorescence of the tracer was collected and imaged using a CCD camera. As shown in FIG. 16A, in the absence of adjacent microchannels and fluid streams, the fluid exits the single channel and disperses at the channel outlet in a semicircular fashion. FIG. 16B shows a flow profile of interdigitated buffer and fluorescein fluid streams exiting from a plurality of channel outlets. The dimensions of microchannels were 100 µm wide, 50 µm thick, with an interchannel interval of 25 µm. The flow rate in the microchannels in both FIGS. 16A and 16B was 4 mm/s.

As shown in FIG. 16B, the fluid stream exiting multiple microchannels into an open volume is collimated for at least a distance that is about 4-5 times the width of the microchannels (e.g., about several hundred micrometers) at a flow rate of about 4 mm/s. In this range of low flow rates (i.e., mm/s), the rate of fluid flow is still much faster than diffusion. For example, at a flow rate of mm/s, channel width of 10 µm, and channel intervals (the space between channels) of 10 µm, different streams of fluid containing small molecules ($D=5 \times 10^{-6}$ cm$^2$/s) exiting different channel outlets will not be fully mixed until at a distance of at least about 0.4 mm downstream of the channel outlets. This is more than sufficient for making measurements of a typical mammalian cell having a diameter of about 10 to 20 µm which is placed 10 to 20 µm outside the outlet of a channel. Since diffusion time varies with the square of the distance, doubling the width and spacing of microchannels to 20 µm extends the downstream distance at which the cell can be placed to at least about 1.6 mm. The average linear velocity of the flow will vary depending on the exact application, with typical flow rates ranging from about 100 µm/s to about 10 mm/s for a 10 µm cell. Thus, a sensor can be scanned across substantially distinct and separate aqueous streams of fluid which exit from the microchannel outlets.

At the preferred flow rates for use with patch clamp measurements and at a cell-to-outlet distance of about 20 µm or less, the different fluid streams are essentially distinct and separate and are undisturbed by the presence of a patch-clamped cell. Even at much lower flow rates (e.g., <100 µm/s) that may be used with patch clamp measurements, different fluid streams are still well separated. This observed behaviour (e.g., collimation of fluid streams) of fluid flow at the exits of microchannels into an open volume sensor chamber facilitates HTS applications which require relatively rapid translation of patched cells with respect to different fluid streams. Spacing between microchannel outlets can be optimised to optimise separation between fluid streams, as can flow rate. For example, the more rapid the flow rate, the less mixing is observed. Preferably, flow rate and interchannel spacing are optimised to minimize the width of a boundary zone (i.e., an area of mixing). Preferably, a boundary zone is less than about 50% of the width of a fluid stream, or less than about 40%, less than about 30%, less than about 20%, less than about 10%, less than about 5%, or less than about 1% of the width of the stream. In one aspect, the boundary zone is about 2-3 microns. Optimal fluid flow rates and interchannel spacings can be devised readily using one or more tracer dyes as described above.

To exploit the unique behaviour of fluid flow into open volumes, the pressure applied to each of a plurality of microchannels can be individually varied for precise manipulation of each flow stream. For example, in the extreme case in which positive pressure is applied to one channel and negative pressure is applied to an adjacent channel, the fluid stream can be made to make a "U-turn", going from the channel with positive pressure to the one with negative pressure while drawing in a sheath of buffer into the channel with negative pressure. Therefore, the position, width, collimation, direction, and rate of flow, as well as the composition of the fluid streams, can be controlled by varying the relative pressure applied to each channel.

As shown in FIG. 5D-F, this can be used to create a U-shaped fluid stream which has the advantage that sample delivered onto a cell from a channel experiencing positive pressure can be withdrawn into a waste channel experiencing negative pressure. This minimizes the accumulation of ligands in the open volume where the patch-clamped cell resides. In situations where a sample (e.g., a drug, ligand, and the like) is in low concentration and/or is expensive, the system further can be used to recycle ligand and/or to feed ligand back into the system (i.e., the U-shaped stream can be turned into a closed loop).

By controlling pressure, the system can control the velocity (both amplitude and direction) of fluid streams. Velocity control also may be exercised by controlling the resistance of each channel without changing the pressure or by changing both resistance and pressure. Fluid shear also can be varied by using solutions of different viscosity (e.g., adding different amounts of a sugar such as sucrose to a fluid stream) in both the microchannels and sensor chamber. Thus, by varying a number of different parameters, the flow profile of different fluid streams can be precisely tuned.

Patch Clamp Under Fluid Flow

The ability to rapidly scan patch-clamped cells across interdigitated streams of receptor modulators (agonists or antagonists) and buffer depends on the mechanical stability of the patched cell under the required flow conditions as well as scan speeds. Here, the stability of the "giga seal" and ion-channel activities of patch-clamped cells under a range of flow conditions is described.

The effects of liquid flow on a patch-clamped cell arise from the force (Stokes drag) exerted by the flow on the cell. This Stokes drag can be calculated from the following equation:

Force=(frictional coefficient)×(velocity of the flow)

Where the frictional coefficient (f) can be calculated from:

$f=6\pi r\mu$ where r is the radius of the cell and µ is the viscosity of the solution. This relationship is valid for low Reynold's number flow and for particles that are spherical. Both conditions are adequately met in the methods and devices utilized in connection with the present invention.

For water at room temperature, µ is ~1 centipoise (1 centipoise=0.01 g/[cm s]) and for a typical mammalian cell, r=5 µm. Using these values and for flow rates of 1 mm/s, Force=$9.4 \times 10^{-11}$ N or 94 picoNewtons. Since force is linearly proportional to the flow rate, at 0.1 mm/s, Force is 9.4 picoN. To put this number in perspective, micropipettes can routinely exert nano- and micro-Newtons on a small particle such as a cell. In addition to the force that arises owing to the drag on the cell from fluid flow, the scanning of the cell at a certain velocity exerts a similar drag force in the direction of cell translation, which is typically orthogonal to the direction of fluid flow. Scanning of a cell at 1 mm/s under no flow typically has the same effect as keeping the cell stationary while flowing the fluid at the same rate.

For applications that require extremely high flow rates in which cell dislodgement may become an issue, patch-clamped cell(s) may be put into a recessed region or well in the sensor chamber that matches the dimension of the cell. This design will permit the use of high flow rates while preventing cell dislodgement because the flow profile in a channel or chamber is parabolic, owing to no-slip boundary conditions at the interface of a fluid and a solid surface (i.e., the velocity at the interface of the fluid and the solid surface is zero). By placing cell(s) in well(s) having similar dimensions as the cell, the cell is essentially "shielded" from the high velocity flow region that is located away from the well and the solid surface. Therefore, although the average flow rate and the flow velocity away from the solid surface can be extremely high, the flow velocity near the well in which the patched cell is placed can be very small. By using this strategy, very high average flow rates can be used.

As discussed above, fluid flow also can be used to maximize the sensitivity of patch clamp. As shown in FIG. 5D-F, a U-shaped fluid stream created by two parallel channels can be used to create an optimal seal between a cell and a patch clamp micropipette.

Scanning Mechanisms

Scanning can be mediated mechanically (by moving the substrate while the sensor is stationary or by moving the sensor while the substrate is stationary or by moving both the substrate and sensor at different speeds and/or in different directions) or by pressure drops across different microchannels. FIGS. 8A-I schematically depict how each of these methods may be carried out. The mechanical movement and scanning of a sensor can be readily accomplished by translating a micropositioner positioning the sensor. For example, a cell-based biosensor can be physically attached to a micropipette by suction, which in turn is attached to a micromanipulator. Most micromanipulators can be controlled manually as well as actuated electronically, so preprogrammed movement can be easily achieved. A number of parameters that can be programmed, include, but are not limited to, the linear velocity for constant velocity scans; accelerations for variable velocity scans; trajectories of the scan, both in two dimensions and three dimensions; and the number of repeated scans. For scans based on real-time signal feedback from one or more sensors in the sensor chamber, programmable parameters include, but are not limited to, the time delay between signal detection and the change of scan settings. A variety of signal processing and computational functions can be performed to determine correct feedback parameters to output for the scan.

The mechanical movement and scanning of a platform on which the substrate (e.g., a chip) is resting also can be readily achieved, thereby moving the substrate relative to a stationary biosensor. For example, computer-controlled microscope stages with different designs (e.g., ones based on piezo-electric crystals, or electronically actuated thread screws) and having the needed specifications are commercially available (for example, from Prior Scientific Inc., 80 Reservoir Park Drive, Rockland, Mass.). Suitable scanning parameters can be programmed using the system processor which is in communication with the platform, e.g., in response to user directions or feedback signals from one or more sensors in the sensor chamber, as described above.

In one aspect, one or more sensors are moved rapidly over the distance between the outlets of closely spaced channels in the sensor chamber, exposing the one or more biosensors in the chamber to different streams of fluid exiting the outlets. For example, the sensor can be a cell or a membrane patch attached to a micropipette which is programmed to move across the outlets of the channels. In another aspect, one or more stationary cells are immobilized in the sensor chamber (e.g., in a planar-patch clamp format) and different streams of fluid are made to sweep over the stationary cell(s), e.g., by adjusting pressures and flow rates at each individual channel through which the different streams exit. Alternatively, channel outlets can be moved physically past a stationary cell as described above.

Because the aqueous solutions flowing through the channels are non-compressible (unlike air), the width and placement of each fluid stream depends on the relative flow rate through each microchannel. Therefore, fluid streams from the microchannels also can be made to move and translate by varying the flow rate through each channel. This is most easily achieved by controlling the pressure drops across each channel or by changing the resistance of each channel. The ability to move fluid streams by pressure variations (or other means) is particular useful in applications in which the sensor(s) are cell-based and are immobilized on the chip, such that such that mechanical movements of the cell(s) relative to the chip are not possible. As with mechanical scanning, the pressure and resistances of each channel can be programmed, using the system processor. Parameters which can be programmed include, but are not limited to, linear changes in the pressure and resistance of each channel, stepwise or constantly variable changes in the pressure and resistance of each channel, and the sequence of changes among the different channels. In addition, pressure and resistance changes can be based on real-time feedback signals, and these signals may be processed and computed prior to outputting new pressure and resistance parameters.

Scanning speed can be adjusted depending on the application. For example, when the sensor comprises a receptor which is desensitized upon continued exposure to an agonist, the sensor can be moved from a sample-containing stream to a buffer-containing stream to allow the receptor to resensitize. By sequentially sweeping a sensor across sample streams and buffer streams (mechanically or through pressure differentials), pulsed delivery of agonist and buffer can be provided, thereby generating a periodically resensitized receptor.

Scanning speed can be adjusted in this scenario to accommodate the amount of time necessary for resensitization, which, in the case of an ion channel, is often on the order of milliseconds (depending on ligand-ion channel pair). In general, the exposure time of the sensor to solution can be controlled and can range from microseconds to hours. For drug-receptor pairs having long equilibration times, however, throughput may be limited by the length of equilibration time. Similarly, the responses of a cell-based biosensor may depend on transduction of a signal through a biochemical pathway, which can require from milliseconds to longer intervals (e.g., minutes). Scan rates therefore will be adjusted to accommodate the type of sensor being used and can be determined readily from control experiments, such as time course experiments.

Preferably, therefore, the scanning mechanism (whether it moves the sensor, or the chip, or acts by controlling pressure drops across channels) is controlled by the system processor to move the position of the sensor relative to the chip, at a user-selected or system-selected rate. For example, a user can implement a system program which alters translation parameters of the scanning mechanism, e.g., by selecting an action button on a graphical interface displayed on a computer in communication with the system processor. Alternatively, scanning rates can be modified by the system processor in response to a feedback signal (e.g., such as a patch clamp recording of a cell indicating desensitization). The scanning mechanism can be programmed for linear or stepwise scanning (e.g., moving a sensor to a channel outlet which is not adjacent to the previous outlet to which the sensor was exposed).

A sensor may comprise a receptor/ion channel which does not desensitize, eliminating the need to resensitize the receptor. However, the system may still be used to provide pulsed delivery of buffer, for example, to wash a cell free of unbound compounds. In this scenario, the scan rate can be adjusted based on "noise" observed in the response. For example, the scan rate can be adjusted to achieve a linear dose-response over certain concentrations of sample compound.

A ligand also may irreversibly block a sensor, rendering it unresponsive to other ligands in other fluid streams. In this case, pulsing with buffer will have no effect. It is straightforward to ascertain whether the cell is inactivated by introducing compounds of known effect periodically to the cell and verifying whether an appropriate response is obtained. Preferably, the system is able to sense a lack of response by a sensor as it is scanned past a selected number of sample fluid streams. For example, the system can provide a feedback signal when no response is observed in patch clamp recordings over as a sensor is scanned past a selected number of consecutive fluid streams.

Alternatively, or additionally, devices can be provided in the sensor chamber to monitor sensor function. In one aspect, an optical sensor is provided in communication with the sensor chamber for monitoring the viability of a cell-based biosensor. For example, spectroscopic changes associated with cell death (e.g., such as from chromatin condensation) may be observed, or the uptake of a dye by a dead or dying cell can be monitored.

In one aspect, the system executes certain program instructions when a selected number of scanning intervals in which no sensor signal has been received have gone by. For example, the system can vary pressure at particular channels to stop flow in those channels, thereby minimizing sample waste. In another aspect, in response to an absence of a response signal from a sensor over a threshold period, one or more replacement biosensors are delivered to the sensor chamber (e.g., from the cell treatment chambers described above).

If a sensor is translated at a constant speed compared to flow rate from channel outlets (e.g., mm/s), then the screening rate (e.g., compounds screened per second) for channels having a width and spacing of about 10 μm will be approximately 25 Hz. Using about 100 μm wide channels with channel intervals of about 10 μm, the screening rate will be about 4.5 Hz. If the translation speed is increased, the scan range may be in the range of hundreds of Hz. For some applications, e.g., where the sensors comprise rapidly desensitizing ion channels, fluidic channels with narrow outlets are preferred as these can provide sharp concentration profile over short periods of time. Preferably, such channels range from about 1 μm to about 100 μm in width.

Scanning rates can be uniform or non-uniform. For example, scanning rates across channels providing sample streams (e.g., providing agonists) can differ from scanning rates across channels providing buffer streams. Variable scanning rates can be based on preprogramming or on feedback signals from the sensor measurements, e.g., such as from patch clamp measurements. The actual scan rate will vary depending on the exact screening system, but a typical linear scan rate will range from between about 100 μm/s to hundreds of mm/s for a sensor comprising a mammalian cell having a diameter of about 10 μm.

Figure 4A:
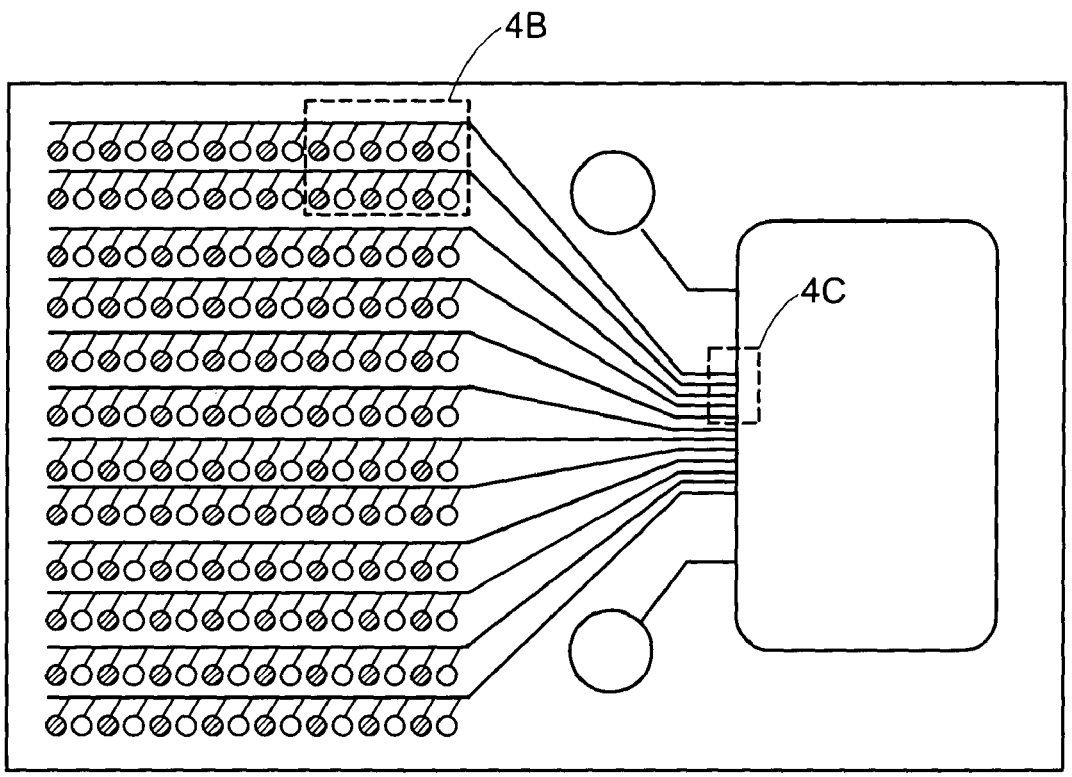
FIGS. 4A-C comprise a top view of a microfluidic chip structure for HTS of drugs according to one aspect of the invention, for scanning a sensor such as a patch-clamped cell or cells across interdigitated ligand and buffer streams.
Figure 4B:
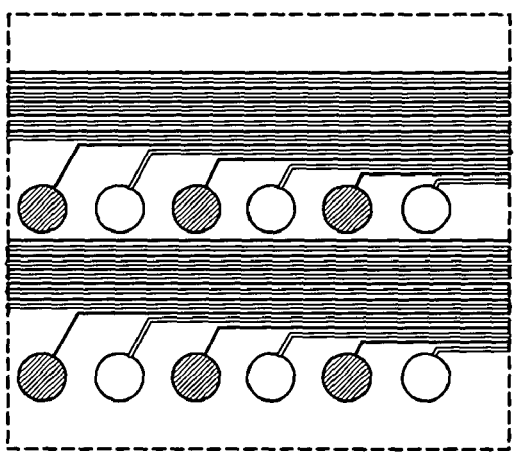
Figure 4C:
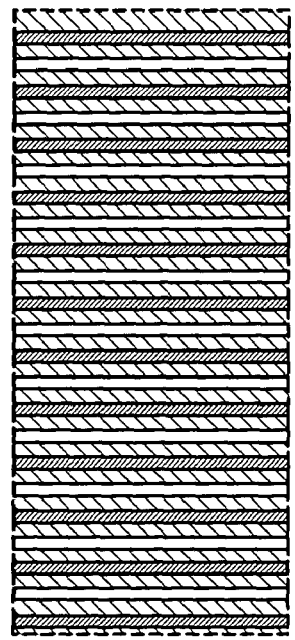
Figure 5A:
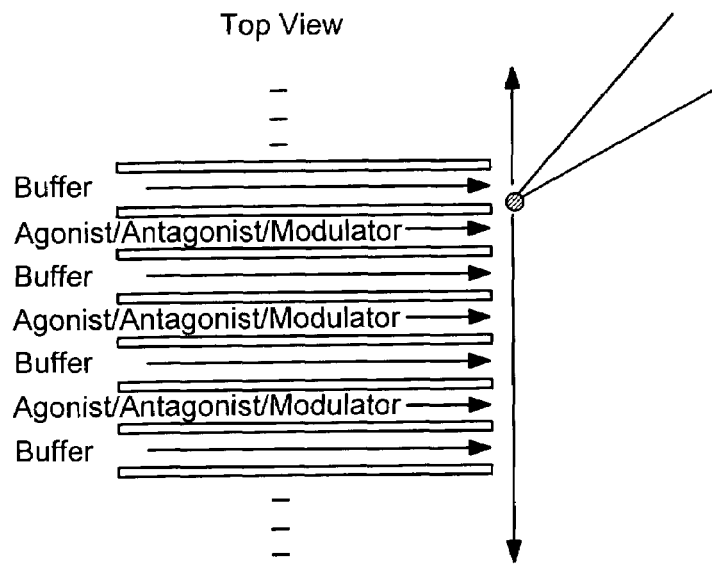
FIG. 5A schematically depicts a top view of the interdigitating channels of a microfluidic chip, with a patch-clamped cell being moved past the outlets of the channels.

A two-dimensional microfluidic system is shown in FIGS. 4A and 5A. The system comprises a substrate comprising a plurality of microchannels corresponding in number to the number of wells in an industry-standard microtiter plate to which the microchannels will be interfaced, e.g., 96 channels. When the system is used to provide alternating streams of sample and buffer to a sensor, at least 96 sample and 96 buffer microchannels (for a total of at least 192 channels) are provided. Wells of a microtiter plate, or of another suitable container, are coupled to reservoirs which feed sample or buffer to channels, e.g., for the system described previously, the substrate comprises 192 reservoirs, each reservoir connecting to a different channel. Additional reservoirs can be provided for cell storage and delivery, e.g., to provide cells for patch clamp recordings.

In the embodiment shown in FIGS. 4A and 5A, microchannels are substantially parallel, having widths of about 100 μm and thicknesses of about 50 μm. The exact thickness of channels may be varied over a wide range, but preferably is comparable to, or greater than, the diameter of the sensor, e.g., the diameter of a patched cell. In the Figure, inter-channel spacings of about 10 μm are provided.

Pressure can be applied simultaneously to all microchannels such that a steady state flow of solutions is made to flow through all microchannels at the same rate into the open volume that houses the sensor. In this way, steady state concentrations of different solutions containing ligands or pure buffer can be established at the immediate outlet of each of the microchannels. The width of each microchannel may be adjusted to achieve the desired flow rate in each microchannel.

Although the fluid streams exiting from the parallel channels enter an open volume sensor chamber in the embodiment discussed above, it may be more convenient and desirable to provide a set of parallel drain channels opposite the set of sample and buffer channels. A groove having an appropriate width (e.g., about 50 μm) can be placed in between, and orthogonal to, the two sets of channels (i.e., the delivery and drain channels) to accommodate scanning of a sensor in the sensor chamber. To establish an appropriate flow profile, a negative pressure may be applied to all the drain channels while simultaneously applying a positive pressure to the delivery channels. This induces fluid exiting the delivery channels to enter the set of drain channels.

Figure 5B:
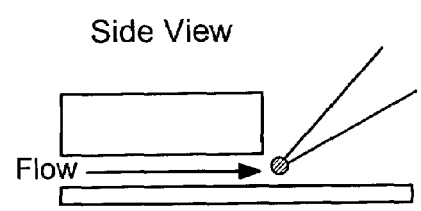
FIGS. 5B and 5C depict side views of alternate embodiments of the outlets and microchannels.
Figure 5C:
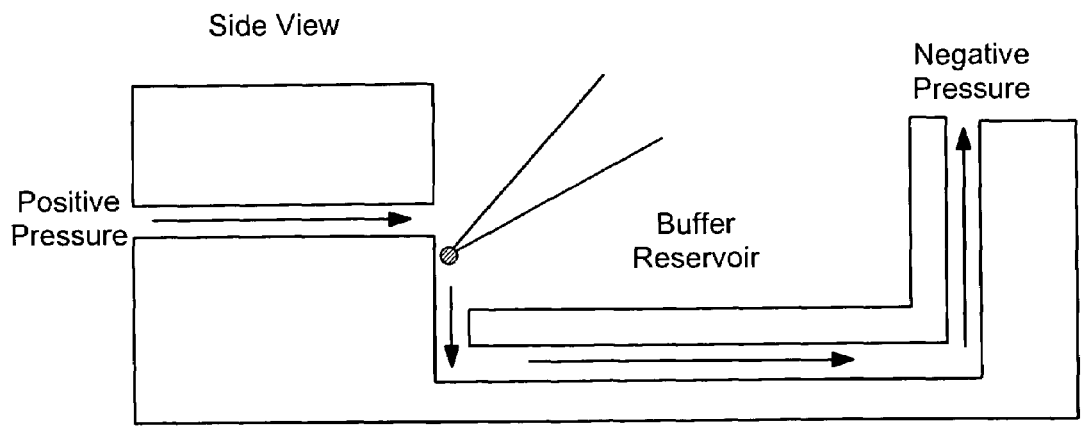

FIG. 5C shows a three-dimensional microfluidic system. The main difference between this 3D structure and the planar structure shown in FIG. 5B is the displacement along the z axis of fluid flowing between the outlet of the parallel array channels (e.g., interdigitated sample and buffer channels) and the inlet of the waste channels. In this embodiment, a positive pressure is applied to all sample and buffer channels while a negative pressure is simultaneously applied to all waste channels. Consequently, a steady state flow is established between the outlets of the sample/buffer channels and the inlets of the waste channels. In this configuration, a sensor, such as a patch-clamped cell, is scanned across the z-direction flow of fluid, preferably close to the outlet of the sample/buffer microchannels.

Although the fabrication of this 3D structure is more complex than the planar structure, the presence of z-direction flow in many cases will provide better flow profiles (e.g., sharper concentration gradients) across which to scan a sensor, such as a patch-clamped cell. The length over which z-direction flow is established should be significantly greater than the diameter/length of a sensor used. For example, the length of z-direction flow of a cell-based biosensor, such as a patch-clamp cell, should preferably range from about 10 µm to hundreds of µm.

Figure 7A:
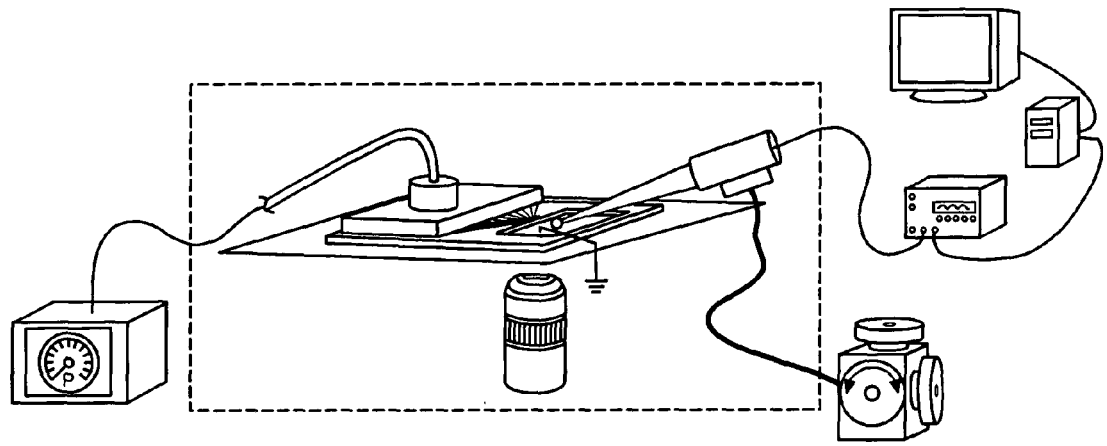
FIGS. 7A-N are schematics showing chip designs for carrying out cell scanning across ligand streams using buffer superfusion to provide a periodically resensitized sensor.
Figure 7B:
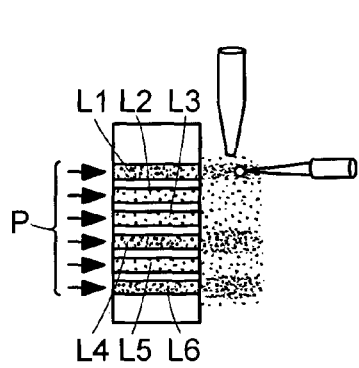
FIGS. 7B-G show enlarged views of the outlets of microchannels and their positions with respect to a superfusion capillary and a patch clamp pipette, as well as a procedure for carrying out cell superfusion while scanning a patch-clamped cell across different fluid streams. "P" indicates a source of pressure on fluid in a microchannel or capillary. Bold arrows indicate direction of movement.
Figure 7C:
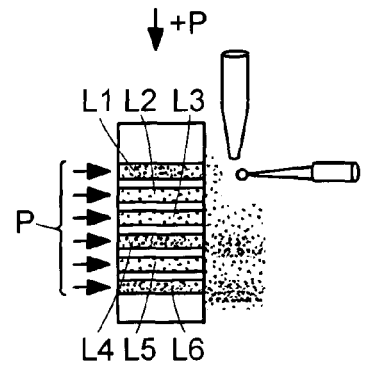
Figure 7D:
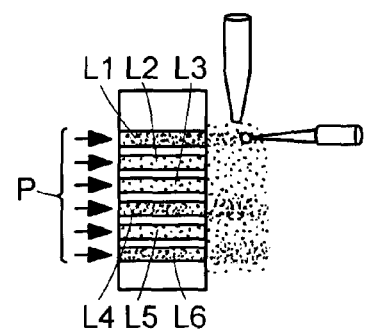
Figure 7E:
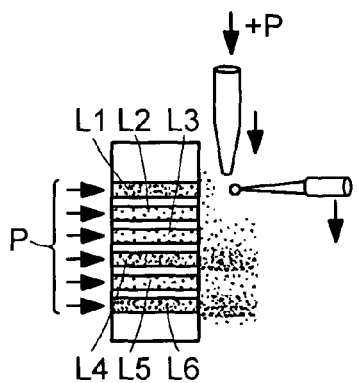
Figure 7F:
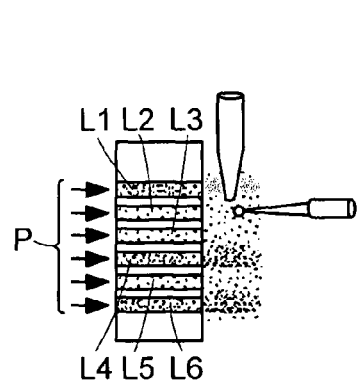
Figure 7G:
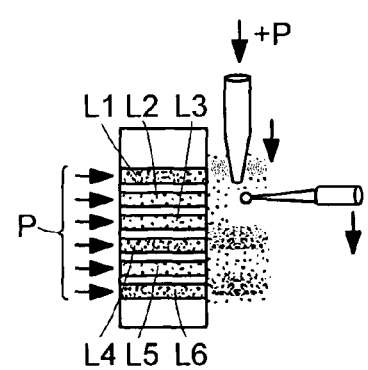
Figure 7H:
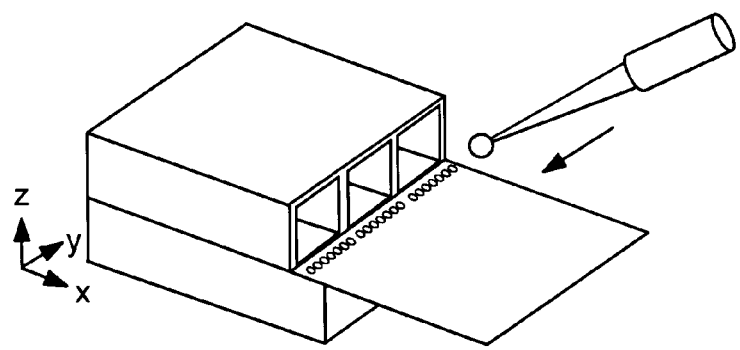
Figure 7I:
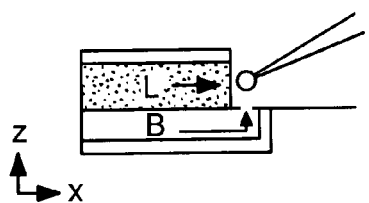
Figure 7J:
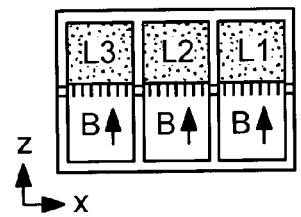
Figure 7K:
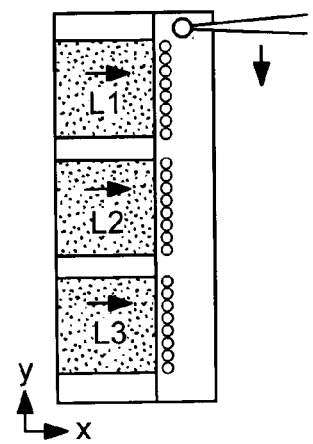
Figure 7L:
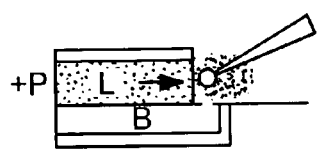
Figure 7M:
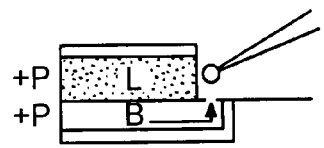
Figure 7N:
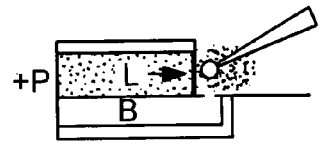
Figure 8A:
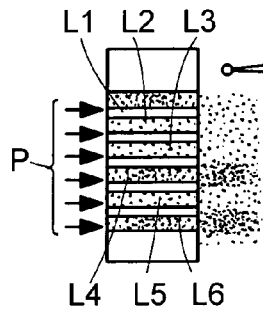
FIGS. 8A-I are top views of microchannel outlets in relationship to a patch-clamped cell, collectively showing different methods by which a patch-clamped cell can be moved in relation to the fluid streams.
Figure 8B:
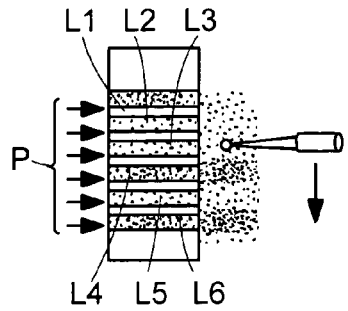
Figure 8C:
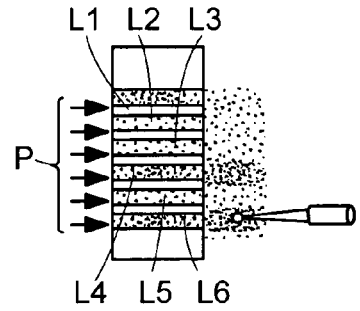
Figure 8D:
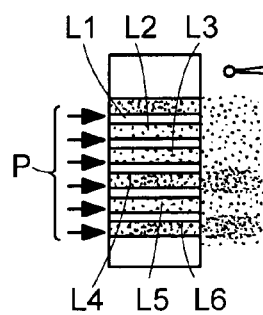
Figure 8E:
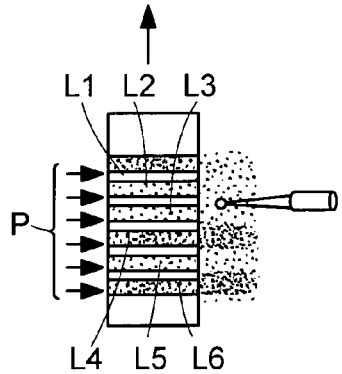
Figure 8F:
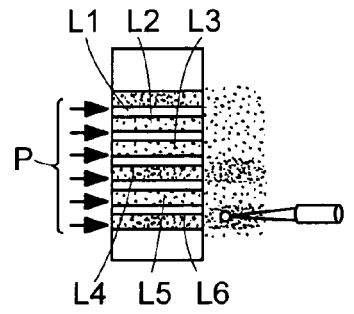
Figure 8G:
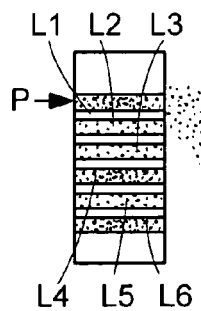
Figure 8H:
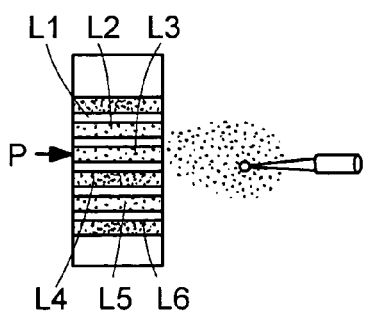
Figure 8I:
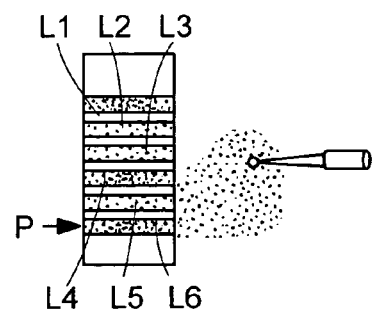

Another strategy for providing alternating sample streams and buffer streams, in addition to scanning, is shown in FIGS. 7A-N. In this embodiment, rather than providing interdigitating outlets which feed sample and buffer, respectively, into the sensor chamber, all outlet streams are sample streams. Buffer superfusion is carried out through one or more capillaries placed in proximity to one or more sensors. In FIG. 7A, the sensor shown is a patch-clamped cell positioned in proximity to an outlet using a patch clamp pipette connected to a positioner, such as a micropositioner or a nanopositioner or micromanipulator. A capillary is placed adjacent to the patch clamp pipette and can be used for superfusion, e.g., to resensitize a desensitized cell. By this means, a cell-based biosensor comprising an ion channel can be maintained in a periodically responsive state, i.e., toggled between a ligand non-responsive state (e.g. bound to an agonist when exposed to drugs) and an ligand responsive state (e.g. ligand responsive after superfusion by buffer).

Programmed delivery of buffer through this co-axial or side-capillary arrangement can be pre-set or based on the feedback signal from the sensor (e.g., after signal detection, buffer superfusion can be triggered in response to instructions from the system processor to wash off all bound ligands), providing pulsed delivery of buffer to the sensor. In one aspect, the longitudinal axis of the capillary is at a 90° angle with respect to the longitudinal axis of a patch clamp micropipette, while in another aspect, the longitudinal axis, is less than 90°.

Figure 6A:
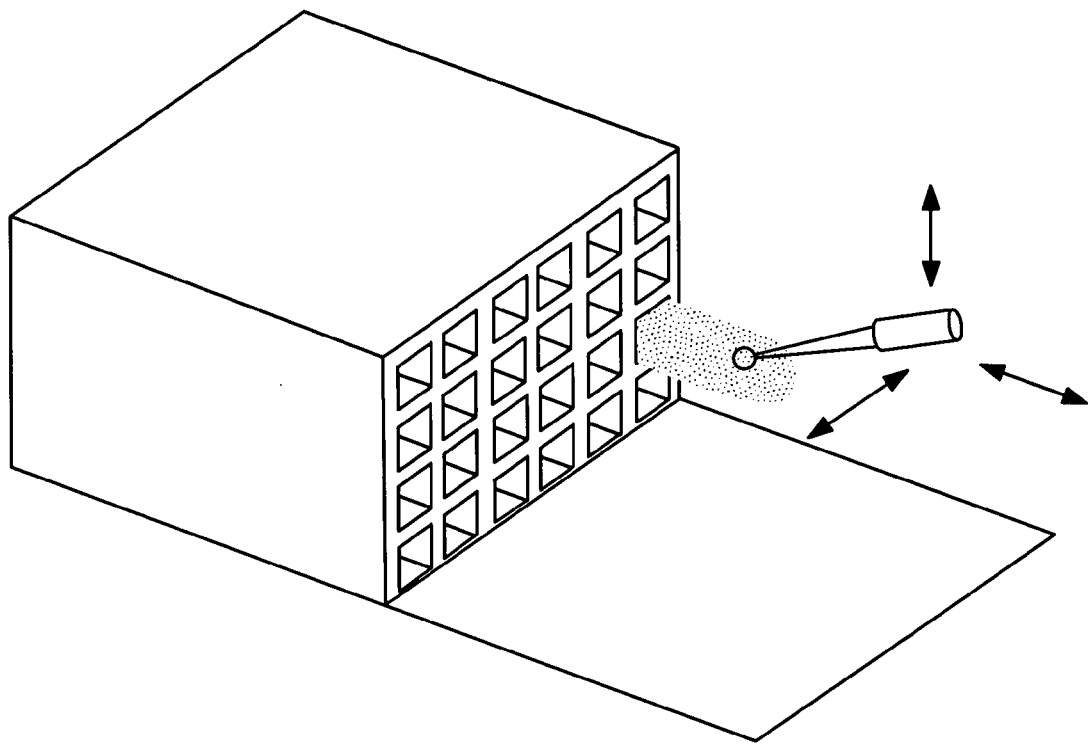
FIG. 6A is a perspective view showing a 3D array of microchannel outlet arrangements for increased throughput in HTS applications.
Figure 6B:
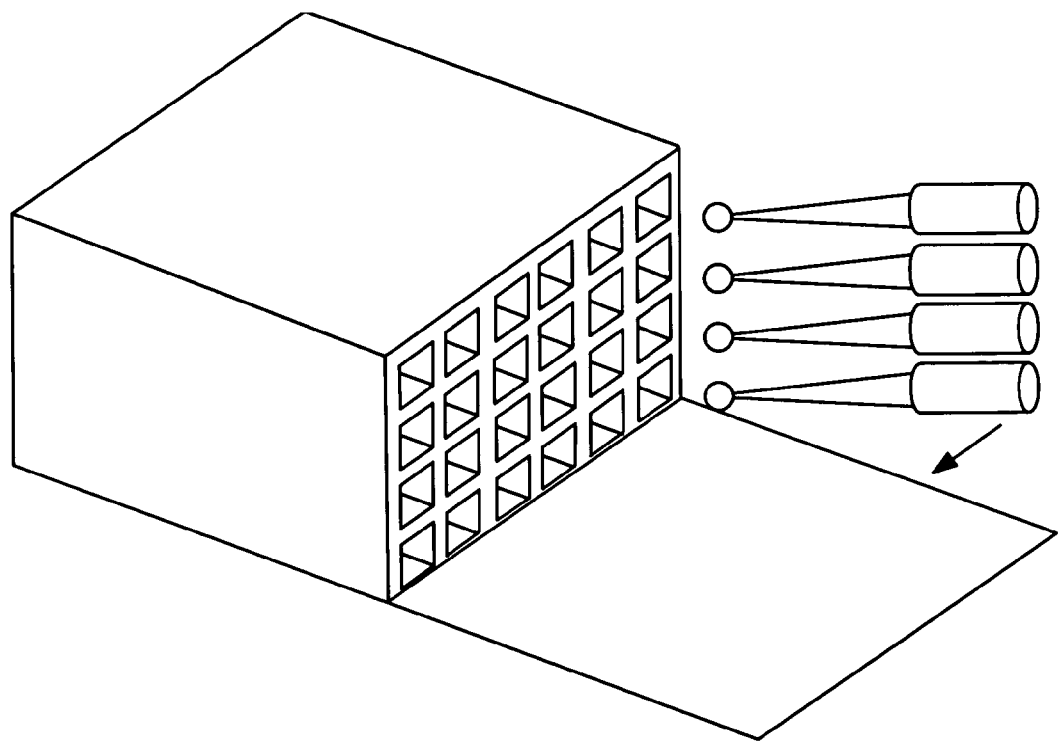
FIG. 6B depicts the use of a microchannel array as depicted in FIG. 6A, but with a plurality of patch-clamped cells. The arrows in the Figures indicate directions in which the patch-clamped cell(s) can be scanned.

Microchannel outlets themselves also may be arranged in a 3D array (e.g., as shown in FIGS. 6A-B). A 3D arrangement of outlets can increase throughput (e.g., increasing the number of samples that can be screened) and therefore increase the amount of biological information that the sensor can evaluate. In one aspect, the microfluidic system is used to obtain pharmacological information relating to cellular targets, such as ion channels.

There are several advantages to performing HTS in this format over the scanning format described in the preceding paragraphs: (1) ligand exposure time is determined by the inter-superfusion period (e.g., time between pulses of buffer) rather than by the scan speed and width of the ligand streams; (2) buffer superfusion and re-sensitization time also is determined by the duration of the superfusion pulse rather than by residence time in the buffer stream; (3) higher packing density of the number of ligand streams can be provided, thus resulting in the ability to scan a large number of ligands per experiment.

(2) Cycles of Rapid Delivery

Another feature of the system according to the invention is that fluid can be rapidly delivered through the channels into the sensor chamber, enabling compounds to be introduced into the microenvironment of a sensor and withdrawn from that microenvironment rapidly.

Fluid flows inside micron-sized channels are laminar and reversible, a property that can be gauged by a dimensionless number, called the Reynold's number (Re): For example, typically, fluid flow having a low Re number is reversible, while at high Re numbers, fluid flow becomes turbulent and irreversible. The transition between laminar reversible flow and turbulent flow appears to occur at a Re number of about 2000, an estimation based on flow through a smooth circular channel (e.g., approximating flow through a microchannel). Even at high flow rates (m/s), Re for channels measuring a few microns in width is ~<10. This means that fluid flow in micron-sized channels fall well within the laminar reversible regime. The key feature of fluidic behaviour exploited herein is the reversibility of fluid flow.

In one aspect, positive pressure is applied at a microchannel to introduce a compound or drug into the sensor chamber housing the biosensor, preferably a patch-clamped cell. After a suitable incubation time to allow interaction between the compound/drug and the biosensor, a negative pressure is applied to withdraw the compound/drug from the chamber. Because fluid flow is completely reversible and also because diffusion is negligible under conditions used (e.g., relatively fast flow), the drug is completely withdrawn from the chamber back into the microchannel from which it came. In this way, each compound delivered onto the cell to screen for potential interactions, can be subsequently withdrawn from the cell so the cell is again bathed in buffer, re-sensitized, and ready for interaction with the next compound delivered via a different microchannel.

Figure 9A:
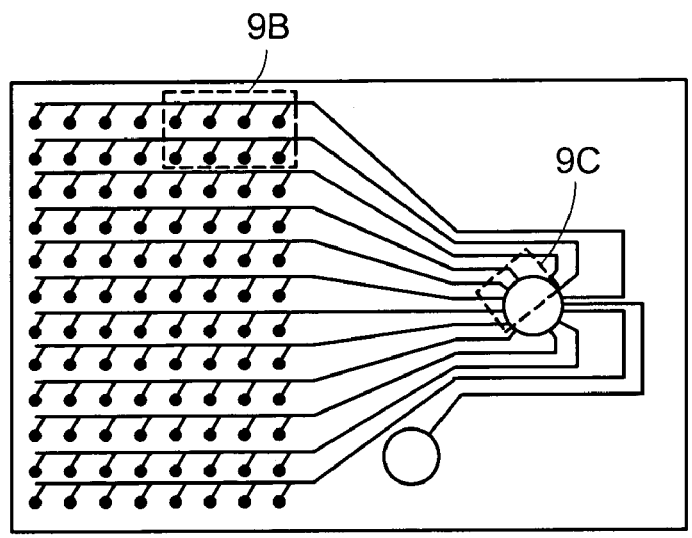
FIGS. 9A-C are top views of one design of a microfluidic chip for carrying out cycles of rapid delivery and withdrawal of compounds into and from a cell chamber for housing a patch-clamped cell.
Figure 9B:
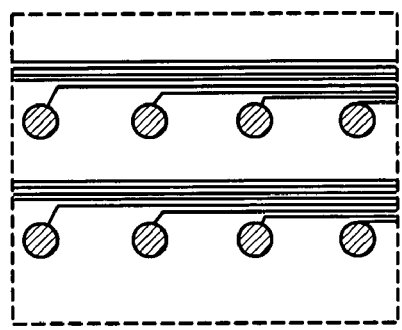
Figure 9C:
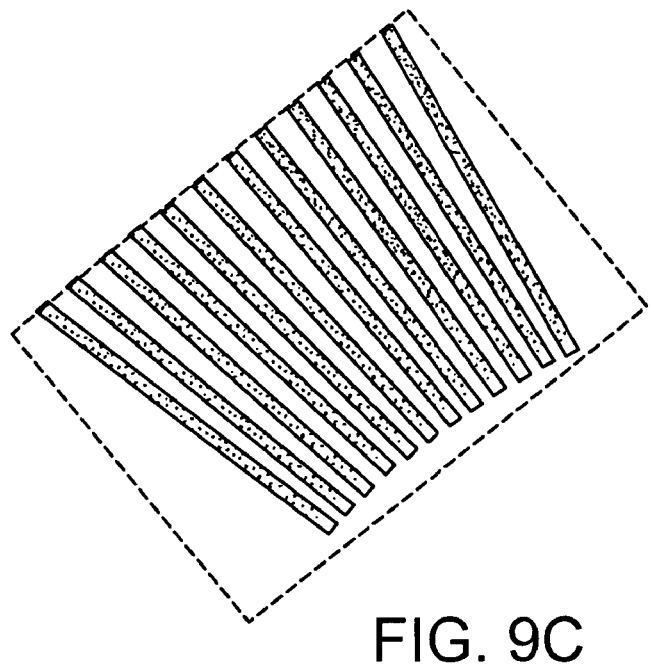

This scheme is particularly useful because of the small channel and chamber dimensions used in particular aspects of the invention. A number of channel geometries can be suitable to implement this scenario, particularly, the spokes-wheel configuration described above and shown in FIGS. 9A-C and 10. As can be seen from the Figures, an array of microchannels is arranged in a spokes-wheel format in which the microchannels converge in a circular sensor chamber at the center. The number of microchannels used depends on the number of sample wells in the sample-well plate to which the microchannels are to be interfaced. For example, a 96 sample-well plate will require at least 96 microchannels. The center sensor chamber can house one or more sensors, such as a patch-clamped cell, which can be patch-clamped using a micropipette or patch-clamped on a chip. FIGS. 9A-C show the layout of the overall chip structure for interfacing with a 96 sample-well plate, in which solutions from 96-well plates can be pipetted directly from a sample-well plate onto the corresponding reservoirs of the chip using standard array pipettors.

Figure 10:
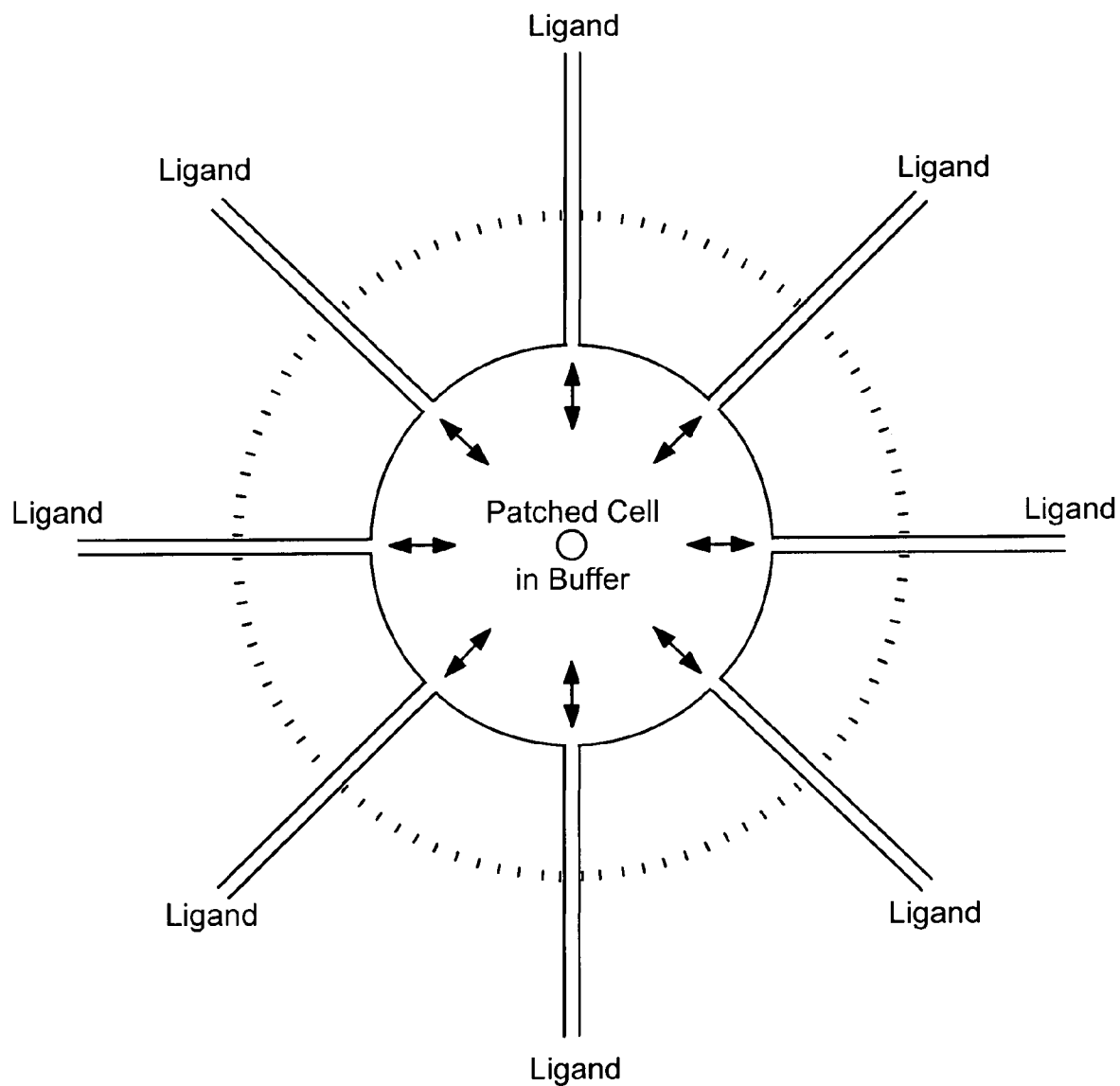
FIG. 10 is an enlarged top view of the cell chamber of FIG. 9A, depicting the arrangement of microchannels around a cell chamber comprising a patch-clamped cell.

FIG. 10 schematically depicts the enlarged region around the central chamber. The dimension of the chamber may vary depending on the exact application (e.g., whether the sensor comprises a cell or is another type of sensor), with typical diameters ranging from about 10 to hundreds of µm. The width of the microchannels will also vary depending on the diameter of the center chamber, with typical widths ranging from about 1 to about 20 µm. The thickness of the microchannels is less critical and will in most cases be range from about 1 to about 50 microns. Flow rates also can vary, with typical flow rates inside microchannels ranging from mm/s to cm/s and with corresponding flow rates in the open chamber across the sensor ranging from µm/s to mm/s. Positive and negative pressure applied to each of the microchannels can be controlled individually by the system processor such that positive pressure applied to one microchannel will cause its solution content to perfuse over the sensor while negative pressure will cause the withdrawal of this solution back to its respective microchannel, thereby leaving the biosensor bathed in its original buffer solution.

(3) Rapid Exchange of Fluids

This design relies on the fact that solutions contained in the microchannels and sensor chamber (and/or cell treatment chambers) can be rapidly and efficiently replaced and exchanged. Rapid solution exchange can be achieved using a variety of different microchannel network geometries. In one aspect, a plurality of microchannels converge or feed into the sensor chamber, while in another aspect, a plurality of microchannels converge into a single channel which itself converges into the sensor chamber. The plurality of microchannels can comprise interdigitating channels for sample and buffer delivery respectively. In a preferred aspect, the design is integrated with a patch clamp system. Three exemplary constructions are described below.

i) Planar Radial Spokes-Wheel Format

In this construction, a large number (e.g. 96-1024) of microchannels are arranged as radial spokes which converge into a chamber with dimensions ranging from about 10 μm to about 10 mm which houses the sensor. The number of microchannels used are selected to accommodate the number of sample wells in an industry-standard microtiter plate, e.g., 96 to 1024 wells. In addition to the number of microchannels that matches the number of inputs from the well plates, there are preferably, at least two additional microchannels, one for the delivery of buffer for superfusion/re-sensitization and the other for waste removal. For patch clamp using micropipettes, this construction also contains an open volume region for accessing the cell(s); however, for chip-based patch clamp measurements (such as described in WO 99/31503 and WO 01/25769), there will preferably not be any open volume regions. To prevent cell(s) from being dislodged by fluid flow from the microchannels, it is preferable that the cell(s) be placed in a recessed region or well that matches the dimensions of the cell(s). For membrane patches having dimensions much smaller than that of a cell, dislodging of patch by fluid flow is not an issue because the force exerted by Stokes drag is inversely proportional to the dimension of the object (i.e., patch).

In order to provide for efficient replacement of fluids contained in the chamber by incoming fluids from the channels, the angle between the input channel and waste channel is optimized. Fluid mixing and replacement is optimal when this angle is about 180° and gets progressively worse as this angle decreases towards 0 degrees. For high flow rates (cm/s to m/s), the effect of this angle becomes progressively more important, while for low flow rates, the angle between the input channel and waste channel is less important.

To maximize efficient replacement of fluids at high flow rates, the number of radial channels can be increased such that each input channel will have a corresponding waste channel, rather than having all input channels share a common waste channel. In this format, all angles between input and output channels are about 180 degrees, ensuring optimal fluid replacement. A second strategy is to construct a three-dimensional radial spokes-wheel channel network, while a third strategy involves the use of branched channel geometries. These strategies are described further below.

Figure 11A:
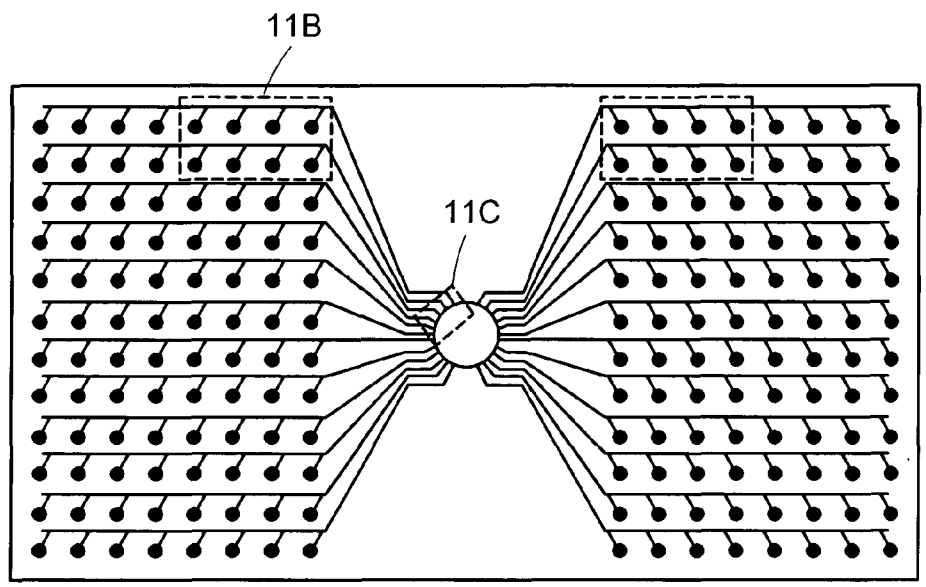
FIGS. 11A-C are top views showing a microfluidic chip for carrying out rapid and sequential exchange of fluids around a patch-clamped cell.
Figure 11B:
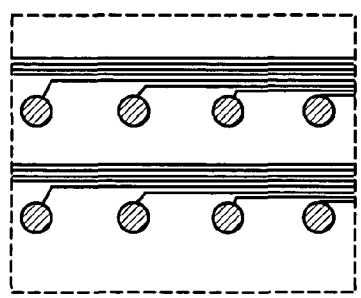
Figure 11C:
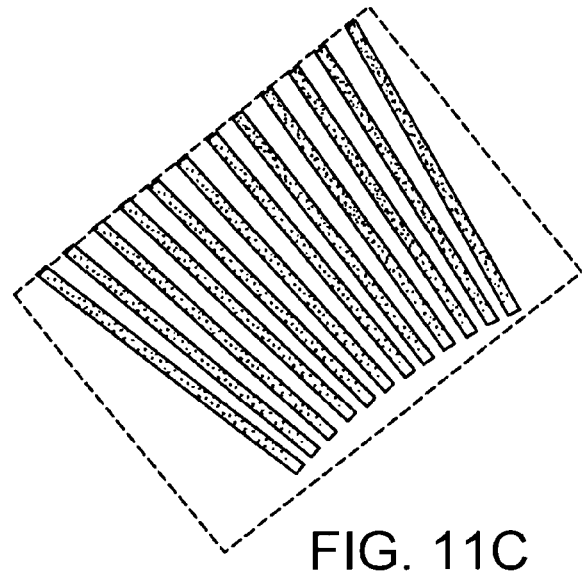

One preferred embodiment of a 2D radial spokes-wheel format for rapid solution exchange is shown in FIGS. 11A-C and FIG. 12. In this embodiment, an array of microchannels is arranged in a spokes-wheel format and converges in a circular sensor chamber at the center. The number of microchannels used will depend on the number of wells in the well plate to which the microchannels are to be interfaced. For example, a 96 sample-well plate will require at least 96 microchannels for ligand delivery and an additional 96 microchannels for waste, with each waste microchannel oriented at about 180° with respect to its corresponding sample delivery microchannel. In addition to these 192 microchannels, there is one pair of microchannels used for buffer superfusion and buffer waste, which brings the total number of channels to 194 for interfacing to 96 sample-well plates. A sensor, such as a patch-clamped cell is housed in the center chamber, which may be open volume, if interfaced with a traditional micropipette-based patch clamp system, or which may be closed volume, if interfaced with a chip-based patch clamp system. FIGS. 11A-C show the structure of this microfluidic system, which again is designed to be compatible for interfacing with a 96-well plate. Several spokes-wheel microfluidic arrangements, each having a patch-clamped detector cell, can be used on the same chip structure to obtain parallel measurements.

Figure 12:
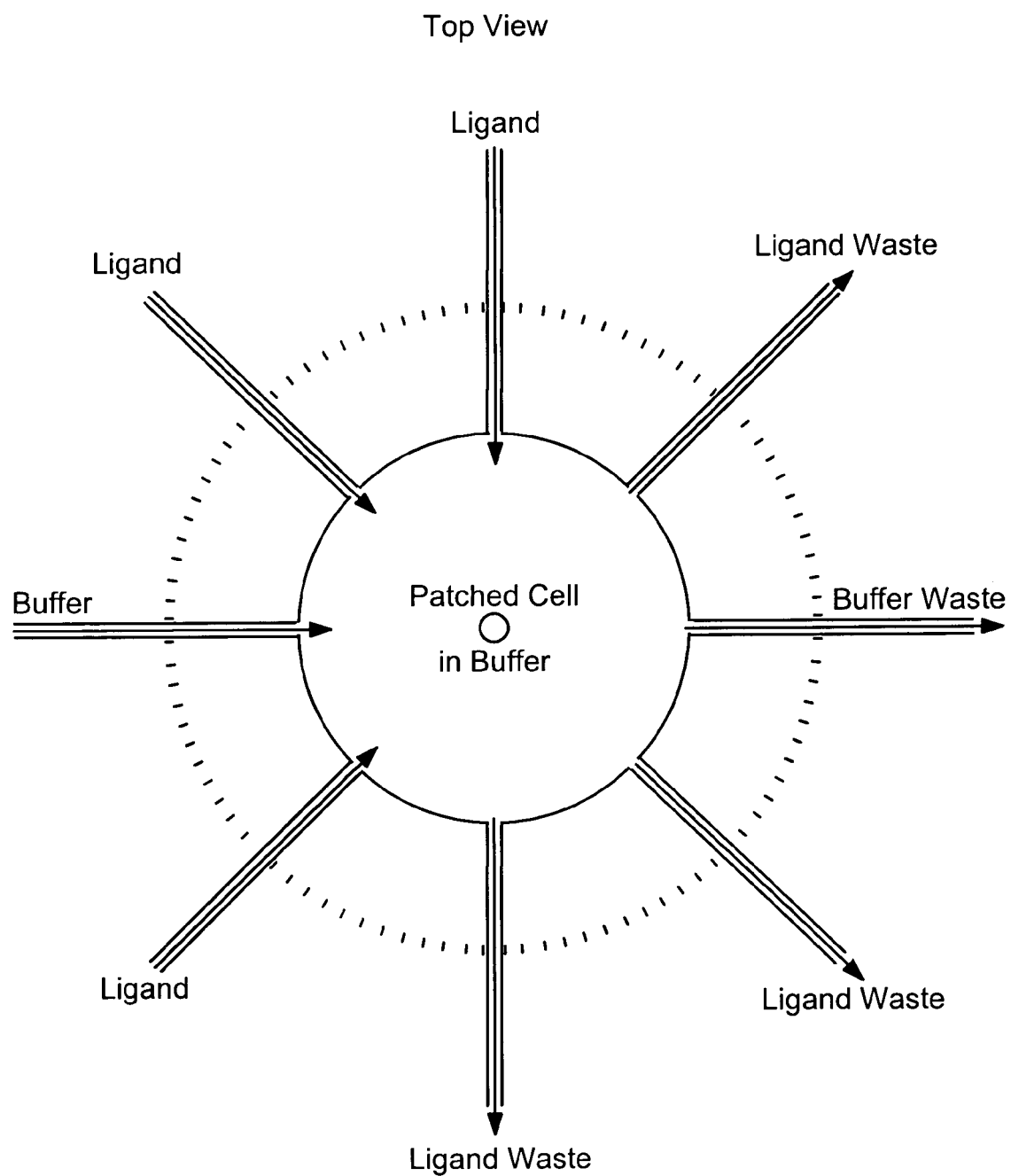
FIG. 12 is an enlarged illustration of FIG. 11A, depicting the arrangement of and flow directions of fluids in microchannels around a cell chamber with a patch-clamped cell in a planar 2D microfluidic system according to one aspect of the invention.

FIG. 12 shows an enlarged view of the sensor chamber. The dimensions of this center chamber may vary depending on the exact application, with typical diameters ranging from about 10-100 μm. The width of the microchannels will also vary, depending on the diameter of the center chamber, with typical widths ranging from about 1-10-μm. The thickness of the microchannels is less critical and will in most cases ranges from about 1-10 μm. The flow rates also can vary, with typical flow rates inside microchannels ranging from μm/s to cm/s, with corresponding flow rates in the center chamber ranging from μm/s to mm/s.

ii). Three-Dimensional Radial Spokes-Wheel Format

A three-dimensional radial spokes-wheel arrangement also can be used to efficiently replace fluids entering the sensor chamber. In this construction, one or more sensors (e.g., such as cells) are placed on a filter membrane sandwiched between a substrate comprising radial channels and a substrate comprising a waste reservoir. In this format, fluids are forced to flow down from the top layer where the radial channels reside (e.g., through input channels which feed into the radial channels), past the sensor(s), then through the filters and into the waste channel. The filter thus permits the sensor(s) to be superfused with fast fluid flow while supporting the sensors (e.g., such as cells), so they are not carried away or dislodged by the flow. In addition, the fluids are forced to flow past the sensors and to replace all the fluids that surround the sensors.

There are a number of advantages offered by this 3D design: (1) fluids around the cells are completely, efficiently, and rapidly exchanged; (2) sensors, such as cells, are firmly placed on the filter and will not be dislodged by fluid flow even at extremely high flow speed, because in the axial or z-direction, the flow pushes the cells against the filter; and (3) a minimal number of radial channels is required in comparison with the planar radial design described above. The main disadvantage of this design in comparison with other planar designs is increased complexity in the micro-fabrication.

Figure 13:
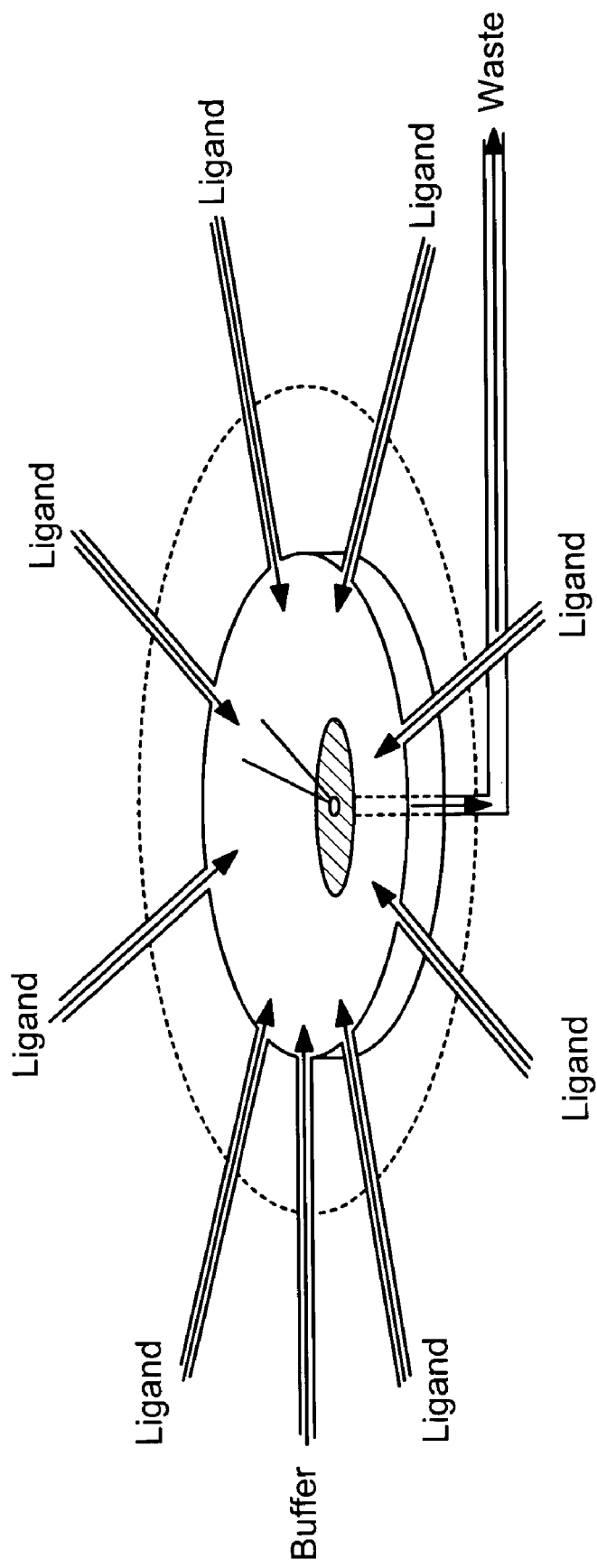
FIG. 13 is an enlarged perspective view of the system of FIG. 11A depicting the arrangement of microchannels, and flow directions in a 3D microfluidic system according to one aspect of the invention.

One preferred embodiment of the 3D radial spokes-wheel format is shown in FIG. 13. The main difference between this 3D structure and the planar structure shown in FIG. 12 is the presence of z-direction flow of fluids from the outlets of the microchannels to the inlet of the waste microchannel. Another difference is the presence of a porous membrane on which the sensor(s) (e.g., cells) are placed, which provides mechanical support for the sensors as the z-direction flow pushes the cell against the membrane. In this embodiment, the arrangements and dimensions of the microchannels are comparable to that of the 2D planar format (FIG. 12). Although the fabrication of this 3D structure is more complex than the planar structure, the presence of the z-direction flow in many cases provides better flow profiles, especially for open volume reservoirs. Because the sensors are placed immediately outside (i.e., on top) of the inlet of the waste channels, both ligand streams and superfusion streams are forced to flow past the sensor(s), which result in more efficient and complete dosing of the sensor(s) by the different fluid streams. Also, the presence of the porous membrane support permits the use of higher flow rates and thus higher throughput.

iii) Branched Channel Format

In this design, preferably only two channels are placed directly adjacent to one or more sensors (e.g., such as patch-clamped cells), one for the delivery of compounds and the other for waste. Rather than separating all the input channels and converging the outlets of each input channel so they feed into a center sensor chamber, channels are arranged in a branched geometry. To interface with 96-1024 well plates, the single delivery channel adjacent to the sensor(s) is connected to a multitude of input microchannels, each input channels receiving input from a different well of the 96-1024 well plate. This format has the advantage that the channel delivering compounds and the waste channel can be placed in very close proximity to the sensor(s), thereby ensuring a rapid response from the system. The delivery of the large number of compounds onto the sensor(s) in rapid succession is achieved by the controlled and multiplexed delivery of fluids containing compounds into the single channel feeding directly into the sensor chamber.

Figure 14A:
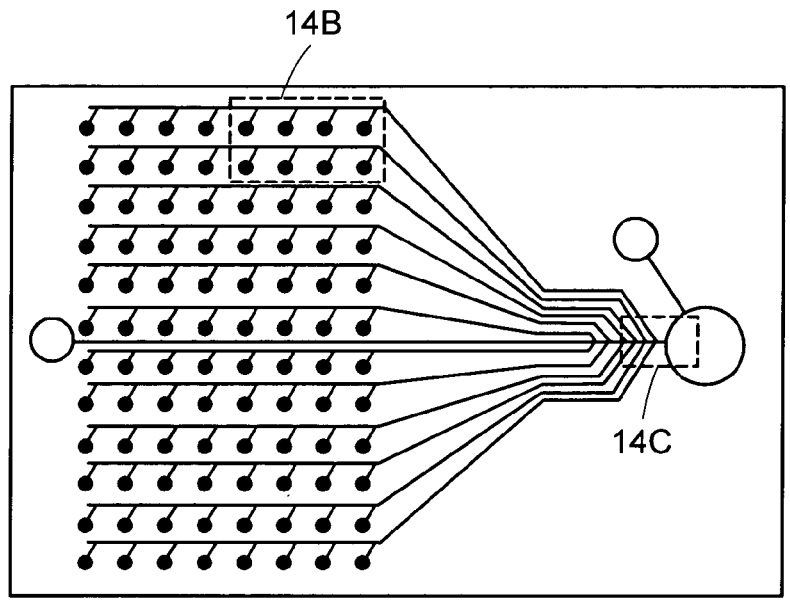
FIGS. 14A-C are top views depicting the chip structure of a fishbone design for carrying out rapid and sequential exchange of fluids around a patch-clamped cell (not shown) according to one aspect of the invention. In the example shown in FIG. 14A, a single drain channel is provided which feeds into a single waste reservoir.
Figure 14B:
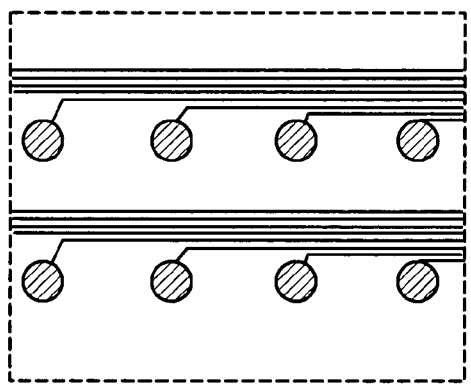
Figure 14C:
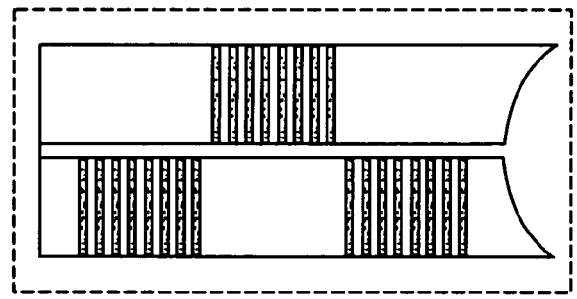

One preferred embodiment of this design is shown in FIGS. 14A-C and 15. In this embodiment, a "fish-bone" structure is fabricated with each "bone" corresponding to a sample (e.g., a ligand) delivery microchannel which intersects with a main "spine" microchannel which is connected to a buffer reservoir. The rapid and sequential delivery of sample and buffer onto one or more sensors in a sensor chamber is achieved by first applying a positive pressure to one of the sample delivery microchannels, thus introducing a plug of sample (e.g., such as a ligand) from that microchannel into the main microchannel containing the buffer. This plug is introduced onto the cell by applying positive pressure to the buffer reservoir, which carries the plug onto the sensor, and then washes the sensor (e.g., resensitizing it) with the buffer solution. This cycle of delivery of sample and buffer superfusion is repeated with different samples contained in different microchannels. The layout of this chip design is shown in FIGS. 14A-C. In the embodiment shown in the Figures, the chip can be interfaced with a 96-well plate.

Figure 15:
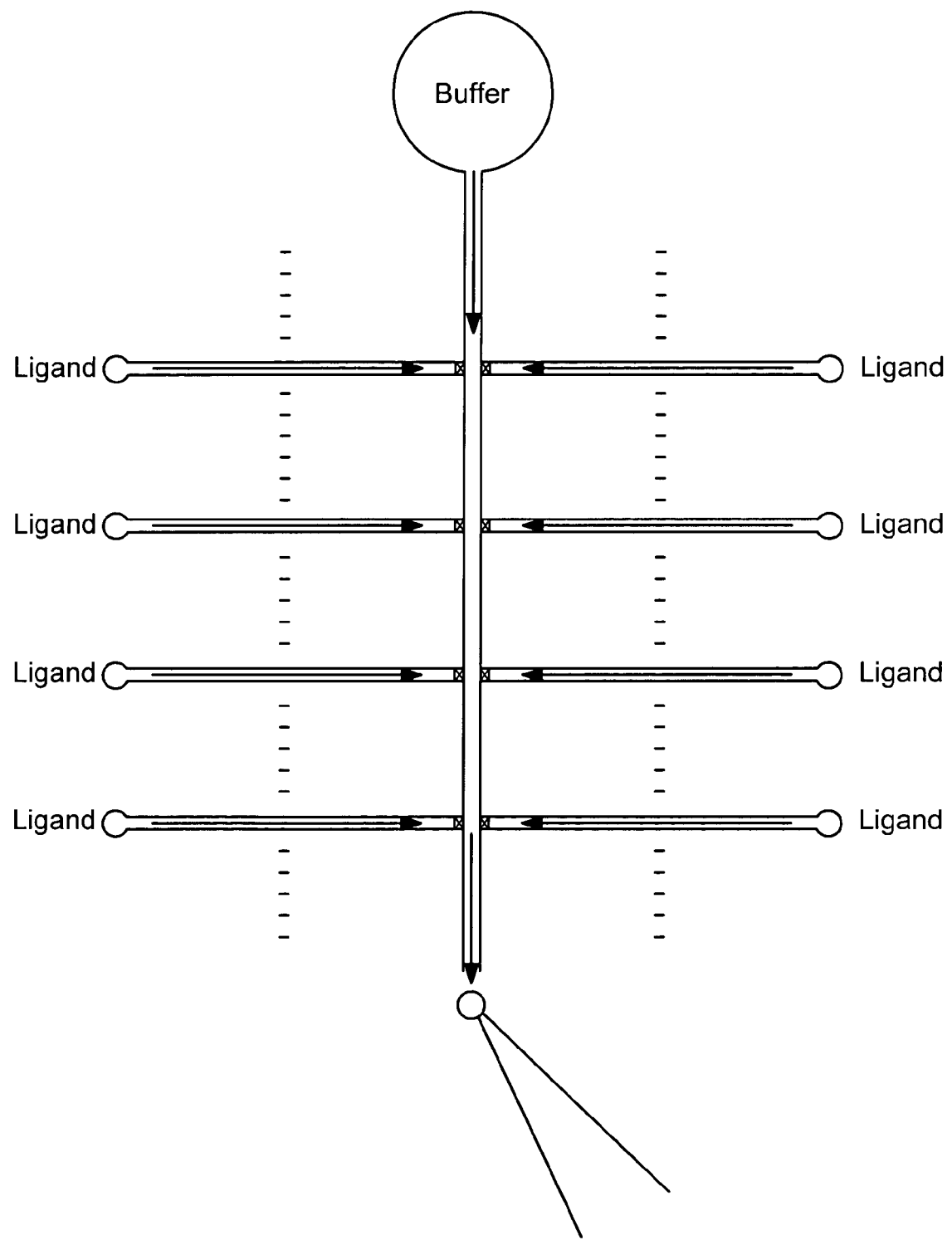
FIG. 15 is a schematic illustration of an enlarged view of FIG. 14A depicting arrangements of, and flow directions in, microchannels, and a patch-clamped cell in a chip according to one aspect of the invention, as well as the presence of passive one-way valves, which are schematically depicted as crosses.

FIG. 15 is an enlarged view of the area around the main buffer channel and the sensor chamber. The dimensions (width and thickness) of the microchannel (for both sample delivery and buffer delivery) can be highly variable, with typical dimensions ranging from about 1-100 µm, and preferably from about 10-90 µm. Flow rate also may be varied with preferred flow rates ranging from µm/s to cm/s.

Pressure is isotropic, therefore, upon application of a positive or negative pressure, fluids will flow along any pressure drop without preference to any particular direction. Therefore, preferably, passive one-way valves are integrated at the junction between sample delivery microchannels and the main buffer channel. The purpose of these integrated one-way valves is to prevent any flow from the main buffer channel into each of the sample delivery microchannels upon application of a positive pressure to the buffer reservoir, while allowing flow from each of the sample delivery microchannels into the main buffer channels when positive pressure is applied to reservoirs providing sample to these microchannels. There are numerous suitable designs for microfluidic valves as well as pumping mechanisms.

Although the discussion below emphasizes pressure driven flow owing to its simplicity of implementation, a number of appropriate means can be designed for transporting liquids in microchannels, including but not limited to, pressure-driven flow, electro-osmotic flow, surface-tension driven flow, moving-wall driven flow, thermo-gradient driven flow, ultrasound-induced flow, and shear-driven flow. These techniques are known in the art.

Valving and Pumping

Scheme 1: Using Septums to Address Individual Microchannels

In this scheme, the reservoirs that connect to each of the microchannels are sealed by a septum, for example, using polydimethyl siloxane (PDMS) for sealing or another suitable material as is known in the art. Because the septum forms an airtight seal, application of a positive pressure (e.g., with air or nitrogen) via a needle or a tube inserted through the septum will cause fluid to flow down the microchannel onto one or more sensors in a sensor chamber (e.g., to the center of a spokes-wheel where radial microchannels converge). Application of a negative pressure with a small suction through the needle or tubing inserted through the septum will cause fluid to be withdrawn in the opposite direction (e.g., from the chamber at the center of the spokes-wheel to the reservoir feeding into the microchannel).

An array of such needle-septum arrangements allows each reservoir to be individually addressed, and therefore, each microchannel. The use of this scheme permits the simultaneous and sequential pumping and valving of the fluids contained within each of the microchannels. By exercising precise control over positive and negative pressure applied to each of the microchannels, controlled fluid flow and compound delivery onto the one or more sensors can be achieved. For designs that do not require individual addressing of the microchannels (e.g., design 1—the rapid transport of patched cells across different streams of fluids), a single or a few septa with a single or a few pressure control devices will suffice.

Scheme 2: Controlling Fluidic Resistance by Varying Channel Dimensions

Although the above design using individual septa offers great flexibility and control, for certain applications in which the sequence of compound delivery and fluid flow is predetermined, a simpler design offers simplicity and ease of implementation. In this scheme, equal positive pressure is applied to all reservoirs, for example, by using pressurized air applied homogeneously to all reservoirs via a single septum, or through the use of gravity flow caused by the difference in height between inlet and outlet reservoirs. The rapid sequential delivery of compounds from each microchannel onto one or more sensors is accomplished by varying the fluidic resistance of each microchannel, which is easily achieved by varying the width and length of the each microchannel.

Fluidic resistance increases linearly with length and to the fourth power of the diameter for a circular capillary. By gradually and systematically varying the dimension of each microchannel, the time delay among the microchannels in their delivery of compounds onto one or more sensors in a sensor chamber can be controlled. This scheme is especially pertinent to high-throughput drug screening applications in which a large number of compounds are to be delivered sequentially and rapidly onto patched cell/cells with predetermined time delays.

Scheme 3: Control of Fluid Flow with External Valves

In this configuration, compounds from each of the wells of an array well plate are introduced through external tubings or capillaries which are connected to corresponding microchannels. External valves attached to these external tubings or capillaries can be used to control fluid flow. A number of suitable external valves exist, including ones actuated manually, mechanically, electronically, pneumatically, magnetically, fluidically, or by chemical means (e.g., hydrogels).

Scheme 4: Control of Fluid Flow with Internal Valves

Rather than controlling fluid flow with external valves, there are also a number of chip-based valves that can be used. These chip-based valves can be based on some of the same principles used for the external valves, or can be completely different, such as ball valves, bubble valves, electrokinetic valves, diaphragm valves, and one-shot valves. The advantage of using chip-based valves is that they are inherently suited for integration with microfluidic systems. Of particular relevance are passive one-way valves, which are preferred for implementing some of the designs mentioned in above (e.g., such as the branched channel format).

Other suitable geometries may be integrated with any of the above systems. In one aspect, at least one channel of a microfluidic system described above is a mixing channel which receives two or more separate streams of fluid from two or more other channels. The mixing channel can be used to combine the separate streams in a single channel. Such a configuration can be used to establish a concentration gradient of a substance provided in different concentrations in the two or more separate streams as is described in WO 02/22264.

Interfacing Patch Clamp Detection with Microfluidics

The system can be used to monitor cellular responses by measuring changes in electrical properties of cells. In one aspect, the sensor chamber of the chip comprises a cell-based biosensor and the system comprises a detector for monitoring the response of the biosensor to solution flow from the channels. One response which can be monitored is a change in an electrical property of the biosensor in response to gating of an ion channel. For example, a change in current flowing across the membrane of the biosensor can be measured using a voltage clamp technique. Currents can be in the range of a few picoampere (pA) (e.g., for single ion-channel openings) to several µA (for cell membranes of larger cells such as *Xenopus* oocytes).

Among voltage clamp techniques, patch clamp is most suitable for measuring currents in the pA range (see e.g. Neher and Sakmann, 1976, supra; Hamill, et al., 1981, supra; Sakmann and Neher, 1983, supra). The low noise property of patch clamp is achieved by tightly sealing a glass microelectrode or patch clamp pipette onto the plasma membrane of an intact cell thereby producing an isolated patch. The resistance between the pipette and the plasma membrane is critical to minimize background noise and should be in excess of $10^9$ ohm to form a "giga seal". The exact mechanism behind the formation of the "giga seal" is debated, but it has been suggested that various interactions such as salt-bridges, electrostatic interactions, and van der Waal forces mediate the interaction between the glass surface of the pipette and the hydrophilic heads in the lipid layer of the cell membrane (see, e.g., Corey and Stevens, 1983, In *Single-Channel Recording*, pp. 53-68, Eds. B. Sakmann and E. Neher. New York and London, Plenum Press). Variations of patch clamp techniques can be utilized such as whole-cell recording, inside-out recording, outside-out recording, and perforated patch recording as are known in the art.

In whole-cell recording, the cell membrane covering the electrode tip is ruptured by suction in order to establish an electrical connection (and a chemical pathway) between the cell interior and the electrode solution. Because electrode solution is in great excess compared to the amount of cytosol in the cell (about 10 µl vs. about 1 pl), changing ionic species in the electrode solution will create concentration gradients across the cell membrane, providing a means to control the direction and magnitude of the transmembrane ionic flow for a given receptor/ion-channel complex.

In inside-out and outside-out patch clamp configurations, the cytosolic environment is lost by excision of a membrane patch from the entire cell (see, e.g., Neher and Sakmann, 1976, supra; Sakmann and Neher, 1983, supra). To obtain an excision of a patch in both the inside-out and the outside-out configurations, the cells are preferably attached to the bottom of the sensor chamber. In the case of acutely isolated cells, for example, poly-L-lysine can be used to fix the cells to the bottom of the chamber.

The inside-out configuration allows exposure of the cytosolic side of the membrane to solution in the chamber. It is therefore a method of choice for studying gating properties of second-messenger activated ion-channels at the single-channel level. Thus, the effects of cytosolic signaling molecules or enzymatic activity on ion-channel function can be studied by means of this configuration. The outside out configuration, on the other hand, allows exposure of the extracellular side of the patch. It can therefore be used to monitor the activity of ligand-gated or receptor-operated ion-channels.

Low noise levels provide better signal-to-noise ratios where modulators (e.g., such as agonists or antagonists). Under optimal conditions, single-channel currents in the higher femto-ampere ($10^{-15}$ A) range can be resolved. Strategies to decrease noise (e.g., such as caused by a bad seal between the electrode and the cell) to facilitate formation of GΩ-seals include, but are not limited to, fire polishing of the glass electrode or treating the surface the glass electrode using agents such as sigmacote. Dielectric noise and capacitive-resistive charging noise also can be decreased by selecting an expedient electrode/pipette geometry, using quartz glass, and by coating of the glass surface of the pipette with Sylgard® (silicone, PDMS) in order to insulate the pipette tip as much as possible.

One frequently used modification of the whole-cell configuration, the perforated patch mode, also can be used (see, e.g., as described in Pusch and Neher, 1988, supra). In this technique, holes are selectively made in the cell membrane using a pore-building protein, such as amphotericin or nystatin (see, e.g., Akaike et al., 1994, *Jpn. J. Physiol.* 44: 433-473; Falke, et al., 1989, *FEBS Lett.* 251: 167; Bolard, et al., 1991, *Biochemistry* 30: 5707-5715) to create increased conductivity across the patched cell membrane without the loss of intracellular signalling molecules.

In addition to measuring ion currents across ion channels at constant membrane potential, the patch clamp technique can be used to measure membrane voltage at a known constant or time-varying current. This patch clamp configuration, referred to as "current clamp", measures the change in membrane potential caused by activation of ligand-gated ion-channels or by voltage-gated ion channels and is particularly suited for creating a biosensor which can be used to monitor the effects of agents (e.g., drugs) on action potentials (i.e., frequency, duration, and amplitude). This technique also can be used to study the effect of an agent to study an agent's impact on the excitability of a nerve cell. Therefore, in one aspect, the system is used to monitor the modulation of the voltage threshold (e.g., hyperpolarizing or depolarizing) of a cell-based biosensor in a current clamp mode when an action potential is triggered.

In another aspect, the system is used to monitor capacitance changes in cell membranes by providing a cell-based biosensor in the open volume reservoir and measuring impedance of the membrane across the membrane of the biosensor in an AC mode. For example, the system can be used to monitor the effect of agents on the release of vesicles from a cell (i.e., exocytosis) and/or on the uptake of vesicles by a cell (i.e., endocytosis).

One preferred embodiment for interfacing microfluidic systems with electrophysiological patch clamp recordings is shown in FIG. 1A. In FIG. 1A, a single patch-clamped cell is shown; however, several patch-clamped cells can be used simultaneously. External pumps and fluid control equipments are placed adjacent to a standard microscope. The entire integrated system preferably is computer-controlled and automated. The different components of the system (i.e. microfluidics, scanning mechanism, patch clamp, and the like) may be controlled separately using separate controllers and separate software, but most preferably these components are all controlled by a single system processor as described above.

The system can be readily adapted for use with a conventional patch clamp pipette or micropipette. In one aspect, a cell or a fraction of a cell (e.g., a cell membrane) is positioned at the opening of a patch clamp micropipette. Patch clamp micropipettes are known in the art and are available, for example, from World Precision Instruments, Inc. (Sarasota, Fla. 34240 USA; at http://www.wpiinc.com/WPI_Web/Glass-Holders/Patch_Clamp_Glas.html). Suction is applied to the patch clamp micropipette until a giga-seal (giga-ohms) is created between the end of the micropipette and the membranes of the cell. Preferably, a change in one or more electrical properties of the cell is monitored as a means of determining the presence of a ligand or other compound in a fluid stream coming into contact with the cell. For example, an electrical signal can be detected by an electrode in the micropipette and transmitted, preferably with amplification, to the system processor. A reference electrode, which contacts solution in the sensor chamber, also is required.

Various supporting solutions can be adapted for use in sensor chamber. The type of solution will depend on the sensor and compounds being evaluated. For example, a sensor solution can be a recording solution used for traditional patch clamp analysis of an ion channel. In general, the exact composition of a solution for patch clamp recording will vary depending on the type of channel being evaluated (see, e.g., U.S. Pat. No. 6,333,337, for potassium channels; U.S. Pat. No. 6,323,191, for Cl channels, and PCT/US99/02008, for sodium channels); such solutions are well known in the art.

In one aspect of the invention, patch clamp recording is automated and controlled by the system processor. For example, the system processor may direct the movement of one or more micropipettes to pre-programmed locations. In another aspect, the system processor directs the movement of the one or more micropipettes in response to image analyses of cells in the sensor chamber (e.g., the system monitors the delivery of cells to the micropipette(s) from one or more treatment chambers). In a preferred aspect, acquisition and analysis of patch clamp data, followed by a feedback control to vary microfluidic settings (e.g., pressure, valves and switches) and to control scanning parameters (e.g., speed and trajectory of scanning, pressure drops across channels), is implemented by the system processor.

Figure 1C:
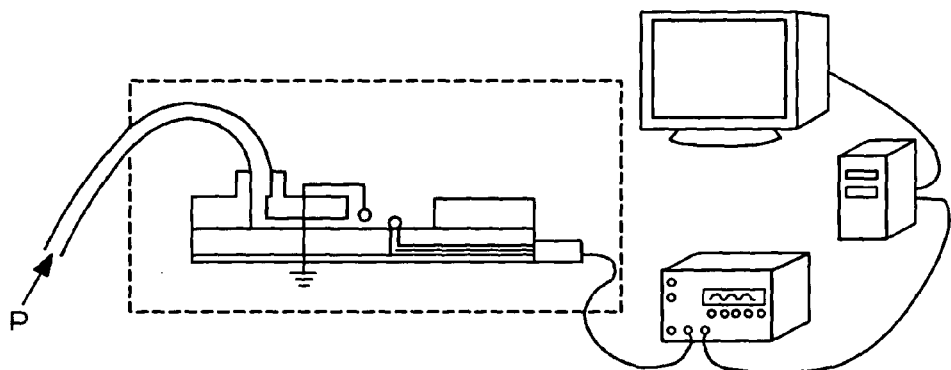
FIG. 1C is a side view, partially in section, of a chip-based patch clamp system. In operation, the chip is preferably covered.

In addition to integrating with traditional patch clamp systems, the microfluidics platform according to the invention also is ideally suited for interfacing with chip-based patch clamp, as described, for example, in WO 99/31503; WO 01/25769; WO 01/59447; and WO 99/66329. This embodiment is shown in FIG. 1C and can eliminate such system components as a microscope, micropipette, micromanipulators, and the like. Chip-based patch clamp integrate readily with the substrates of the invention. Chip-based patch clamp systems also provide the ability to patch clamp several cells together on a single substrate.

Methods of Using the System

The invention exploits the potential for using microfluidic systems to control the delivery of a large number of different biologically active molecules and compounds (e.g., candidate drugs) to a sensor comprising a target molecule. Suitable molecules/compounds which can be evaluated include, but are not limited to, drugs; irritants; toxins; proteins; polypeptides; peptides; amino acids; analogs and modified forms of proteins; polypeptides, peptides, and amino acids; antibodies and analogs thereof; immunological agents (e.g., such as antigens and analogs thereof, haptens, pyrogens, and the like); cells (e.g., such as eukaryotic cells, prokaryotic cells, infected cells, transfected cells, recombinant cells, bacteria, yeast, gametes) and portions thereof (e.g., cell nuclei, organelles, secretogogues; portions of cell membranes); viruses; receptors; modulators of receptors (e.g., agonists, antagonists, and the like); enzymes; enzyme modulators (e.g., such as inhibitors, cofactors, and the like); enzyme substrates; hormones; metabolites and analogs thereof; nucleic acids (e.g., such as oligonucleotides; polynucleotides; fibrinotides; genes or fragments, including regulatory sequences, and/or introns, and/or coding regions; allelic variants; RNA; antisense molecules, ribozymes, nucleotides, aptamers), including analogs and modified forms thereof; chemical and biological warfare agents; metal clusters; and inorganic ions.

Combinations of two or more of any of these molecules also can be delivered, sequentially or simultaneously, to one or more sensors in the sensor chamber. Compounds also can be obtained from synthetic libraries from drug companies and other commercially available sources known in the art (e.g., including, but not limited, to the LeadQuest® library comprising greater than 80,000 compounds, available through http://www.tripos.com/compounds/; ChemRx Diversity Library, comprising 1000 to 5000 compounds per scaffold, available through http://www.chemrx.com; the Nanosyn Pharma library, available through Nanoscale Combinatorial Synthesis Inc., Menlo Park, Calif., and the like) or can be generated through combinatorial synthesis using methods well known in the art. In aspects in which molecules are delivered to cells, any of the molecules described above may be taken up by cells by transiently exposing the cells to an electric field (e.g., in a cell treatment chamber or in a sensor chamber which is adapted for electroporation) as described above.

Providing Periodically Resensitized Ion Channel Sensors

Binding a compound (such as an agonist or modulator or drug) to a broad range of ion channels not only evokes conformational changes in these channels, allowing a flux of ions across a cell membrane, but also causes the ion channel to desensitize, i.e., to reside in a long-lasting, ligand-bound, yet shut-off and non-conducting state (see, e.g., Jones and Westbrook, 1996, *GL Trends Neurosci.* 19: 96-101). Desensitization of many types of ion-channels usually occurs within a few milliseconds and is thought to be one of the mechanisms by which synaptic information in the central nervous system is processed and modified. Densitization also may serve as a negative feedback mechanism that prevents excitotoxic processes caused by excessive activation of ion channels by neurotransmitters or other neuromodulators (see, e.g., Nahum-Levy, et al., 2000, *Biophys J.* 80: 2152-2166; Swope, et al., 1999, *Adv. Second Messenger Phosphoprotein. Res.* 33: 49-78).

Figures 24A, 24B:
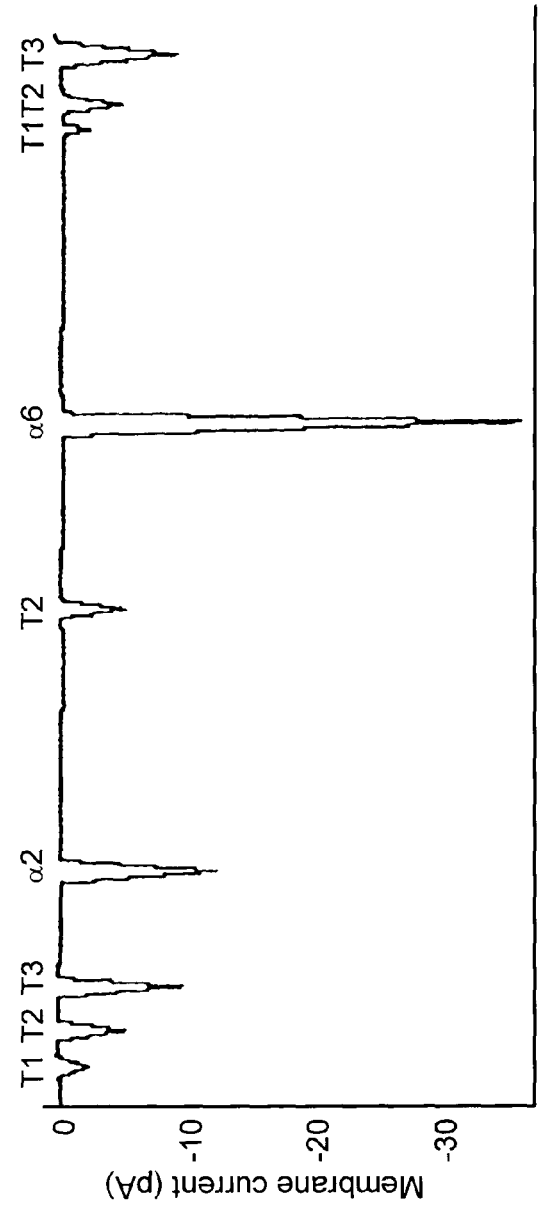

In one aspect, to achieve high screening rates in, for example, HTS applications, patch-clamped cell(s) in the sensor chamber are moved from the outlet of one microchannel to the next in rapid succession. To achieve rapid resensitizaton of ion channels and receptors, microchannels delivering samples comprising suspected modulators, agonists, or drugs of receptor/ion channels are interdigitated with microchannels delivering buffer for resensitization of the receptor/ion channels (e.g., buffer free of any agonist). In addition to resensitizing ion channels and receptors, this delivery of buffer onto cells between ligand and drug exposure serves to wash out ligands and drugs previously administered to the cell. Thus, in this aspect, the system is used to screen for an agonist or modulator or drug of a specific ion-channel by providing a periodically responsive ion channel sensor. For example, by providing pulsed or steady-state flow delivery of buffer to the sensor, the system provides a cell that is resensitized when exposed to a channel outlet delivering a candidate agonist or modulator or drug. FIGS. 24A-C show simulated screenings of unknown agonists according to one method using a microfluidic chip comprising 26 outlets feeding into a sensor chamber. The contents of each channel are shown in FIG. 24A. Agonists with known pharmacological action (e.g., known efficacy, or potency) have been included in certain channels to serving as internal controls or standards. The score sheet for this experiment, i.e., the patch clamp response obtained for each microchannel is shown in FIG. 24C.

Figures 27A, 27B:
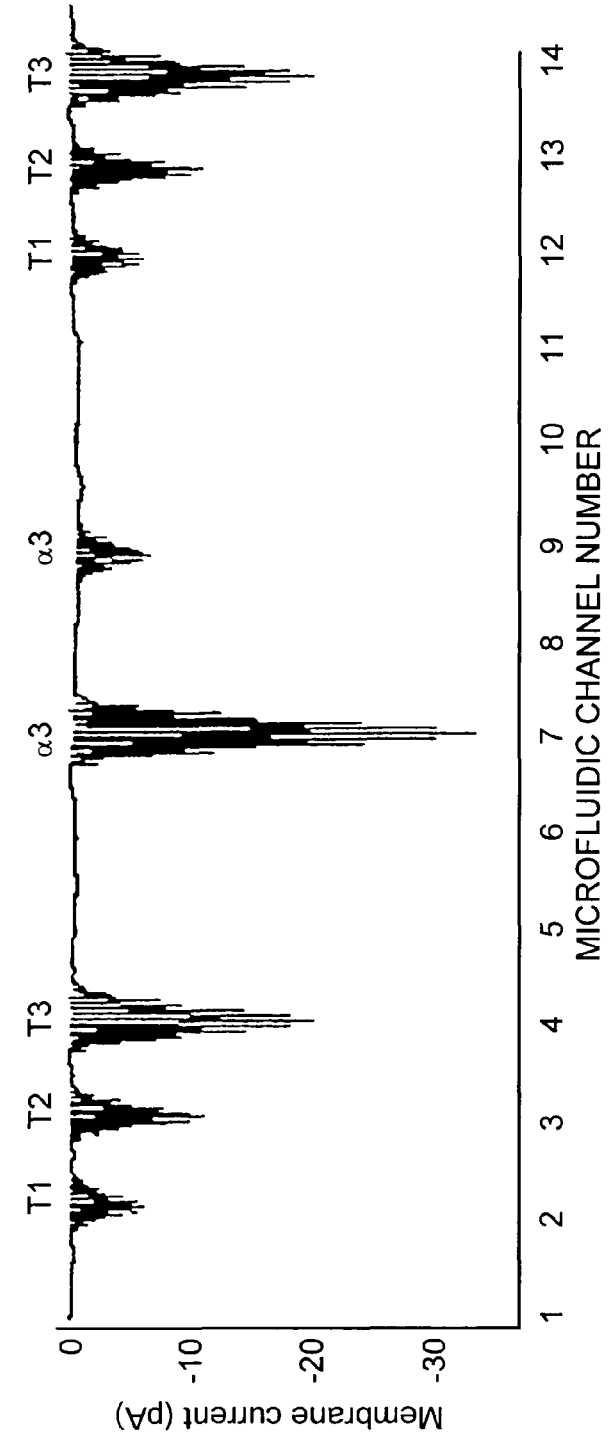

In another embodiment, an additional superfusion pipette proximal to the patch-clamped cell, e.g., in an arrangement that is adjacent to or coaxial with respect to the patch pipette (as detailed below), is used to continuously resensitize/wash receptors/ion channels on the cell surface. This enables cells to be extremely rapidly resensitized and washed (e.g., within ms) and enables several different readings/registrations of ion channel activation to be made as a cell moves across a channel outlet. FIGS. 27A-C show a simulated method of rapid resensitization used for screening of agonists which combines the use of a microfluidic chip comprising 14 outlets feeding into a sensor chamber with pulsed superfusion of agonist-free buffer solution using a fluidic channel (or micropipet) placed coaxial or orthogonal or otherwise in close proximity to a patched-clamped cell. The contents of each microfluidic channel are shown in FIG. 27A. Agonists with known pharmacological action (e.g., known efficacy, or potency) have been included in certain channels to serve as internal standards or test compounds.

The simulated trace, shown in FIG. 27B, for a linear, single, forward scan of a cell-based biosensor across microfluidic channel outlets, show a plurality of peak responses obtained per single microchannel outlet. The score sheet for this experiment, i.e., the patch clamp response obtained for each microchannel is shown in FIG. 27C. In this case, a Gaussian-distributed response is obtained because it was modeled that the ligands exiting microchannels into the open volume had a gaussian distribution. Many other types of distributions can be obtained depending on substrate geometry and experimental parameters, such as level of collimation of flows. However, this type of repeated superfusion of cells during their passage across a single microchannel outlet allows dose-response information and high signal-to-noise ratios to be obtained for receptors/channels that rapidly desensitize.

To obtain desired data, variable scan rates of cell(s) across individual streams of sample and buffer and variable pressure drops across each microchannel can be implemented by the system, either from pre-programmed instructions or in response to feed-back signals from a detector in electrical communication with the patch clamp electrode (e.g., based on a detected signal or in real-time).

The system thus can be used to change microenvironments rapidly around a cell comprising a receptor/ion-channel. For example, the system can provide a periodically responsive ion channel. Because of the small dimensions of the substrates and microchannels used herein, which allows for rapid mass transport, the system enables a user to screen for drugs, in some instances, at the rate of hundreds per second (i.e., millions per hour) using one patch clamp sensor, provided drugs and resensitization solutions are delivered sequentially at a comparable rate to the sensor. As discussed above, scanning rates can be modified to account for the physiological responses of a cell-based sensor, e.g., providing slower scanning rates for receptors that equilibrate slowly.

Generating Dose-Response Curves and Analyzing Ion-Channel Pharmacology

Dose-response curves provide valuable information regarding the actions and potencies of drugs. Obtaining dose-response curves using traditional methods involving micropipettes often can be time consuming and tedious. The present invention, which uses microfluidics for the rapid and controlled manipulation of the microenvironemnt around cell(s), is uniquely suited for dose-response measurements. Dose-response relationships most often follow a sigmoidal curve in a lin-log plot, and can be described by the Hill logistic functions:

$$I=I_{max}/[1+(EC_{50}/C)^n]$$

Where I is the whole-cell current, C is the concentration of ligands, $I_{max}$ is the maximal current (i.e., when all channels are in the open state), $EC_{50}$ is the half-maximal value (i.e., when half of the receptor population is activated, and often equals $K_D$, the dissociation constant of the ligand), and n is the Hill coefficient that reflects the stoichiometry of ligand binding to the receptor.

Figures 26A, 26B:
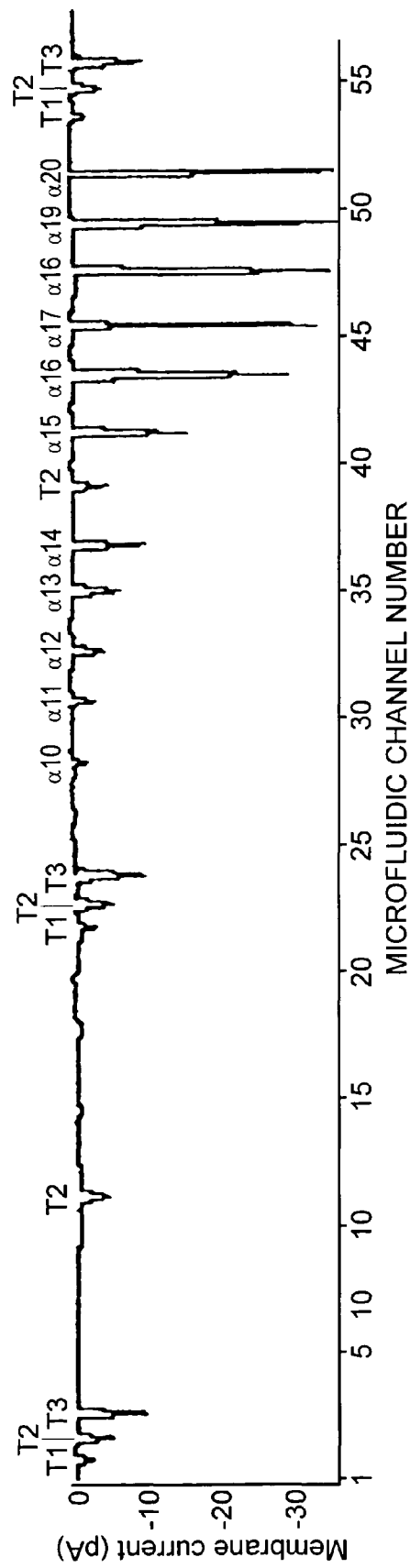

In one aspect, to achieve dose-response information for agonists, patch-clamped cell(s) in the sensor chamber are moved from the outlet of one microchannel to the next in rapid succession. Microchannels delivering agonists at different concentration are interdigitated with microchannels delivering buffer free of agonist (e.g., to resensitize receptors/ion channels and/or to wash out compounds previously administered to the cell, as described above). Preferably, the serially or sequentially diluted agonists are loaded into different channels. FIG. 26A is an example of such a loading scheme in a 56-channel substrate. Agonist is present at highest concentration in channel 52 and then is serially diluted at each subsequent channel until channel 6. Agonists with known pharmacological action (e.g., known efficacy, or potency) have been included in certain channels to serve as internal standards. Preferably, the agonist concentration from the channel with the highest concentration to the channel with the lowest concentration covers many orders of magnitude. FIG. 26B show simulated patch clamp recordings of agonists at different concentration as described above. From the score sheet for this simulated experiment, i.e., the patch clamp response obtained for each microchannel as shown in FIG. 26 C, a dose-response curve can be constructed.

Similarly, with some modifications, dose-response curves can be obtained for antagonists as well using the system which is described in more detail below. Furthermore, as described above, the combination of microfluidics with patch clamp can provide a wide range of information about the actions of modulators on ion-channels, e.g., such as the association and dissociation constants of a ligand for its receptor, and whether a modulator is an agonist or an antagonist of a receptor. It is also possible, however, to obtain dose-response information from accumulated responses of ligands without washing or resensitizing the receptors with interdigitated flows of buffer. In this aspect, the microchannels need only contain ligand solutions at different concentrations.

(i) Detection and Characterization of Agonists

Partial Agonists

The ability of a drug molecule to activate a receptor-mediated response is a graded property, rather than an all-or-nothing property. If a series of chemically related agonists acting on the same receptor are tested on a cell, the maximal response (i.e., the largest response that can be produced by an agonist in high concentration) generally differs from one agonist to another. Some compounds (known as "full agonists") can produce a maximal response whereas others, referred to "partial agonists", can only produce a submaximal response. An "partial agonist" can therefore act as a "weak antagonist" by hampering a full agonist from binding a receptor. Thus, by using a defined ion-channel together with a known agonist that produces a maximal response, the grade of an agonist's activity can be monitored (see, e.g., FIG. 24).

(ii) Detection and Characterization of Antagonists

In one aspect, the system is used to screen for antagonists of ion-channel activity. Suitable ion-channels which can be evaluated include: (i) ion channels that do not de-sensitize; (ii) ion-channels that desensitize (iii) ion-channels that desensitize but which mediate large current fluctuations when activated; and (iv) ion-channels whose desensitizing property is blocked by irreversible binding of an allosteric modulator (e.g., such as a lectin). To detect antagonists, the ion-channels or receptors expressed by a biosensor need to be activated or "tested" by an agonist during, before, or after, application of the antagonist. For example, different antagonists can be applied together with a well-defined agonist with known pharmacological properties. Antagonists at different concentrations also can be loaded into microchannels together with agonists at a constant concentration.

To achieve rapid resensitizaton of ion channels and receptors, microchannels containing agonist and antagonist (e.g., such as ligands and drugs) can be interdigitated with microchannels delivering buffer free of any agonist or antagonist (e.g., buffer for resensitization of the receptor/ion channels). In addition to resensitizing ion channels and receptors, exposure of cells to buffer between periods of exposure to ligands and drugs serves to wash out ligands and drugs previously administered to the cell. Thus, in this aspect, the system is used to provide a periodically responsive ion channel sensor. Antagonists are detected in this system by their inhibition of the agonist-induced response.

In another aspect, the system is used to screen for antagonists which can be detected through attenuation in the signal mediated by constantly pre-activated receptors/ion-channels. In this particular setup, different channels are loaded with different antagonists, or with the same antagonist at different concentrations, or a combination of both, while each channel comprising antagonist comprises agonist at a constant concentration. To achieve continuous activation of receptors and ion channels, microchannels containing agonist and antagonist are interdigitated with microchannels delivering buffer and agonist at the same concentration as in the channels supplemented with antagonist. This delivery of buffer supplemented with agonist onto cells between ligand and drug exposure serves to wash out ligands and drugs previously administered to the cell and also can serve to resensitise a receptor/ion channel.

Figures 25A, 25B:
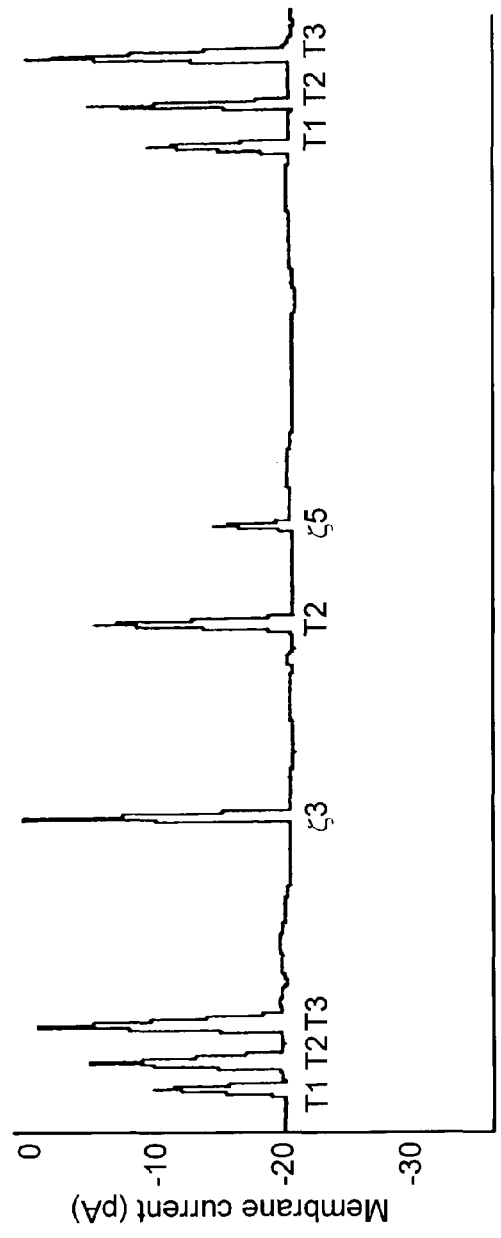

A simulation of such an experiment is shown in FIGS. 25A-C. The contents of each channel is shown in FIG. 25A. Antagonists with known pharmacological action (blocking potency) have been included in certain channels to serve as internal standards. The simulated trace shown in FIG. 25 B represents a linear single forward scan of a cell-based biosensor across microfluidic channel outlets. As shown in the Figure, a plurality of peak responses are obtained per single microchannel outlet. The score sheet for this experiment, i.e., the patch clamp response obtained for each microchannel, is shown in FIG. 25C, from which the antagonist with the highest blocking potency can be identified.

Competitive Antagonism

This type of antagonism refers to competition between agonists and antagonists at the same binding site on the receptor. Reversible competitive antagonism is characterized by a shift in the slope of a dose response curve to higher concentrations while maintaining the same maximum response and the slope of the curve. In irreversible competitive antagonism, no change in antagonist occupancy is observed when the cell is exposed to agonist.

Non-Competitive Antagonism

Non-competitive antagonism describes the situation where the antagonist blocks, at some point, the chain of events that leads to the production of a response by the agonist. In this type of antagonism, the agonist and antagonist either bind to different sites on the receptor/ion channel or the antagonists simply block the ion channel pore. The net effect is to reduce the slope and maximum of the agonist's dose-response curve.

Isosteric Inhibition

This type of antagonism refers to the self-inhibition of agonists above a certain concentrations; that is, an agonist will start to antagonize its own action at a sufficiently high concentration. A bell-shaped dose-response curve often signals the presence of this kind of antagonism.

Detection of Modulators of Presynaptically Expressed Ion-Channels

In another aspect, the system is used to detect a modulator of a presynaptically expressed ion-channel. Strategies for studying presynaptically localized ion-channels often include patch clamp recordings of synaptosomes (i.e., pinched-off nerve terminals produced by homogenizing brain tissue) inserted in proteoliposomes or planar phospholipid bilayers (see, as described in Farley and Rudy, 1988, *Biophys. J.* 53: 919-934; Hirashima and Kirino, 1988, *Biochim Biophys Acta* 946: 209-214, for example). The method of Hirashima and Kirino, 1988, supra, is particularly preferred, as it is a simple and rapid technique for generating giant proteoliposomes comprising presynaptically expressed ion-channels which can be used as biosensors for patch clamp analysis in the system according to the invention.

Detection of Ligands Acting on Orphan Receptors/Ion-Channels

Conventional drug discovery approaches often are initiated by the discovery of ligand's biological activity which is subsequently used to characterize its tissue pharmacology and physiological role. Typically, after the ligand is characterized, the corresponding receptor is identified as target for drug screening in HTS applications. A relatively novel strategy for characterizing orphan receptors (i.e., receptors with an undefined biological activity) is often referred to as a "reverse pharmacology" approach.

The reverse approach starts with an orphan receptor of unknown function that is used as target for detection of its ligand. The ligand is then used to explore the biological and pathophysiological role of the receptor. High-throughput screening is initiated on the receptor at the same time that the ligand is being biologically characterized in order to develop antagonists that will help determine the therapeutic value of the receptor.

The present invention is particularly useful for a reverse pharmacological approach. In one aspect, the system comprises a cell-based biosensor which is a non-native cell line which expresses an exogenous orphan receptor (e.g., such as an ion channel). Suitable native cell lines, include, but are not limited to, HEK-293, CHO-KI, and COS-7.

There are several benefits coupled to screening ion channels in a non-native cell background. First, a transfected cell line containing a null background (e.g., which does not ordinarily express the orphan receptor) allows one to be certain of the molecular identity of the gene responsible for the observed signal. Second, the orphan receptor can be overexpressed, thus improving the signal-to-noise of the screening read-out. Third, host cells with low background conductances can be chosen to allow very sensitive assays of certain types of ion channels. Finally, these cell lines are relatively easy to culture and are robust enough to be handled by automated screening systems.

Detection of Modulators of Neurotransmitter Vesicular Release

Patch-clamp techniques to measure membrane capacitance, developed over ten years ago (see, e.g., Neher and Marty, 1982, *Proc. Natl. Acad. Sci. USA* 79: 6712-6716), provide a powerful tool to study the underlying mechanism and control of exocytosis.

The surface area of a cell depends on the balance between exocytosis and endocytosis. Exocytosis results in the discharge of vesicle contents (i.e., such as neurotransmitters) into the extracellular space and the incorporation of vesicle membrane into the plasma membrane, leading to an increase in cell surface area. During endocytosis, parts of the plasma membrane are retrieved, resulting in a decrease in the surface area. Changes in net exocytotic and endocytotic activity thus can be monitored by measuring changes in cell surface area.

Membrane capacitance is an electrical parameter of the cell that is proportional to the plasma membrane area. Thus, providing the specific capacitance remains constant, changes in plasma membrane area resulting from drug-induced modulation of exocytotic and endocytotic activity through presynaptically located ion-channels, can be monitored by measuring membrane capacitance by means of patch clamp in the open sensor chamber of the system.

Determining Permeability Properties of a Cell

When a cell used in a screening procedure expresses a broad range of ion-channel types, characterizing the ion permeability properties of the cell's activated ion-channels can be used to characterize a drug's interaction with the cell. Information about permeability properties of an ion-channel can be determined by monitoring reversal potential which can be determined by evaluating current-to-voltage relationships, created from measurements of agonist-evoked currents at different holding potentials. By employing the reversal potential and knowledge about intra- and extra-cellular ion concentrations, the relative ion-channel permeability properties are determined from different models.

Noise Analysis of Current Traces

Analysis of current-traces from ion-channels activated by agonists can be performed on both an ensemble- and single-channel level for further characterization of an agonist-ion-channel interaction. The Fourier transformation of the autocorrelation function obtained for the total current recorded with whole-cell patch clamp yields power spectra that can be fitted by single or double Lorentzian functions. These fits provide information about mean single-channel conductances and ion-channel kinetics (e.g., mean single channel open time) through analysis of the frequency dependence of the current response (i.e., corner frequency). In principle, although a more difficult and tedious technique, recordings obtained from outside-out patch-clamp configurations also can be analysed to measure single-channel opening intervals and different conductance levels mediated by the same receptor-ion channel complex.

EXAMPLES

The invention will now be further illustrated with reference to the following examples. It will be appreciated that what follows is by way of example only and that modifications to detail may be made while still falling within the scope of the invention.

Example 1

Microfabrication of a Substrate

Figure 19A:
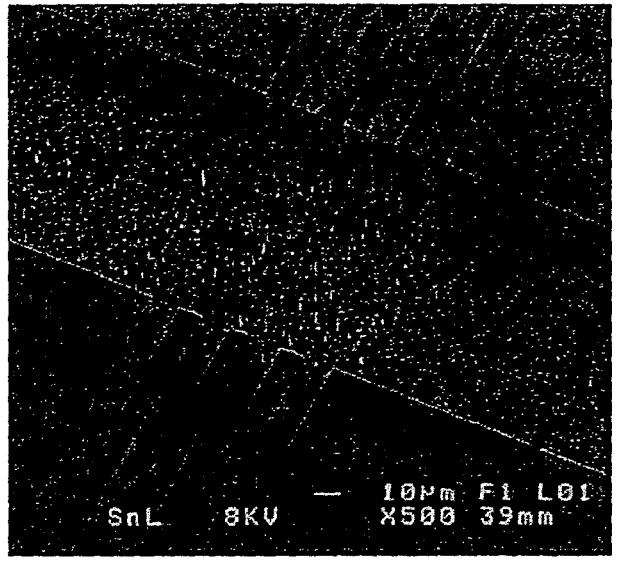
FIGS. 19A-C show scanning electron micrographs of microchannels fabricated in silicon.
Figure 19B:
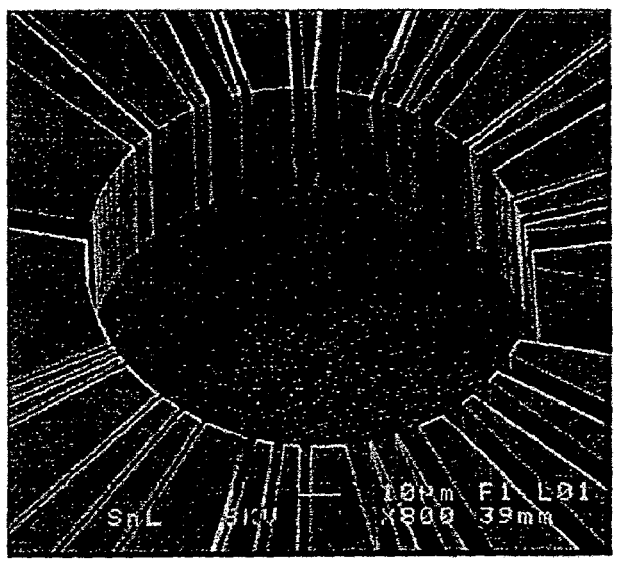
Figure 19C:
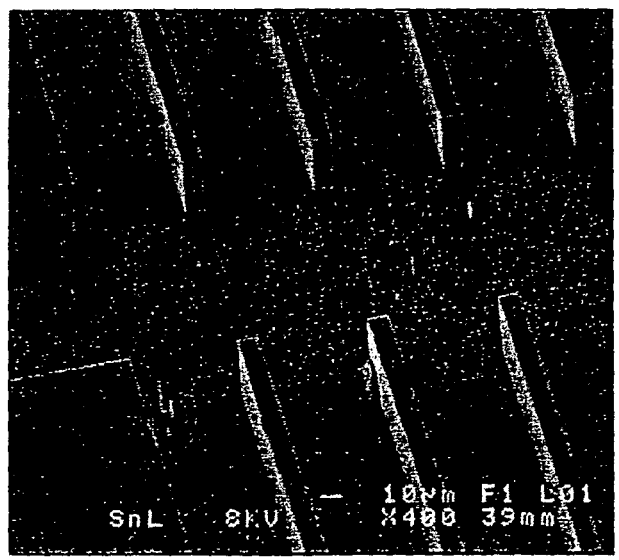

FIG. 19 shows examples of microchannels fabricated in silicon by deep reactive ion etching in $SF_6$. Masks for photolithography were produced using standard e-beam writing on a JEOL JBX-5DII electron beam lithography system (medium reflective 4" chrome masks and Shipley UV5 resists, 50 keV acc. voltage, dose 15 µC/cm$^{-2}$, exposure current 5 nA). The resist was spin coated at 2000 rpm for 60 s giving 250 nm of resist and soft baked for 10 minutes at 130° C. on a hotplate before exposure. The pattern was post exposure baked for 20 minutes in an oven at 130° C. and developed for 60 s in Shipley MF24-A, rinsed in DI water and etched in a reactive ion etcher (Plasmatherm RIE m-95, 30 s, 50 W, 250 mTorr, 10 ccm $O_2$). The chrome was etched for 1-2 minutes in Balzers chrome etch #4, the mask was stripped of the remaining resist using Shipley 1165 remover and rinsed in acetone, isopropanol and DI water. A 3", [100], two sides polished, low N-doped Silicon wafers with 700 nm of thermally grown silicon dioxide and a total thickness of 380 µm was cleaned in a reactive ion etcher Plasmatherm RIE m-95 (30 s, 50 W, 250 mTorr, 10 ccm $O_2$), spin coated with Shipley S-1813 photoresist at 4000 rpm, giving 1.3 µm of resist, and exposed for a dose of 110 mJ/cm$^{-2}$ at 400 nm wavelength on a Carl Süss MA6 mask aligner. The wafer was developed for 45 s in Shipley MF319 rinsed in DI water and ashed in a reactive ion etcher (Plasmatherm RIE m-95, 30 s, 50 W, 250 mTorr, 10 ccm $O_2$). The wafer was hard baked for 10 minutes at 130° C., the silicon dioxide was etched with SioTech buffered oxide etch and rinsed in DI water. The wafer was stripped of the remaining resist with acetone, rinsed in isopropanol and DI water. The other side of the wafer was spin coated with Shipley AZ4562 photoresist at 3000 rpm for 30 seconds giving approximately 8 µm of resist, soft baked for 3 minutes at 100° C. on a hotplate and exposed for a dose of 480 mJ/cm$^{-2}$ at 400 nm wavelength on a Carl Süss MA6 mask aligner. The pattern was developed for 200 seconds in Shipley MF312 and DI water in 50:50 mix, rinsed in DI water, and ashed in a reactive ion etcher (Plasmatherm RIE m-95, 30 seconds, 50 W, 250 mTorr, 10 ccm $O_2$).

The pattern defined in the photoresist AZ4562, the recording chamber and the combined access holes and sample wells was etched in a STS Multiplex deep reactive ion etcher using $SF_6$ as etching gas and $C_4F_8$ as passivation gas at 600 W of RF power and 30 W of platen power. The system was operating at a constant APC angle of 74% and the etching time was 12 seconds with an overrun time of 1 second, and the passivation time 8 seconds with an overrun time of 1 second. The etching rate was approximately 4.9 µm/minute and the etching time 60 minutes resulting in a depth of approximately 300 µm. The wafer was stripped of the remaining resist in acetone, rinsed in isopropanol and DI water.

The pattern in silicon dioxide defining the microchannels was etched with the same system as before but with 800 W of RF power, at a constant APC angle of 68% and the etching time was 7 s with an overrun time of 0.5 s, and the passivation time 4 second with an overrun time of 1 second. The etching rate was approximately 3.3 µm/min and the etching time 30 minutes resulting in a depth of 100 µm. The wells and the recording chamber were completely etched through resulting in holes in the wafer at these points. The channels were sealed to a 3", 1000 µm thick wafer of Corning #7740 borosilicate glass using anodic bonding at a temperature of 450° C. and a voltage of 1000 V. The maximum current during bonding was typically 500 µA.

Example 2

Re-Sensitization of Patch-Clamped Cells Using Microfluidic-Based Buffer Superfusion and Cell Scanning Microchannels were molded in a polymer, polydimethylsiloxane (PDMS), which were then sealed irreversibly onto a glass coverslip to form an enclosed channel having four walls.

The procedure used is the following:

(1) A silicon master used for molding PDMS was fabricated by first cleaning the wafer to ensure good adhesion to the photoresist, followed by spin coating a layer (~50 µm) of negative photoresist (SU 8-50) onto the wafer. This layer of negative photoresist was then soft baked to evaporate the solvents contained in the photoresist. Photolithography with a mask aligner was carried out using a photomask having the appropriate patterns that were prepared using e-beam writing. The exposed wafer was then baked and developed by washing away the unexposed photoresist in an appropriate developer (e.g. propylene glycol methyl ether acetate).

(2) This developed wafer (master) was surface passivated by silanizing in vacuo with a few hundred microliters of tridecafluoro-1,1,2,2-tetrahydrooctyl-1-trichlorosilane for a few hours.

(3) Degassed PDMS prepolymer was poured on top of the silicon master and left in an oven to cure at 60° C. for two hours, (4) The cured PDMS mold containing the microchannel features was then sealed irreversibly to a glass substrate after oxidization in an oxygen plasma for ~1 min. Channel dimensions we used in this example were approximately 100 µm wide and 50 µm deep.

The experiments described here used a simple single-channel structure. This microchannel was interfaced to a polyethylene tubing by first punching a smooth hole through the PDMS with a sharp hole-puncher having the appropriate dimensions. Polyethylene tubing having an outer diameter slightly greater the punched hole was inserted into the hole, and the tubing formed a pressure seal owing to the elastomeric nature of PDMS. The polyethylene tubing was connected to a syringe needle having the appropriate size (gauge), which was connected to a syringe. Controlled pressure for driving fluid flow was accomplished with a high precision syringe pump (CMA/100, Microinjection pump, Carnegei Medicin).

Patch clamp experiments were carried out in the whole-cell configuration. The pipettes for whole-cell recording were fabricated from thick-walled borosilicate glass capillaries having an outer diameter of 1.5 mm and an inner diameter of 0.86 mm (Harvard Apparatus LTD Edenbridge, Kent, UK). The diameters and the resistances of the tips were ~2.5 µM and 5-15 MΩ, respectively. The estimated series resistance was always <50 MΩ and holding potentials were corrected for voltage errors due to series resistance. The patch clamp electrode solution contained 100-mM KCl, 2-mM $MgCl_2$, 1-mM $CaCl_2$, 11-mM EGTA, and 10-mM HEPES; pH was adjusted to 7.2 with KOH. All experiments were performed at room temperature (18-22° C.).

Signals were recorded with an Axopatch 200 A (Axon inc. California, U.S.A) patch-clamp amplifier, at a holding potential of −70 mV, and were digitized and stored on the computer hard drive (sample frequency 10 kHz, filter frequency 200 Hz using a 8 pole Bessel filter) and analyzed using a PC and Clampfit 8.1 software (Axon inc.). The experimental chamber containing the microchannel structure was mounted on an inverted microscope stage equipped with 40× and 10× objectives (Nikon, Japan). Mounted to the microscope was a CCD camera (Hamamatsu) connected to a video for recording of the scan rates, the sampling rate for the video was 25 Hz. This equipment together with micromanipulators (Narishigi, Japan) was placed on a vibration-isolated table inside a Faraday cage. The patch clamp amplifier, the Digidata board, filters, the video and PCs, were kept outside the cage to minimize interference from line frequency.

Adherent PC-12 cells were cultivated on circular cover slips in Petrie dishes for 2-6 days (DMEM/F12 medium supplemented with antibiotics and antimyocotin (0.2%), fetal calf serum (10%), and L-glutamine). Before the patch clamp experiments, cells were washed and detached in a HEPES-saline buffer, containing (in mM): 10 HEPES, 140 NaCl, 5 KCl, 1 $CaCl_2$, 1 $MgCl_2$, 10 D-glucose (pH 7.4), and placed in the open buffer reservoir at the outlet of the microchannel.

The strength of the seals was tested with cells that were patched-clamped without entering into a whole-cell configuration. A membrane holding potential of −70 mV was applied and the cell was positioned 10 µm away from the channel outlet. Different flow rates, which varied between 0.3-21 mm/s, were applied while the seal was continuously monitored. The patched seal was stable (no shift in the current trace) for flow rates up to 6.7 mm/s, in this particular experiment.

For the re-sensitization experiment, agonist was added to the open reservoir where the cell was patched while buffer was delivered from the syringe into the microchannel and exits the microchannel into the open reservoir. The patch-clamped cell was placed ~10 µm away from the outlet of the microchannel. The reservoir in which the patch-clamped cell resides was filled with 1 mM acetylcholine (agonists). Buffer was delivered by the syringe pump into the microchannel and was continuously flown through the microchannel at ~3 mm/s.

Figure 20:
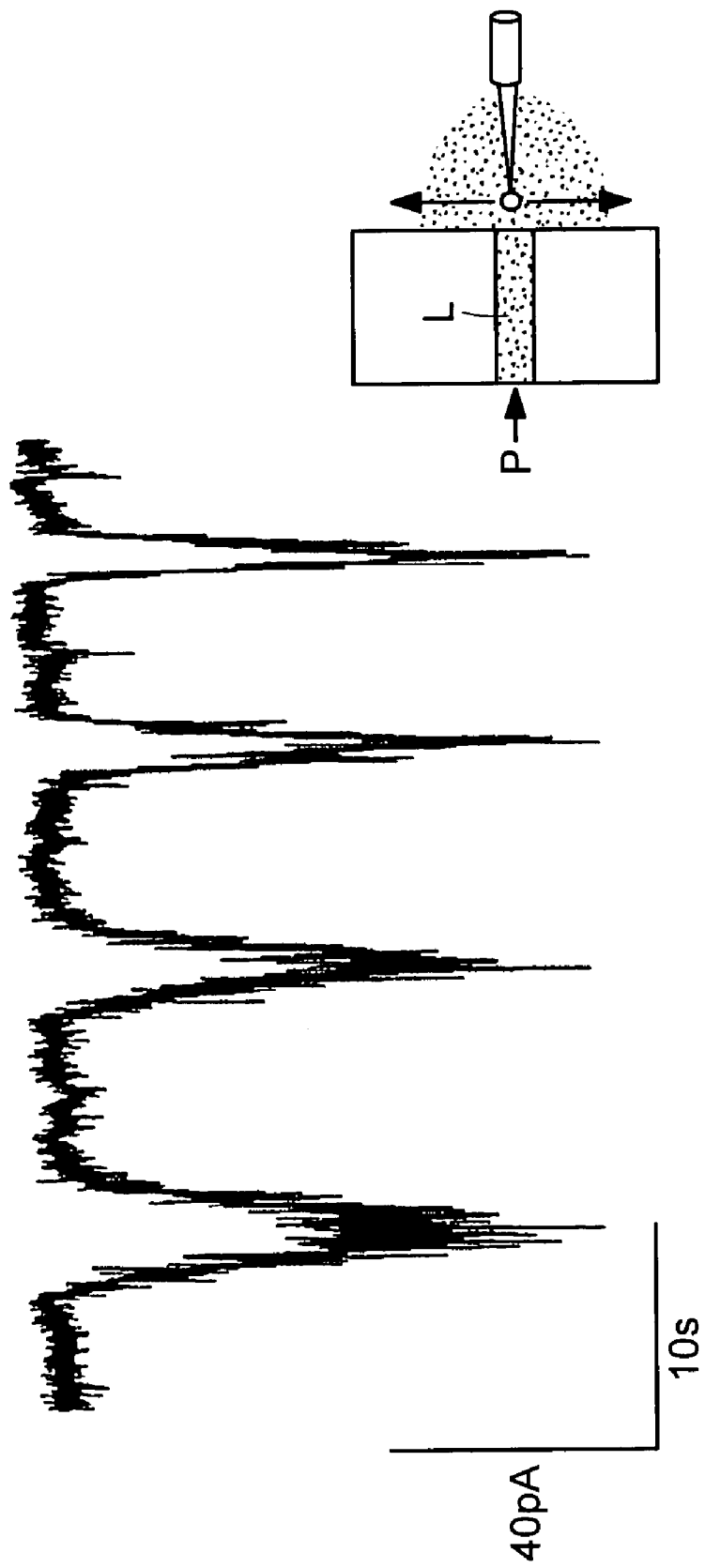
FIG. 20 shows whole cell patch clamp recordings of transmembrane current responses elicited by manual repeated scanning of a cell across the channel outlet where it was superfused by buffer into an open reservoir containing acetylcholine (1 mM). A train of peaks are produced by repeated manual scanning of the patched cell across the superfusion-generated gradient. The cell was scanned back and forth at an average scan rate of 100 μm/s and at a maximum rate of up to 150 μm/s across the entire outlet of the microchannel depicted in the inset.

No current was observed while the giga Ohm seal was stable (5-20 Gohm) as the cell was moved, in a direction parallel to the microchannel, from ~10 µm to ~80 µm from the outlet of the microchannel. This fact means the patch-clamped cell was superfused by the buffer exiting from the microchannel and thus was not in contact with the agonists in the open reservoir. At ~80 µm from the outlet of the microchannel, the patched cell was scanned repeatedly at ~100 µm/s, in a direction perpendicular to the microchannel, between the reservoir containing agonists and the microchannel outlet (FIG. 20).

De-sensitization of the current response could be observed after exposure to the agonist for longer periods of time (>5 s) as a decrease of the mean whole-cell current. No de-sensitization of the cells was seen for the shorter exposure times (<5 s) to the agonist nor for repeatedly short exposures as long as the patched cell was re-sensitized in agonist free buffer between each exposure.

Example 3

Rapid Scanning of a Patch-Clamped Cell Across Interdigitated Streams of Ligands and Buffer for HTS Applications One preferred embodiment for implementing HTS using the current invention is to scan a patch-clamped cell rapidly across interdigitated streams of buffer and ligands, with each ligand stream corresponding to a different drug. In these applications, as discussed above, both the flow rate of the fluids exiting the microchannels and the scan rate of the patch clamped cell are important. FIGS. 21A-D show the response of patch-clamped whole cells after being scanned across the outlets of a 7-channel structure. The width of each channel is 100 μm, the thickness is 50 μm, and the interchannel spacing is 25 μm. This 7-channel structure is identical to that shown in FIG. 16B. The procedure used for fabricating the microchannels and for patch clamping are identical to that described in Example 2 (see above). The patch clamped cell used was a PC-12 cell, which was placed between 10 to 20 micrometers away from the outlets of the microchannels. Channels 1, 3, 5 and 7 were filled with PBS buffer, while channels 2, 4 and 6 were filled with acetylcholine. The flow rate of the fluid streams was 6.8 mm/s.

In FIGS. 21A-D, a patch-clamped cell was scanned across interdigitated streams at four different scan rates: A, 0.61 mm/s; B, 1.22 mm/s; C, 2 mm/s; and D, 4 mm/s. The difference in the scan rate is reflected in the width of the whole cell current response peaks, the wider the width, the longer the transit time and the wider the peak width. In addition, for slow scan rates (e.g., FIG. 21A), the maximal response for each peak decreases as the patch-clamped cell is scanned from one acetylcholine stream to the next. This decrease in the peak response is caused by desensitisation of the patch-clamped cell as a result of the slow scan rate that led to a longer residence time for the cell in the acetylcholine stream.

Figure 22:
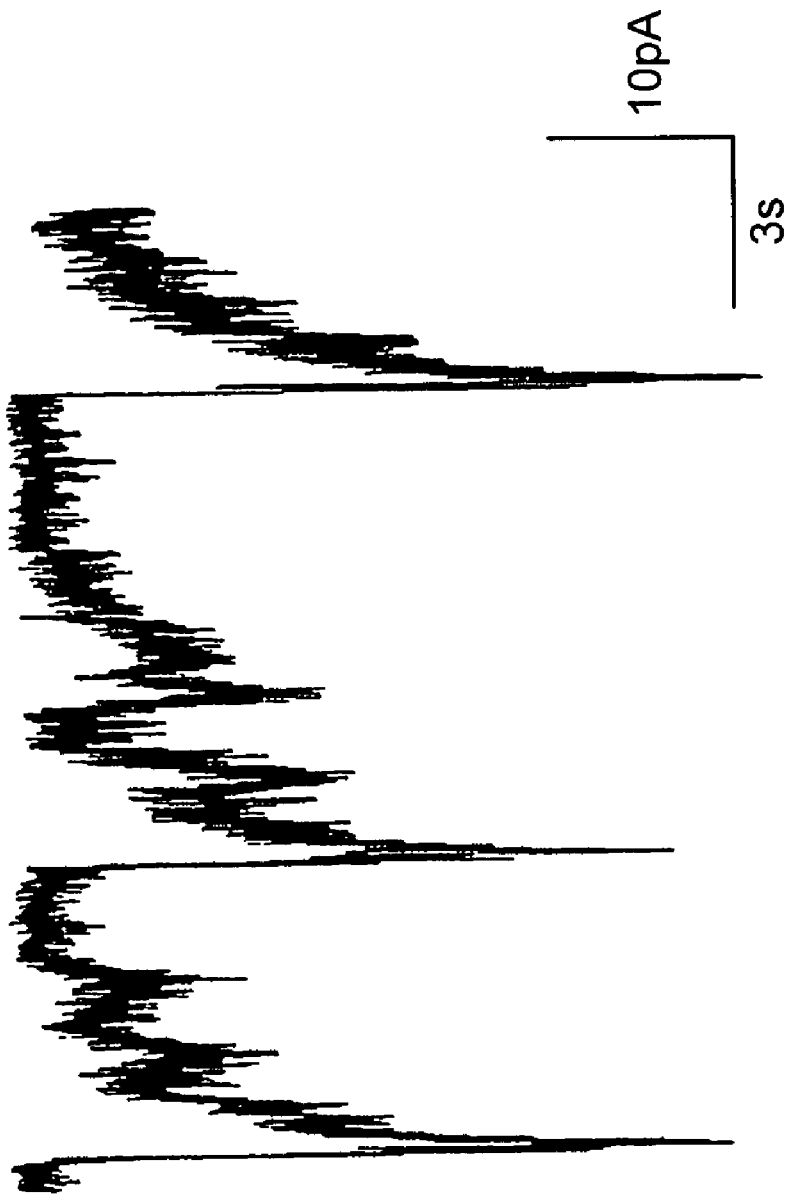
FIG. 22 shows patch clamp current responses of a whole cell to 1 mM acetylcholine as the patch-clamped cell was scanned across the outlets of a 7-channel structure (same structure as that shown in FIG. 16B). Channels 1, 3, 5 and 7 were filled with PBS buffer; channels 2, 4 and 6 with acetylcholine. The channel flow rate was 2.7 mm/s and the cell scanning speed was 6.25 μm/s.

From FIG. 21A, it can seen the decrease in height from the second to third peak is greater when compared to the decrease from the first to second peak. This is consistent with the fact that the longer residence time (i.e., larger peak width) of the patch-clamped cell in the second stream causes more desensitisation. As the scan rate increases (FIGS. 21C and 21D), the residence time in the acetylcholine stream decreases and desensitisation is no longer an issue. For fast scan rates (e.g., tens of ms) as shown, for example, in FIG. 21D, no desensitisation can be detected. FIG. 22 shows the opposite scenario in which the scan rate is slow (seconds), and desensitisation is pronounced as the patch-clamped cell is scanned across the width of the acetylcholine stream.

From these experiments, it is clear that controlling the scan rate is critical for achieving optimal performance of the system for HTS applications. Scanning rates can be controlled by any of the mechanisms described above or by other methods known in the art.

Data obtained by the system relating to the dynamics of desensitisation and re-sensitization can be exploited to provide useful information in elucidating ion-channel pharmacology, kinetics and identity.

Example 4

Figure 23:
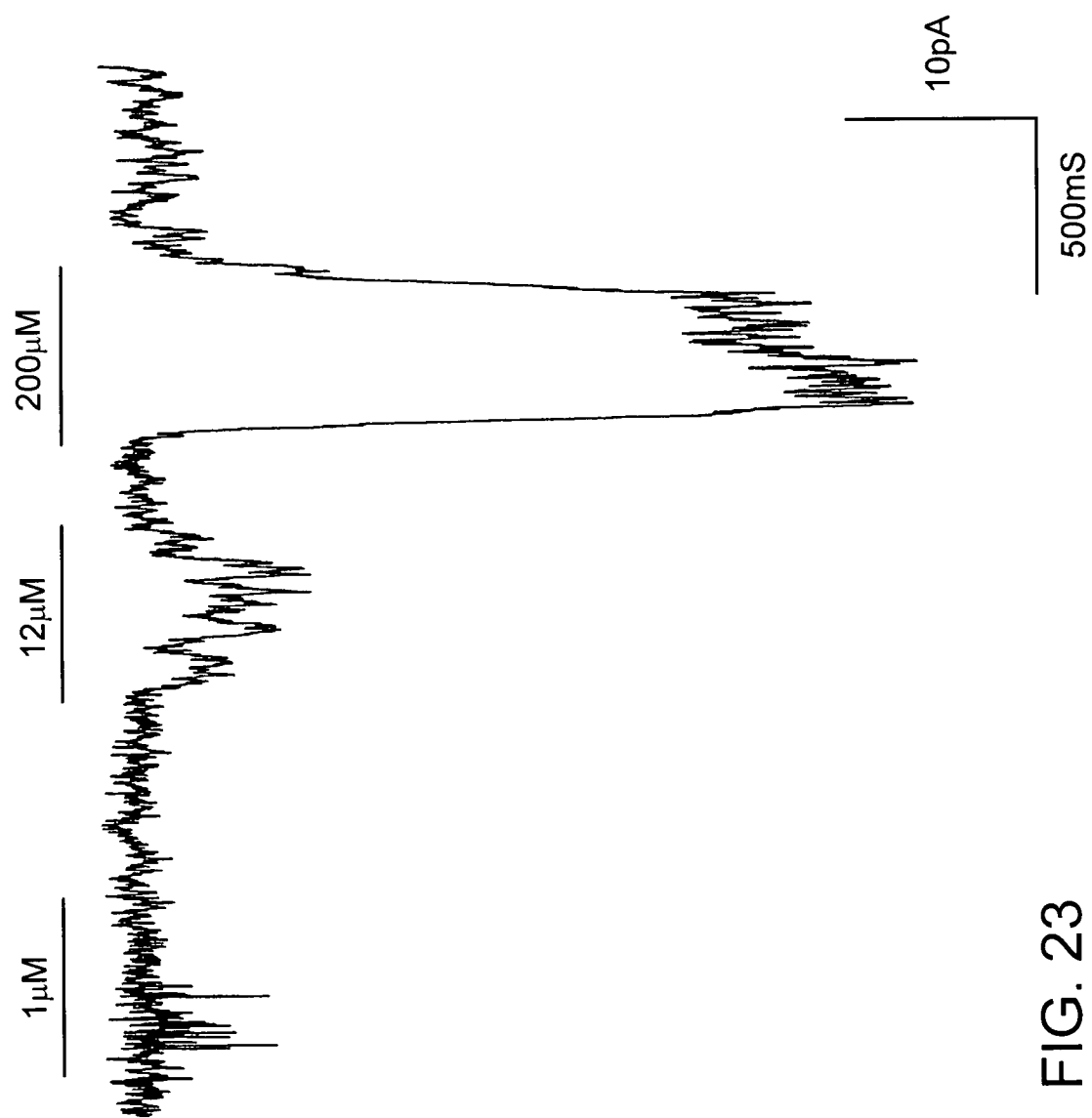
FIG. 23 shows concentration-dependent patch clamp current responses of whole cells to 1 μM, 12 μM and 200 μM nicotine as the patch-clamped cell was scanned across the outlets of a 7-channel structure (same structure as that shown in FIG. 16B); channels 1, 3, 5 and 7 were filled with PBS buffer; channel 2 with 1 μM, 4 with 12 μM and 6 with 200 μM nicotine respectively. The flow rate was 3.24 mm/s and the cell scanning speed was 250 μm/s.

Dose-Response Measurements by Rapid Scanning of a Patch-Clamped Cell Across Interdigitated Streams of Buffer and Ligands Having Different Concentrations The channel structure and experimental setup used in Example 3 can be used to carry out dose-response measurements, in which the concentrations of the ligands in each of the ligand streams differ by predetermined amounts. FIG. 23 shows the result of one such experiment, in which three different concentrations (1 μM, 12 μM and 200 μM) of nicotine were applied to a patch-clamped cell. In this 7-channel structure, channels 1, 3, 5 and 7 were filled with PBS buffer, whereas channels 2, 4, and 6 were filled with 1 μM, 12 μM, and 200 μM nicotine, respectively. The flow rate used was 3.24 mm/s and the cell-scanning speed was 250 μm/s. The patch-clamped cell was placed between 10 to 20 μm away from the outlet of the microchannel.

At 1-μM concentration of nicotine, the whole-cell current response was barely discernible in the patch-clamp trace. The current peak for 12 μM was detected with good signal-to-noise ratio, and the peak that corresponds to 200 μM was approximately 15 to 20 times that of the peak for 12-μM. With these measurements, a dose-response curve can be generated that provides valuable information about drug action and ion-channel pharmacology. It should be emphasized that a number of on-chip techniques for gradient generation as well as off-chip methods for preparing different concentrations of ligands can be used (see, e.g., Dertinger, et al., 2001, *Analytical Chemistry* 73: 1240-1246). In addition, the number of different concentrations used for constructing dose-response curves will in most cases be greater than that used in this example, and will depend on the required concentration resolution and range desired for a particular application.

Variations, modifications, and other implementations of what is described herein will occur to those of ordinary skill in the art without departing from the spirit and scope of the invention. The publications, patents, applications and other references cited herein are all incorporated by reference in their entirety herein.

What is claimed is:

1. A product, comprising:
   (i) a substrate for changing a solution environment around a sensor, the substrate comprising a plurality of microchannels, each microchannel comprising an outlet, and at least one sensor chamber, wherein the outlets of the microchannels intersect with at least one of the sensor chambers;
   (ii) a scanning mechanism for selectively exposing a sensor to multiple fluid streams from the plurality of microchannel outlets, wherein the number of microchannel outlets is three or more; and
   (iii) a processor in communication with the scanning mechanism, wherein the processor is programmed to selectively expose a sensor to multiple fluid streams from the plurality of microchannel outlets.

2. A product, comprising:
   (i) a substrate for changing a solution environment around a sensor, the substrate comprising a plurality of microchannels, each microchannel comprising an outlet, and at least one sensor chamber, wherein the outlets of the microchannels intersect with at least one of the sensor chambers;
   (ii) a scanning mechanism for selectively exposing a sensor to multiple fluid streams from the plurality of microchannel outlets, wherein the number of microchannel outlets is three or more; and (iii) a processor for evaluating and displaying data relating to sensor responses for multiple fluid streams from the plurality of microchannel outlets, where the processor is in communication with a user interface for displaying data, wherein the user interface is a computer or wireless device.

3. A product, comprising:
(i) a substrate for changing a solution environment around a sensor, the substrate comprising a plurality of microchannels, each microchannel comprising an outlet, and at least one sensor chamber, wherein the outlets of the microchannels intersect with at least one of the sensor chambers;
(ii) a scanning mechanism for selectively exposing a sensor to multiple fluid streams from the plurality of microchannel outlets, wherein the number of microchannel outlets is three or more; and
(iii) a mechanism for holding a sensor, wherein the sensor is coupled or connected to a positioner, used for positioning the sensor in proximity to the plurality of microchannel outlets, and the positioner is scanned relative to the outlets using an appropriate scanning mechanism; and
(iv) a processor in communication with the scanning mechanism programmed to selectively expose a sensor to multiple fluid streams and wherein the processor further comprises or communicates with a user interface for displaying data.

4. The product of any one of claims 1, 2, or 3, wherein at least one channel is in communication with a reservoir.

5. The product of claim 4, wherein the reservoir is a buffer reservoir.

6. The product of claim 4, wherein the reservoir is a sample reservoir.

7. The product of claim 6, wherein the reservoir is in communication with a different channel.

8. The product of claim 7, comprising alternating sample and buffer reservoirs.

9. The product of claim 8, wherein the product delivers streams of sample and buffer through interdigitated channels of the substrate.

10. The product of claim 4, comprising a plurality of buffer reservoirs and sample reservoirs.

11. The product of claim 4, further comprising a mechanism for applying positive or negative pressure to the reservoir.

12. The product of claim 4, wherein at least one reservoir is sealed by a septum.

13. The product of claim 12, wherein a tube or needle is inserted into the septum.

14. The product of any one of claims 1, 2, or 3, wherein the scanning mechanism comprises a mechanism for moving the sensor in proximity to an outlet.

15. The product according to any one of claims 1, 2, or 3, wherein the scanning mechanism comprises a mechanism for varying pressure across one or more channels.

16. The product of any one of claims 1, 2, or 3, further comprising a capillary which is in sufficient proximity to a mechanism for holding the sensor, or which can be moved in sufficient proximity to the mechanism for holding the sensor, wherein the capillary is capable of delivering a fluid to the sensor positioned by a positioner.

17. The product of claim 16, wherein the mechanism for holding the sensor comprises a mechanism for holding a cell.

18. The product of claim 16, wherein the fluid from the capillary is a buffer.

19. The product of claim 16, wherein the mechanism for holding the sensor is a pipette and the capillary is coaxial with the pipette.

20. The product of claim 16, wherein the capillary is coupled to a pumping mechanism to provide pulsatile delivery of buffer to the sensor.

21. The product of any one of claims 1, 2 or 3, further comprising a sensor.

22. The product of claim 21, wherein the sensor comprises a cell or a portion of a cell.

23. The product of claim 22, wherein the cell is a patch clamped cell or patch-clamped cell membrane fraction.

24. The product of claim 22, wherein the cell or portion of the cell comprises an ion channel.

25. The product of claim 22, wherein the cell or portion of the cell comprises a G Protein Coupled Receptor.

26. The product according to claim 22, wherein the cell or portion of the cell comprises an activated receptor.

27. The product of claim 22, wherein the cell or portion of the cell is selected from the group consisting of a cultured cell, a bacterial cell, a protist cell, a yeast cell, a plant cell, an insect cell, an avian cell, an amphibian cell, a fish cell, a mammalian cell, an oocyte, a cell expressing a recombinant nucleic acid, and a cell from a patient with a pathological condition.

28. The product of claim 22, wherein the cell or portion of the cell is positioned in proximity to the outlet of a channel using a positioner.

29. The product of claim 22, wherein the cell comprises a receptor and the product delivers a buffer; at least one agonist; at least one agonist and a buffer; at least one antagonist; or at least one antagonist and a buffer through channels of the substrate.

30. The product of claim 29, wherein the at least one agonist and buffer; the at least one antagonist and buffer; or the at least one antagonist, at least one agonist, and buffer, are delivered to the cell through interdigitated channels of the substrate.

31. The product of claim 22, wherein the product comprises a chamber for receiving the cell or portion thereof which is in communication with the channels and wherein the chamber comprises a buffer, at least one agonist; at least one agonist and a buffer; at least one antagonist; at least one antagonist and a buffer; or at least one antagonist, at least one agonist, and a buffer.

32. The product of any one of claims 1, 2 or 3, wherein the product further comprises a sensor, and wherein the sensor is selected from the group consisting of: a surface plasmon energy sensor; an FET sensor; an ISFET; an electrochemical sensor; an optical sensor; an acoustic wave biosensor; a sensor comprising a sensing element associated with a Quantum Dot particle; a polymer-based biosensor; and an array of biomolecules immobilized on a substrate.

33. The product of any one of claims 1, 2 or 3, wherein the product comprises a plurality of sensors.

34. The product of any one of claims 1, 2 or 3, wherein each fluid stream of the plurality of channels is substantially parallel.

35. The product of any one of claims 1, 2, or 3, wherein the diameter of each channel outlet is at least about the diameter of the sensor.

36. The product of claim 35, wherein the sensor comprises a cell.

37. The product of any one of claims 1, 2 or 3, wherein each channel comprises at least one inlet for receiving solution from a reservoir, and wherein the center-to center distance of each reservoir corresponds to the center-to-center distance of wells in a multi-well plate.

38. The product of any one of claims 1, 2 or 3, wherein the substrate further comprises one or more treatment chambers for delivering an electrical current to a cell placed within the treatment chamber.

39. The product of any one of claims 1, 2, or 3, further comprising a mechanism for holding the sensor selected from the group consisting of a pipette or a capillary connected to a positioner, and an optical tweezer.

40. The product of claim 39, wherein the pipette is a patch clamp pipette.

41. The product of any one of claims 1, 2, or 3, further comprising a mechanism for holding the sensor, wherein the sensor comprises an electrode.

42. The product of any one of claims 1, 2 or 3, wherein the scanning mechanism is capable of moving the substrate or the sensor, or both the substrate and the sensor.

43. The product of any one of claims 1, 2 or 3 wherein the processor controls one or more of: the rate of scanning, the direction of scanning, acceleration of scanning, number of scans, pause intervals at a channel and pressure changes across one or more channels.

44. The product of any one of claims 1, 2 or 3, further comprising a detector in communication with the sensor for detecting the responses of a sensor in the chamber.

45. The product of claim 44, wherein the detector communicates with the processor, wherein the processor further comprises or communicates with a data acquisition system.

46. The product of claim 44, wherein the processor further comprises or communicates with a user interface for displaying data related to the responses.

47. The product of claim 46, wherein the user interface is a computer or a wireless device.

48. The product of claim 44, wherein in response to a signal from the detector, the processor alters one or more of the rate of scanning, the direction of scanning, acceleration of scanning, number of scans, and pressure changes across one or more channels.

49. The product of any one of claims 1, 2 or 3, wherein the processor further comprises or communicates with a data analysis system.

50. The product of any one of claims 1, 2 or 3, wherein the product is interfaced to a fluid delivery system operably linked to a micropump for pumping fluids from the fluid delivery system into one or more reservoirs of the substrate.

51. The product of claim 50, wherein the fluid delivery system comprises one or more microtiter plates.

52. The product of claim 50, wherein the fluid delivery system is capable of programmably delivering different types of samples and/or buffer to the one or more reservoirs.

53. The product of claim 50, wherein the fluid delivery system is capable of programmably delivering buffer to at least one reservoir.

54. The product of any one of claims 1, 2 or 3, further comprising at least one output channel for removing fluid from the product.

55. The product of any one of claims 1, 2 or 3, further comprising a mechanism for delivering positive or negative pressure to at least one of the channels.

56. The product of claim 55, wherein the mechanism for delivering pressure is in communication with the processor.

57. The product of claim 56, wherein the processor provides instructions to the mechanism for delivering pressure to one or more selected channels.

58. The product of any one of claims 1, 2 or 3, wherein the substrate is interfaced with a multi-well plate and wherein each well is in fluid communication with a different channel on the substrate.

59. The product of claim 58, wherein wells communicate with the channels through one or more external tubings or capillaries for delivering to the fluid to the channels.

60. The product of claim 59, wherein the one or more tubings or capillaries comprise one or more external valves to control fluid flow through the tubings or capillaries.

61. The product of any one of claims 1, 2 or 3, wherein the substrate comprises a material selected from the group consisting of a crystalline semiconductor material; silicon; silicon nitride; Ge, GaAs; metals; Al, Ni; glass; quartz; crystalline insulator; ceramics; plastics; an elastomeric material; silicone; EPDM; Hostaf Ion; a polymer; a fluoropolymer; Teflon ®; polymethylmethacrylate; polydimethylsiloxane; polyethylene; polypropylene; polybutylene; polymethylpentene; polystyrene; polyurethane; polyvinyl chloride; polyarylate; polyarylsulfone; polycaprolactone; polyestercarbonate; polyimide; polyketone; polyphenylsulfone; polyphthalamide; polysulfone; polyamide; polyester; epoxy polymer; thermoplastic; an organic material; an inorganic material; combinations thereof.

62. The product of any one of claims 1, 2 or 3, wherein the substrate is three-dimensional and at least two of the channels lie at least partially in different planes.

63. The product of claim 62 comprising a first set of channels and a second set of channels and wherein the first set of channels overlies the second set of channels.

64. The product of any one of claims 1, 2 or 3, wherein at least one channel is a mixing channel for combining fluid streams from at least two channels.

65. The product of claim 64, wherein the mixing channel provides a fluid comprising a varying concentration of a substance.

66. The product of any one of claims 1, 2 or 3, wherein the product further comprises a mechanism for holding a sensor and wherein the scanning mechanism is adapted to move the substrate.

67. The product of any one of claims 1, 2 or 3, wherein the microchannels range in width from between 1 µm and 20 µm.

68. The product of any one of claims 1, 2 or 3, wherein the microchannels range in width from between 0.1 µm and 500 µm.

69. The product of any one of claims 1, 2 or 3, wherein the microchannels range in width from between 1 µm and 150 µm.

70. The product of any one of claims 1, 2 or 3, wherein the microchannels range in diameter from between 10 µm and 100 µm.

71. The product of any one of claims 1, 2 or 3, wherein the microchannels range in diameter from between 0.1 µm and 500 µm.

72. The product of any one of claims 1, 2 or 3, wherein the microchannels range in diameter from between 1 µm and 150 µm.

73. The product of any one of claims 1, 2 or 3, wherein the microchannels range in thickness from between 0.1 µm and 500 µm.

74. The product of any one of claims 1, 2 or 3, wherein the microchannels range in thickness from between 1 µm and 150 µm.

75. The product of any one of claims 1, 2, or 3, wherein the number of microchannel outlets is 7 or more.

76. The product of any one of claims 1, 2, or 3, wherein the number of microchannel outlets is 10 or more.

77. The product of any one of claims 1, 2, or 3, wherein the number of microchannel outlets is 96 or more.

* * * * *

(12) INTER PARTES REEXAMINATION CERTIFICATE (804th)
United States Patent
Orwar et al.

(10) Number: US 7,563,614 C1
(45) Certificate Issued: Jan. 17, 2014

(54) SYSTEMS AND METHODS FOR RAPIDLY CHANGING THE SOLUTION ENVIRONMENT AROUND SENSORS

(75) Inventors: Owe Orwar, Hovås (SE); Daniel Chiu, Seattle, WA (US); Johan Pihl, Göteborg (SE); Jon Sinclair, Göteborg (SE); Jessica Olofsson, Göteborg (SE); Mattias Karlsson, Göteborg (SE); Kent Jardemark, Tyreso (SE)

(73) Assignee: Cellectricon AB, Gothenburg (SE)

Reexamination Request:
No. 95/000,548, Jun. 30, 2010

Reexamination Certificate for:
Patent No.: 7,563,614
Issued: Jul. 21, 2009
Appl. No.: 10/345,107
Filed: Jan. 15, 2003

Related U.S. Application Data

(60) Provisional application No. 60/356,377, filed on Feb. 12, 2002.

(51) Int. Cl.
| | |
|---|---|
| *C12M 1/34* | (2006.01) |
| *G01N 35/00* | (2006.01) |
| *B01L 3/02* | (2006.01) |
| *B01L 3/00* | (2006.01) |
| *B82Y 5/00* | (2011.01) |
| *B82Y 20/00* | (2011.01) |
| *G01N 33/543* | (2006.01) |
| *G01N 33/554* | (2006.01) |

(52) U.S. Cl.
CPC ......... *B01L 3/0293* (2013.01); *B01L 3/502715* (2013.01); *B82Y 5/00* (2013.01); *B82Y 20/00* (2013.01); *G01N 33/54366* (2013.01); *G01N 33/554* (2013.01); *B01L 2200/027* (2013.01); *B01L 2200/10* (2013.01); *B01L 2300/0636* (2013.01); *B01L 2300/0816* (2013.01); *B01L 2300/0867* (2013.01); *B01L 2300/0874* (2013.01); *B01L 2400/0487* (2013.01)
USPC .......... 435/286.2; 422/130; 422/417; 422/63; 435/287.3; 435/288.5

(58) Field of Classification Search
None
See application file for complete search history.

(56) References Cited

To view the complete listing of prior art documents cited during the proceeding for Reexamination Control Number 95/000,548, please refer to the USPTO's public Patent Application Information Retrieval (PAIR) system under the Display References tab.

*Primary Examiner* — Krisanne Jastrzab

(57) ABSTRACT

The invention provides microfluidic systems for altering the solution environment around a nanoscopic or microscopic object, such as a sensor, and methods for using the same. The invention can be applied in any sensor technology in which the sensing element needs to be exposed rapidly, sequentially, and controllably, to a large number of different solution environments whose characteristics may be known or unknown.

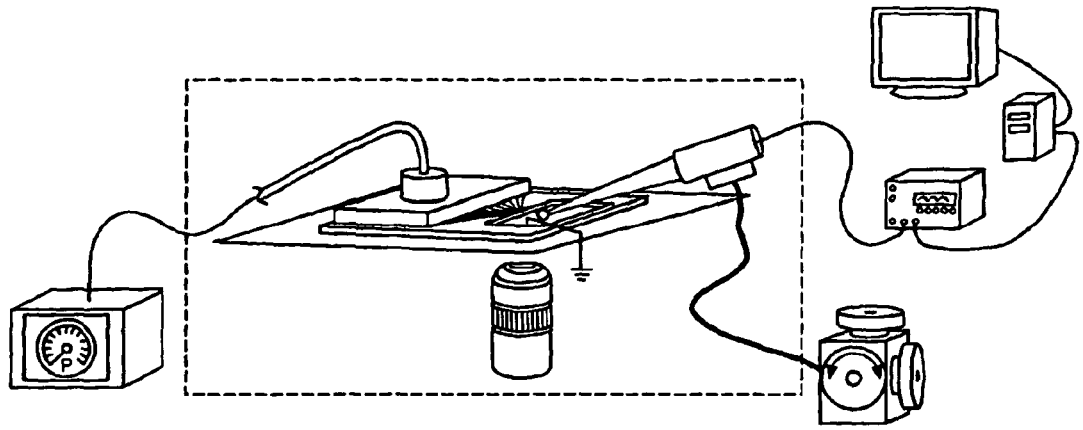

INTER PARTES REEXAMINATION CERTIFICATE ISSUED UNDER 35 U.S.C. 316

NO AMENDMENTS HAVE BEEN MADE TO THE PATENT

AS A RESULT OF REEXAMINATION, IT HAS BEEN DETERMINED THAT:

The patentability of claims 1-2, 4-11, 15, 21-24, 26-27, 29-31, 33-38, 41, 44-47, 49, 54-58, 61-62 and 67-75 is confirmed.

Claims 3, 12-14, 16-20, 25, 28, 32, 39-40, 42-43, 48, 50-53, 59-60, 63-66 and 76-77 were not reexamined.

\* \* \* \* \*